(12) United States Patent
Pierce et al.

(10) Patent No.: US 11,439,637 B2
(45) Date of Patent: Sep. 13, 2022

(54) ANTIPROLIFERATIVE COMPOUNDS AND BISPECIFIC ANTIBODY AGAINST BCMA AND CD3 FOR COMBINED USE

(71) Applicant: Celgene Corporation, Summit, NJ (US)

(72) Inventors: Daniel W. Pierce, Belmont, CA (US); Lilly L. Wong, Solana Beach, CA (US)

(73) Assignee: Celgene Corporation, Summit, NJ (US)

( * ) Notice: Subject to any disclaimer, the term of this patent is extended or adjusted under 35 U.S.C. 154(b) by 455 days.

(21) Appl. No.: 16/419,971

(22) Filed: May 22, 2019

(65) Prior Publication Data

US 2019/0381035 A1 Dec. 19, 2019

Related U.S. Application Data

(60) Provisional application No. 62/675,639, filed on May 23, 2018.

(51) Int. Cl.
| | | |
|---|---|---|
| *A61K 31/496* | (2006.01) | |
| *A61P 35/02* | (2006.01) | |
| *C07K 16/28* | (2006.01) | |
| *A61K 45/06* | (2006.01) | |

(52) U.S. Cl.
CPC .......... *A61K 31/496* (2013.01); *A61P 35/02* (2018.01); *C07K 16/2809* (2013.01); *C07K 16/2878* (2013.01); *A61K 45/06* (2013.01)

(58) Field of Classification Search
None
See application file for complete search history.

(56) References Cited

FOREIGN PATENT DOCUMENTS

| WO | 20170214450 | * | 2/2017 |
|---|---|---|---|
| WO | WO 2017/021450 A1 | | 2/2017 |
| WO | WO 2018/075820 A2 | | 4/2018 |
| WO | 2018083204 | * | 5/2018 |
| WO | WO 2018/083204 A1 | | 5/2018 |
| WO | 2019014100 | * | 1/2019 |
| WO | WO 2019/014100 A1 | | 1/2019 |

OTHER PUBLICATIONS

National Center for Biotechnology Information (2022). PubChem Compound Summary for CID 67332604. Retrieved Aug. 2, 2022 from https://pubchem.ncbi.nlm.nih.gov/compound/67332604.

* cited by examiner

*Primary Examiner* — Karl J Puttlitz
(74) *Attorney, Agent, or Firm* — Jones Day

(57) ABSTRACT

Provided herein is are methods of using 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof and a bispecific antibody specifically binding to human B cell maturation antigen (BCMA) and to human CD3ε (CD3) provided herein, in treating, preventing or managing multiple myeloma.

20 Claims, 6 Drawing Sheets

Figure 1A:
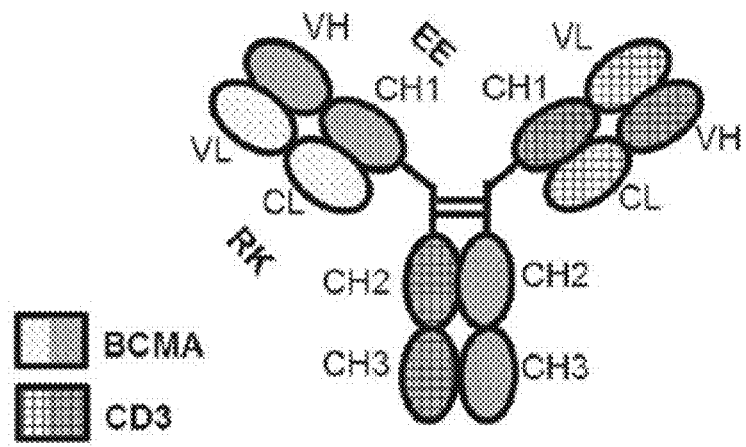

Specification includes a Sequence Listing.

Donor D

Donor E

Donor F

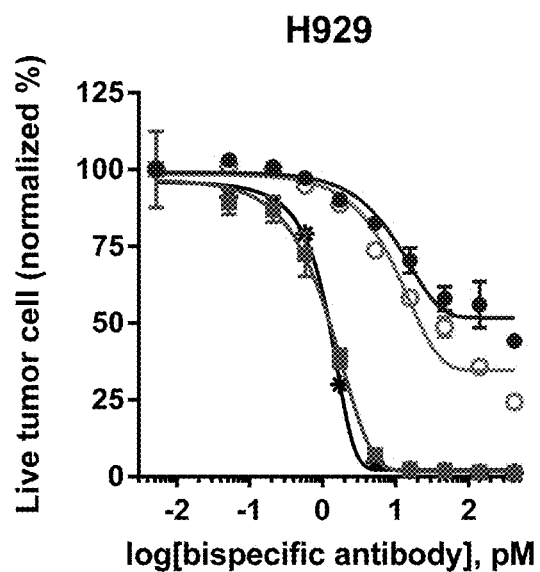
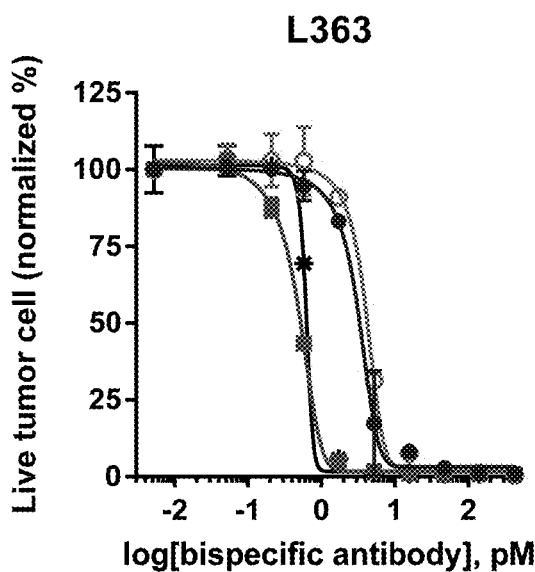
Figure 4A
Figure 4B
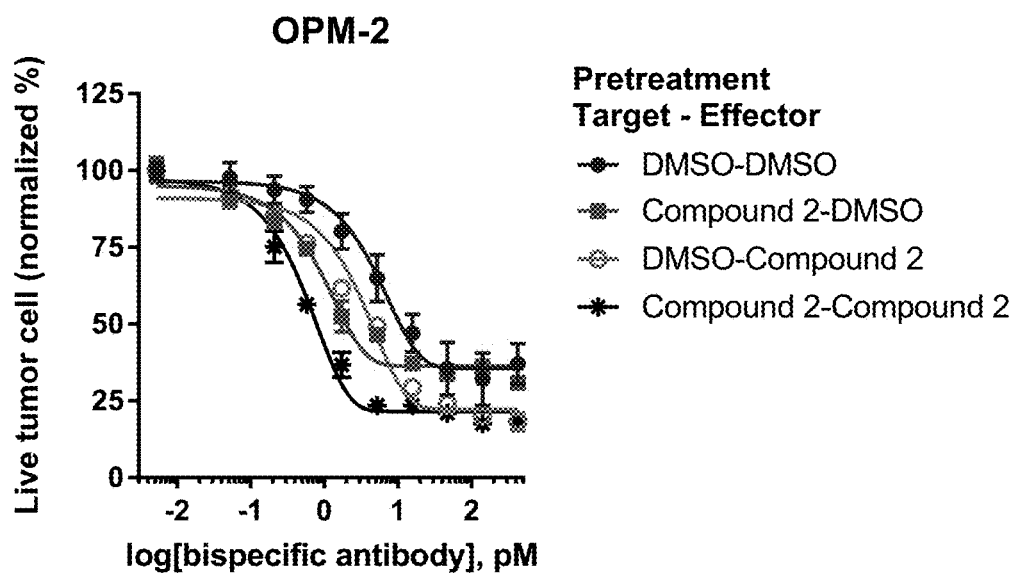
Figure 4C

ANTIPROLIFERATIVE COMPOUNDS AND BISPECIFIC ANTIBODY AGAINST BCMA AND CD3 FOR COMBINED USE

This application claims priority to U.S. Provisional Application No. 62/675,639, filed May 23, 2018, the entirety of which is incorporated herein by reference.

This application contains a Sequence Listing which is submitted electronically as filename 10624-451-999_Seq-Listing.txt, created on May 21, 2019 and 70,646 bytes in size. The Sequence Listing is incorporated herein by reference in its entirety.

1. FIELD

Provided herein are methods of using 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, in combination with a bispecific antibody specifically binding to human B cell maturation antigen (BCMA) and to human CD3ε (CD3), for treating, preventing or managing multiple myeloma.

2. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgeries, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer multiple myeloma cells as a proportion of total bone marrow mononuclear cells is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and $10^{-6}$ by high-throughput sequencing. (Rawstron et al., *Blood* 2015; 125(12):1932-1935). Methods for measuring MRD include DNA sequencing of VDJ, polymerase chain reaction (PCR) (including allele specific PCR, ASO PCR) and multiparameter flow cytometry (MPF). Assays for MRD, e.g., based on clonotype profile measurement are also described in U.S. Pat. No. 8,628,927, to Faham et al., which is incorporated herein by reference.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

Citation or identification of any reference in Section 2 of this application is not to be construed as an admission that the reference is prior art to the present application.

In general, the technical teaching of one embodiment provided herein can be combined with that disclosed in any other embodiments provided herein.

3. SUMMARY

Provided herein are methods of using 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, in combination with a bispecific antibody specifically binding to human B cell maturation antigen (BCMA) and to human CD3ε (CD3), for treating, preventing or managing multiple myeloma.

In one such embodiment, the compound for use in the compositions and methods provided herein is 4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1):

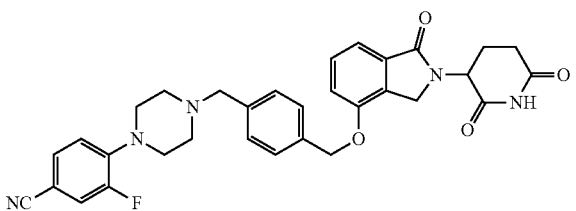

or an enantiomer, mixture of enantiomers, tautomer, isotopolog, or pharmaceutically acceptable salt thereof.

In one other embodiment, the compound for use in the compositions and methods provided herein is (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2):

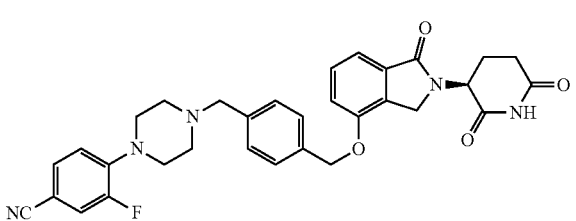

or a tautomer, isotopolog, or pharmaceutically acceptable salt thereof.

In yet another embodiment, the compound for use in the compositions and methods provided herein is (R)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 3):

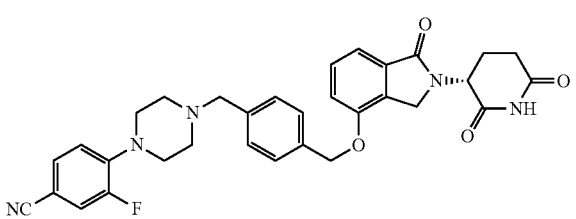

or a tautomer, isotopolog, or pharmaceutically acceptable salt thereof.

In one embodiment, the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

Also provided for use in the methods described herein are pharmaceutical compositions formulated for administration by an appropriate route and means containing effective concentrations of the compounds provided herein, for example Compound 1, Compound 2 or Compound 3, or an enantiomer, mixture of enantiomers, tautomer, isotopolog, or pharmaceutically acceptable salt thereof, and optionally comprising at least one pharmaceutical carrier. Also provided for use in the methods described herein are pharmaceutical compositions formulated for administration by an appropriate route and means containing effective concentrations of the antibodies provided herein, for example, a bispecific antibody comprising a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, the pharmaceutical compositions deliver amounts effective for the treatment of multiple myeloma. In one embodiment, the pharmaceutical compositions deliver amounts effective for the prevention of multiple myeloma. In one embodiment, the pharmaceutical compositions deliver amounts effective for the amelioration of multiple myeloma.

Also provided herein are combination therapies using the compounds or compositions provided herein, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein, in combination with another therapy e.g., another pharmaceutical agent with activity against multiple myeloma or its symptoms. Examples of therapies within the scope of the methods include, but are not limited to, surgery, chemotherapy, radiation therapy, biological therapy, stem cell transplantation, cell therapy, and combinations thereof.

The compounds or compositions provided herein, or pharmaceutically acceptable derivatives thereof, may be administered simultaneously with, prior to, or after administration of each other and one or more of the above therapies. Pharmaceutical compositions containing a compound provided herein and one or more of the above therapies are also provided.

In practicing the methods, effective amounts of the compounds or compositions containing therapeutically effective concentrations of the compounds are administered to an individual exhibiting the symptoms of multiple myeloma to be treated. The amounts are effective to ameliorate or eliminate one or more symptoms of multiple myeloma.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

4. DETAILED DESCRIPTION OF THE INVENTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The use of the word "a" or "an" when used in conjunction with the term "comprising" in the claims and/or the description can mean "one", but it is also consistent with the meaning of "one or more", "at least one" and "one or more than one".

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

"$IC_{50}$" refers to an amount, concentration or dosage of a particular test compound that achieves a 50% inhibition of a maximal response, such as receptor binding, receptor activity, cell growth or proliferation, measured via any of the in vitro or cell based assays described herein.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

Unless specifically stated otherwise, where a compound may assume alternative tautomeric, regioisomeric and/or stereoisomeric forms, all alternative isomers are intended to be encompassed within the scope of the claimed subject matter. For example, where a compound can have one of two tautomeric forms, it is intended that both tautomers be encompassed herein.

Thus, the compounds provided herein may be enantiomerically pure, or be stereoisomeric or diastereomeric mixtures. As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, in one embodiment greater than about 90% by weight of one stereoisomer of the compound and less than about 10% by weight of the other stereoisomers of the compound, in one embodiment greater than about 95% by weight of one stereoisomer of the compound and less than about 5% by weight of the other stereoisomers of the compound, and in one embodiment greater than about 97% by weight of one stereoisomer of the compound and less than about 3% by weight of the other stereoisomers of the compound. A stereomerically pure compound as used herein comprises greater than about 80% by weight of one stereoisomer of the compound, in one embodiment greater than about 90% by weight of one stereoisomer of the compound, in one embodiment greater than about 95% by weight of one stereoisomer of the compound, and in one embodiment greater than about 97% by weight of one stereoisomer of the compound. As used herein and unless otherwise indicated, the term "stereomerically enriched" means a composition that comprises greater than about 60% by weight of one stereoisomer of a compound, in one embodiment greater than about 70% by weight, and in one embodiment greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. As used herein, stereoisomeric or diastereomeric mixtures means a composition that comprises more than one stereoisomer of a compound. A typical stereoisomeric mixture of a compound comprises about 50% by weight of one stereoisomer of the compound and about 50% by weight of other stereoisomers of the compound, or comprises greater than about 50% by weight of one stereoisomer of the compound and less than about 50% by weight of other stereoisomers of the compound, or comprises greater than about 45% by weight of one stereoisomer of the compound and less than about 55% by weight of the other stereoisomers of the compound, or comprises greater than about 40% by weight of one stereoisomer of the compound and less than about 60% by weight of the other stereoisomers of the compound, or comprises greater than about 35% by weight of one stereoisomer of the compound and less than about 65% by weight of the other stereoisomers of the compound.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., multiple myeloma therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues of Compound 1, Compound 2 or Compound 3 are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center.

In the description herein, if there is any discrepancy between a chemical name and chemical structure, the structure controls.

As used herein "multiple myeloma" refers to hematological conditions characterized by malignant plasma cells and includes the following disorders: monoclonal gammopathy of undetermined significance (MGUS); relapsed, refractory or resistant multiple myeloma; low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smouldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(11;14)(q13;q32); t(6;14)(p21;32); t(12; 14)(p13; q32); or t(6;20); MMSET translocations (for example, t(4; 14)(p16;q32)); MAF translocations (for example, t(14;16)(q32;q32); t(20;22); t(16; 22)(q11;q13); or t(14;20)(q32; q11)); or other chromosome factors (for example, deletion of 17p13, or chromosome 13; del(17/17p), nonhyperdiploidy, and gain(1q)).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

The term "relapsed" refers to a situation where patients who have had a remission of multiple myeloma after therapy have a return of myeloma cells and/or reduced normal cells in the marrow.

The term "refractory or resistant" refers to a circumstance where patients, even after intensive treatment, have residual myeloma cells and/or reduced normal cells in the marrow.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another therapy, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with Compound 1, Compound 2 or Compound 3, or an enantiomer or a mixture of enantiomers, tautomers, isotopolog or a pharmaceutically acceptable salt thereof.

The term "biological therapy" refers to administration of biological therapeutics such as cord blood, stem cells, growth factors and the like.

In the context of a cancer, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response ≥partial response (PR), according to the IMWG Uniform Response Criteria. In one embodiment, duration of response (DoR) is the time from achieving a response until relapse or disease progression. In one embodiment, DoR is the time from achieving a response ≥partial response (PR) until relapse or disease progression. In one embodiment, DoR is the time from the first documentation of a response until to the first documentation of progressive disease or death. In one embodiment, DoR is the time from the first documentation of a response ≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response ≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In the context of multiple myeloma, response may be assessed using the International Myeloma Working Group (IMWG) consensus criteria for response and minimal residual disease assessment (Rajkumar et al., *Blood*, 2011, 117(18):4691-5; Kumar et al., *Lancet Oncol.*, 2016,17(8): e328-e346). The criteria can be summarized as follows (with further details available in *Lancet Oncol.*, 2016,17(8):e328-e346).

| Response Criteria | |
|---|---|
| MWG MRD criteria (requires a complete response as defined below) | |
| Sustained MRD-negative | MRD negativity in the marrow (NGF or NGS, or both) and by imaging as defined below, confirmed minimum of 1 year apart. Subsequent evaluations can be used to further specify the duration of negativity (eg, MRD-negative at 5 years) |
| Flow MRD-negative | Absence of phenotypically aberrant clonal plasma cells by NGF on bone marrow aspirates using the EuroFlow standard operation procedure for MRD detection in multiple myeloma (or validated equivalent method) with a minimum sensitivity of 1 in $10^5$ nucleated cells or higher |
| Sequencing MRD-negative | Absence of clonal plasma cells by NGS on bone marrow aspirate in which presence of a clone is defined as less than two identical sequencing reads obtained after DNA sequencing of bone marrow aspirates using the LymphoSIGHT platform (or validated equivalent method) with a minimum sensitivity of 1 in $10^5$ nucleated cells or higher |
| Imaging plus MRD-negative | MRD negativity as defined by NGF or NGS plus disappearance of every area of increased tracer uptake found at baseline or a preceding PET/CT or decrease to less mediastinal blood pool SUV or decrease to less than that of surrounding normal tissue |
| Standard IMWG response criteria | |
| Stringent complete response | Complete response as defined below plus normal FLC ratio and absence of clonal cells in bone marrow biopsy by immunohistochemistry (κ/λ ratio ≤4:1 or ≥1:2 for κ and λ patients, respectively, after counting ≥100 plasma cells) |
| Complete response | Negative immunofixation on the serum and urine and disappearance of any soft tissue plasmacytomas and <5% plasma cells in bone marrow aspirates |
| Very good partial response | Serum and urine M-protein detectable by immunofixation but not on electrophoresis or ≥90% reduction in serum M-protein plus urine M-protein level <100 mg per 24 h |
| Partial response | ≥50% reduction of serum M-protein plus reduction in 24 h urinary M-protein by ≥90% or to <200 mg per 24 h; If the serum and urine M-protein are unmeasurable, a ≥50% decrease in the difference between involved and uninvolved FLC levels is required in place of the M-protein criteria; If serum and urine M-protein are unmeasurable, and serum-free light assay is also unmeasurable, ≥50% |

| | Response Criteria |
|---|---|
| | reduction in plasma cells is required in place of M-protein, provided baseline bone marrow plasma-cell percentage was ≥30%. In addition to these criteria, if present at baseline, a ≥50% reduction in the size (SPD) of soft tissue plasmacytomas is also required |
| Minimal response | ≥25% but ≤49% reduction of serum M-protein and reduction in 24-h urine M-protein by 50-89%. In addition to the above listed criteria, if present at baseline, a ≥50% reduction in the size (SPD) of soft tissue plasmacytomas is also required |
| Stable disease | Not recommended for use as an indicator of response; stability of disease is best described by providing the time-to-progression estimates. Not meeting criteria for complete response, very good partial response, partial response, minimal response, or progressive disease |
| Progressive disease | Any one or more of the following criteria: Increase of 25% from lowest confirmed response value in one or more of the following criteria: Serum M-protein (absolute increase must be ≥0·5 g/dL); Serum M-protein increase ≥1 g/dL, if the lowest M component was ≥5 g/dL; Urine M-protein (absolute increase must be ≥200 mg/24 h); In patients without measurable serum and urine M-protein levels, the difference between involved and uninvolved FLC levels (absolute increase must be >10 mg/dL); In patients without measurable serum and urine M-protein levels and without measurable involved FLC levels, bone marrow plasma-cell percentage irrespective of baseline status (absolute increase must be ≥10%); Appearance of a new lesion(s), ≥50% increase from nadir in SPD of >1 lesion, or ≥50% increase in the longest diameter of a previous lesion >1 cm in short axis; ≥50% increase in circulating plasma cells (minimum of 200 cells per μL) if this is the only measure of disease |
| Clinical relapse | Clinical relapse requires one or more of the following criteria: Direct indicators of increasing disease and/or end organ dysfunction (CRAB features) related to the underlying clonal plasma-cell proliferative disorder. It is not used in calculation of time to progression or progression-free survival but is listed as something that can be reported optionally or for use in clinical practice; Development of new soft tissue plasmacytomas or bone lesions (osteoporotic fractures do not constitute progression); Definite increase in the size of existing plasmacytomas or bone lesions. A definite increase is defined as a 50% (and ≥1 cm) increase as measured serially by the SPD of the measurable lesion; Hypercalcaemia (>11 mg/dL); Decrease in haemoglobin of ≥2 g/dL not related to therapy or other non-myeloma-related conditions; Rise in serum creatinine by 2 mg/dL or more from the start of the therapy and attributable to myeloma; Hyperviscosity related to serum paraprotein |
| Relapse from complete response (to be used only if the end point is disease-free survival) | Any one or more of the following criteria: Reappearance of serum or urine M-protein by immunofixation or electrophoresis; Development of ≥5% plasma cells in the bone marrow; Appearance of any other sign of progression (ie, new plasmacytoma, lytic bone lesion, or hypercalcaemia see above) |
| Relapse from MRD negative (to be used only if the end point is disease-free survival) | Any one or more of the following criteria: Loss of MRD negative state (evidence of clonal plasma cells on NGF or NGS, or positive imaging study for recurrence of myeloma); Reappearance of serum or urine M-protein by immunofixation or electrophoresis; Development of ≥5% clonal plasma cells in the bone marrow; Appearance of any other sign of progression (ie, new plasmacytoma, lytic bone lesion, or hypercalcaemia) |

RD = minimal residual disease.

NGF = next-generation flow.

NGS = next-generation sequencing.

FLC = free light chain.

M-protein = myeloma protein.

SPD = sum of the products of the maximal perpendicular diameters of measured lesions.

CRAB features = calcium elevation, renal failure, anaemia, lytic bone lesions.

FCM = flow cytometry.

SUVmax = maximum standardised uptake value.

$^{18}$F-FDG PET = $^{18}$F-fluorodeoxyglucose PET.

In certain embodiments, the treatment of multiple myeloma may also be assessed by the International Uniform Response Criteria for Multiple Myeloma (IURC) (see Durie B G M, Harousseau J-L, Miguel J S, et al. International uniform response criteria for multiple myeloma. *Leukemia*, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h If the serum and urine M-protein are unmeasurable,[d] a ≥50% decrease in the difference between involved and uninvolved FLC levels is required in place of the M-protein criteria If serum and urine M-protein are unmeasurable, and serum free light assay is also unmeasurable, ≥50% reduction in plasma cells is required in place of M-protein, provided baseline bone marrow plasma cell percentage was ≥30% In addition to the above listed criteria, if present at baseline, a ≥50% reduction in the size of soft tissue plasmacytomas is also required |

| Response Subcategory | Response Criteria[a] |
|---|---|
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response.

[a]All response categories require two consecutive assessments made at any time before the institution of any new therapy; all categories also require no known evidence of progressive or new bone lesions if radiographic studies were performed. Radiographic studies are not required to satisfy these response requirements
[b]Confirmation with repeat bone marrow biopsy not needed.
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, eg, light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

The term "about" as used herein, unless otherwise indicated, when used in connection with a numeric value or a range of values, indicates that the value or range of values may deviate to an extent deemed reasonable to one of ordinary skill in the art. In one embodiment, the term "about" indicates that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. In one embodiment, the term "about" refers to a value that is no more than 10% above or below the value being modified by the term. For example, the term "about 10 mg/m$^2$" means a range of from 9 mg/m$^2$ to 11 mg/m$^2$.

The term "BCMA, the target BCMA, human BCMA" as used herein relates to human B cell maturation antigen, also known as BCMA; TR17_HUMAN, TNFRSF17 (UniProt Q02223), which is a member of the tumor necrosis receptor superfamily that is preferentially expressed in differentiated plasma cells. The extracellular domain of BCMA consists according to UniProt of amino acids 1-54 (or 5-51). The term "antibody against BCMA, anti-BCMA antibody" as used herein relates to an antibody specifically binding to the extracellular domain of BCMA.

"Specifically binding to BCMA or binding to BCMA" refer to an antibody that is capable of binding to the target BCMA with sufficient affinity such that the antibody is useful as a therapeutic agent in targeting BCMA. In some embodiments, the extent of binding of an anti-BCMA antibody to an unrelated, non-BCMA protein is about 10-fold preferably >100-fold less than the binding of the antibody to BCMA as measured, e.g., by surface plasmon resonance (SPR) e.g. Biacore®, enzyme linked immunosorbent (ELISA) or flow cytometry (FACS). In one embodiment the antibody that binds to BCMA has a dissociation constant (Kd) of $10^{-8}$ M or less, in one embodiment from $10^{-8}$ M to $10^{-13}$ M, in one embodiment from $10^{-9}$ M to $10^{-13}$ M. In one embodiment the anti-BCMA antibody binds to an epitope of BCMA that is conserved among BCMA from different species, in one embodiment among human and cynomolgus, and in addition embodiment also to mouse and rat BCMA. "Bispecific antibody specifically binding to CD3 and BCMA, bispecific antibody against CD3 and BCMA" refers to a respective definition for binding to both targets. An antibody specifically binding to BCMA (or BCMA and CD3) does not bind to other human antigens. Therefore in an ELISA, OD values for such unrelated targets will be equal or lower to that of the limit of detection of the specific assay, in one embodiment >0.3 ng/mL, or equal or lower to OD values of control samples without plate-bound-BCMA or with untransfected HEK293 cells.

The term "APRIL" as used herein relates to recombinant, truncated murine APRIL (amino acids 106-241; NP_076006). APRIL can be produced as described in Ryan, 2007 (Mol Cancer Ther; 6 (11): 3009-18).

The term "BAFF" as used herein relates to recombinant, truncated human BAFF (UniProt Q9Y275 (TN13B_HUMAN) which can be produced as described in Gordon, 2003 (Biochemistry; 42 (20): 5977-5983). In one embodiment a His-tagged BAFF is used according to the invention. In one embodiment the His-tagged BAFF is produced by cloning a DNA fragment encoding BAFF residues 82-285 into an expression vector, creating a fusion with an N-terminal His-tag followed by a thrombin cleavage site, expressing said vector and cleaving the recovered protein with thrombin.

The term "antibody against CD3, anti CD3 antibody" relates to an antibody specifically binding to CD3. In one embodiment, the antibody specifically binds to CD3ε. The term "CD3ε or CD3" as used herein relates to human CD3ε described under UniProt P07766 (CD3E_HUMAN).

The term "antibody" as used herein refers to a monoclonal antibody. An antibody consists of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. Each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order: FR1, CDR1, FR2, CDR2, FR3, CDR3, FR4. The "constant domains" of the heavy chain and of the light chain are not involved directly in binding of an antibody to a target, but exhibit various effector functions. The term "antibody" as used herein comprises also the portion of an antibody which is needed at least for specific binding to the antigen CD3 resp. BCMA. Therefore such an antibody (or antibody portion) can be in one embodiment a Fab fragment, if said antibody portion is comprised in a bispecific antibody according to the invention. The antibody according to the invention can also be a Fab', F(ab')$_2$, a scFv, a di-scFv, or a bi-specific T-cell engager (BiTE®).

The term "antibody" includes e.g. mouse antibodies, human antibodies, chimeric antibodies, humanized antibodies and genetically engineered antibodies (variant or mutant antibodies) as long as their characteristic properties are retained. In one embodiment, the antibodies are human or humanized antibodies, especially as recombinant human or humanized antibodies. Further embodiments are heterospecific antibodies (bispecific, trispecific etc.) and other conjugates, e.g. with cytotoxic small molecules.

Bispecific antibody formats are well known in the state of the art and e.g. also described in Kontermann R E, mAbs 4:2 1-16 (2012); Holliger P., Hudson P J, Nature Biotech. 23 (2005) 1126-1136 and Chan A C, Carter P J Nature Reviews Immunology 10, 301-316 (2010) and Cuesta A M et al., Trends Biotech 28 (2011) 355-362. The term "bispecific antibody" as used herein refers in one embodiment to an antibody in which one of the two pairs of heavy chain and light chain (HC/LC) is specifically binding to CD3 and the other one is specifically binding to BCMA. The term also refers to other formats of bispecific antibodies according to the state of the art. In one embodiment, the term "bispecific antibody" includes bispecific single-chain antibodies, such as antibodies in the BiTE® format, DART antibodies, diabodies, tandem scFvs and antibody mimetics such as DARPins. In one embodiment, the bispecific antibody specifically binding to human B cell maturation antigen (BCMA) and to human CD3ε (CD3) is one of those described in international application publication No. WO 2018/083204, the entirety of which is incorporated herein by reference.

Figures 2A, 2B:
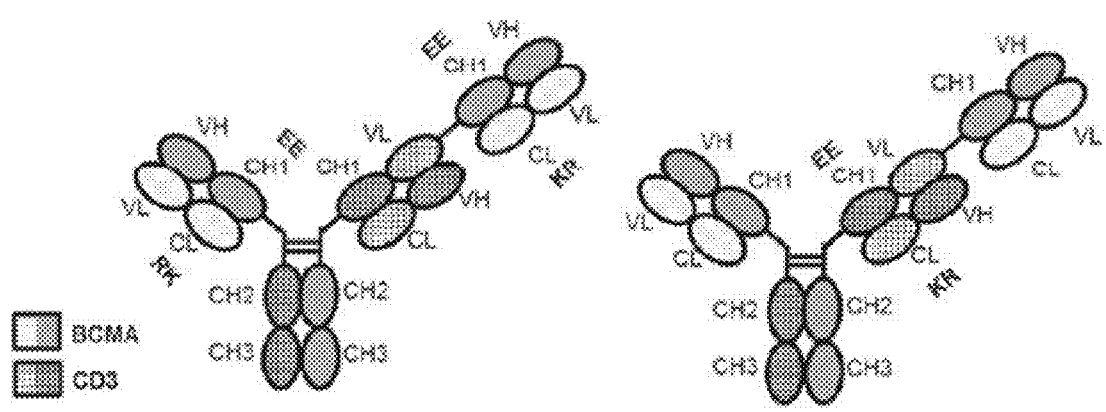

The term "TCB" as used herein refer to a bispecific antibody specifically binding to BCMA and CD3. The term "83A10-TCBcv" as used herein refer to a bispecific antibody specifically binding to BCMA and CD3 as specified by its heavy and light chain combination of SEQ ID NO:45, SEQ ID NO:46, SEQ ID NO:47 (2×), and SEQ ID NO:48, and as shown in FIG. 2A and described in EP14179705. The terms "21-TCBcv, 22-TCBcv, 42-TCBcv" as used herein refer to the respective bispecific antibodies of Mab21, as specified by its heavy and light chain combination of SEQ ID NO:48, SEQ ID NO:49, SEQ ID NO:50, and SEQ ID NO:51 (2×), Mab 22 as specified by its heavy and light chain combinations of SEQ ID NO:48, SEQ ID NO:52, SEQ ID NO:53, and SEQ ID NO:54 (2×), and Mab42 as specified by its heavy and light chain combination of SEQ ID NO:48 of SEQ ID NO:55, SEQ ID NO:56, and SEQ ID NO:57-(2×).

B. Brief Description of the Figures

Figure 1B:
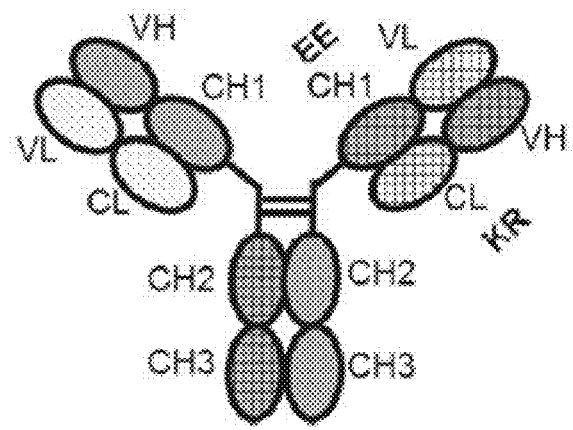

FIG. 1A and FIG. 1B. Bispecific bivalent antibodies comprising only the Fab fragments (specific to CD3 and BCMA) and the Fc part as specified: (FIG. 1A) Fab BCMA (RK/EE)-Fc-Fab CD3; (FIG. 1B) Fab BCMA-Fc-Fab CD3 (RK/EE). Amino acid substitutions for RK/EE introduced in CL-CH1 to reduce LC mispairing/side products in production. The Fab CD3 includes a VL-VH crossover to reduce LC mispairing and side-products.

FIG. 2A, FIG. 2B, FIG. 2C, and FIG. 2D. Preferred bispecific trivalent antibodies comprising only the Fab fragments (specific to CD3 and BCMA) and the Fc part as specified: (FIG. 2A) Fab BCMA(RK/EE)-Fc-Fab CD3-Fab BCMA(RK/EE); (FIG. 2B) Fab BCMA-Fc-Fab CD3(RK/EE)-Fab BCMA; (FIG. 2C) Fab BCMA(RK/EE)-Fc-Fab BCMA(RK/EE)-Fab CD3; (FIG. 2D) Fab BCMA-Fc-Fab BCMA-Fab CD3(RK/EE). Amino acid substitutions for RK/EE introduced in CL-CH1 to reduce LC mispairing/side-products in production. Preferably, the Fab CD3 includes a VL-VH crossover to reduce LC mispairing and side-products. Preferably, Fab CD3 and Fab BCMA are linked to each other with flexible linkers.

FIG. 3A, FIG. 3B, FIG. 3C, and FIG. 3D. Bispecific bivalent antibodies comprising only the Fab fragments (specific to CD3 and BCMA) and the Fc part as specified: (FIG. 3A) Fc-Fab CD3-Fab BCMA(RK/EE); (FIG. 3B) Fc-Fab CD3(RK/EE)-Fab BCMA; (FIG. 3C) Fc-Fab BCMA(RK/EE)-Fab CD3; (FIG. 3D) Fc-Fab BCMA-Fab CD3(RK/EE). Preferably, the Fabs CD3 include a VL-VH crossover to reduce LC mispairing and side-products. Fab CD3 and Fab BCMA are linked to each other with flexible linkers.

FIG. 4A, FIG. 4B, and FIG. 4C illustrate that pretreatment of effector T-cells or multiple myeloma (MM) or PCL target cells with Compound 2 enhances the potency and in some cell lines, also enhances the maximal target cell killing achieved with bispecific antibody specifically binding to human B cell maturation antigen (BCMA) and to human CD3ε (CD3), provided herein. Effector T-cells (CD3+) were pretreated with DMSO (control) or Compound 2 (1 nM) for 16 hours, then washed and used for co-cultures. The H929 (FIG. 4A), L363 (FIG. 4B) and OPM-2 (FIG. 4C) target cell lines were pretreated with DMSO (control) or Compound 2 (1 nM) for 72 hours, then washed and used for co-cultures at effector T-cell (E) to target cell (T) ratios of 1:3, 1:1 and 1:5, respectively. "DMSO-DMSO" lines: both target and effector cells pretreated with DMSO (controls). "Compound 2-DMSO" lines: target cells pretreated with Compound 2, effector cells pretreated with DMSO (control). "DMSO-Compound 2" lines: target cells pretreated with DMSO (control), effector cells pretreated with Compound 2. "Compound 2-Compound 2" lines: both target and effector cells pretreated with Compound 2. The y-axis represents the percentage of live tumors cells normalized to the number of live cells in the absence of bispecific antibody; the x-axis shows the log[concentration] of the bispecific antibody in pM.

Figure 5:
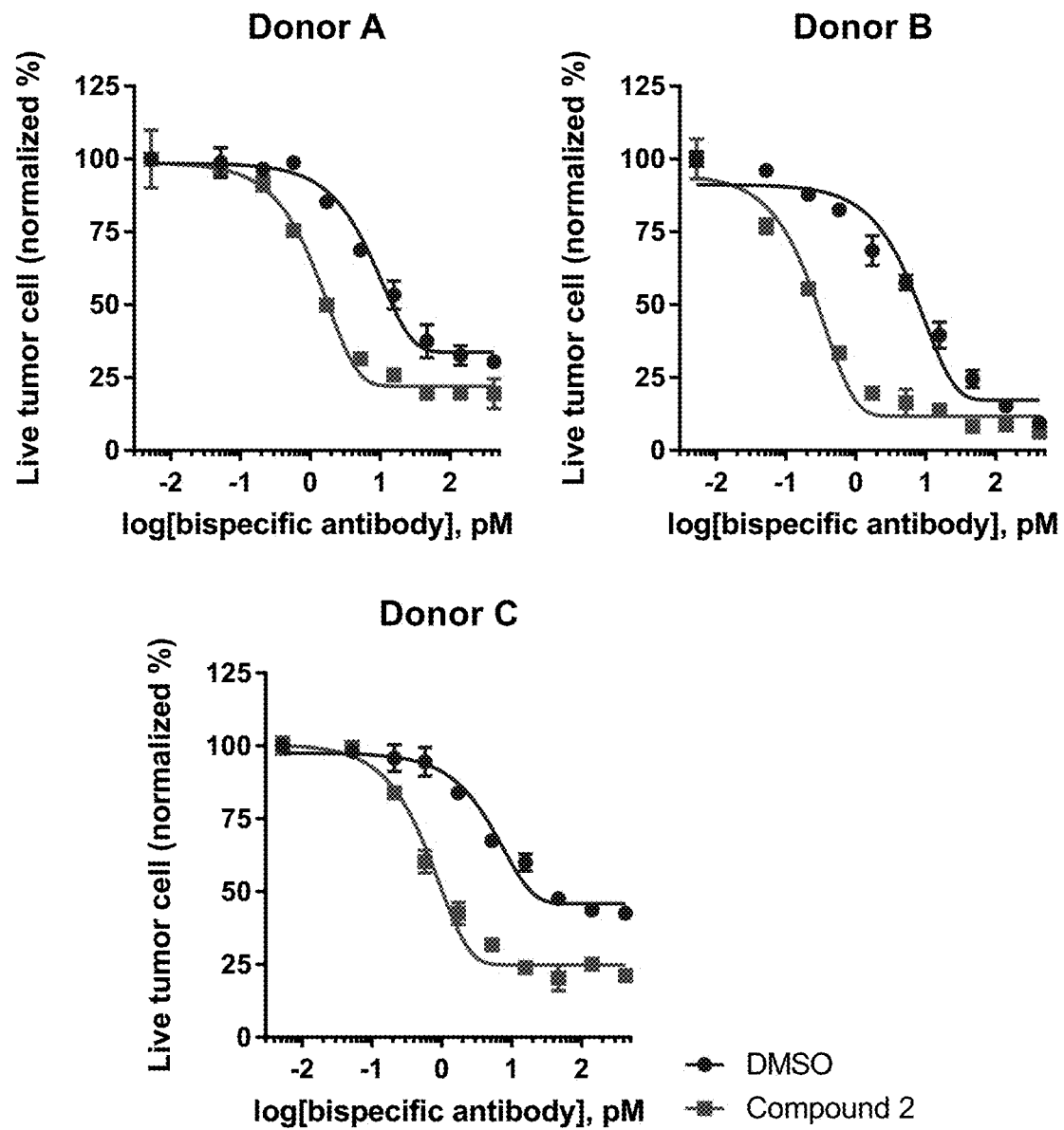

FIG. 5 illustrates that Compound 2 enhances the potency and maximal target cell killing achieved with bispecific antibody specifically binding to human B cell maturation antigen (BCMA) and to human CD3ε (CD3), provided herein. Effector T-cells (CD3+) from three different donors were co-cultured with MM target cell line H929 at fixed effector T-cell (E) to target cell (T) ratios of 1:3, in the presence of DMSO (control) or Compound 2 (1 nM) for 72 hours. The y-axis represents the percentage of live tumors cells normalized to the number of live cells in the absence of bispecific antibody; the x-axis shows the log[concentration] of the bispecific antibody in pM.

Figure 6:
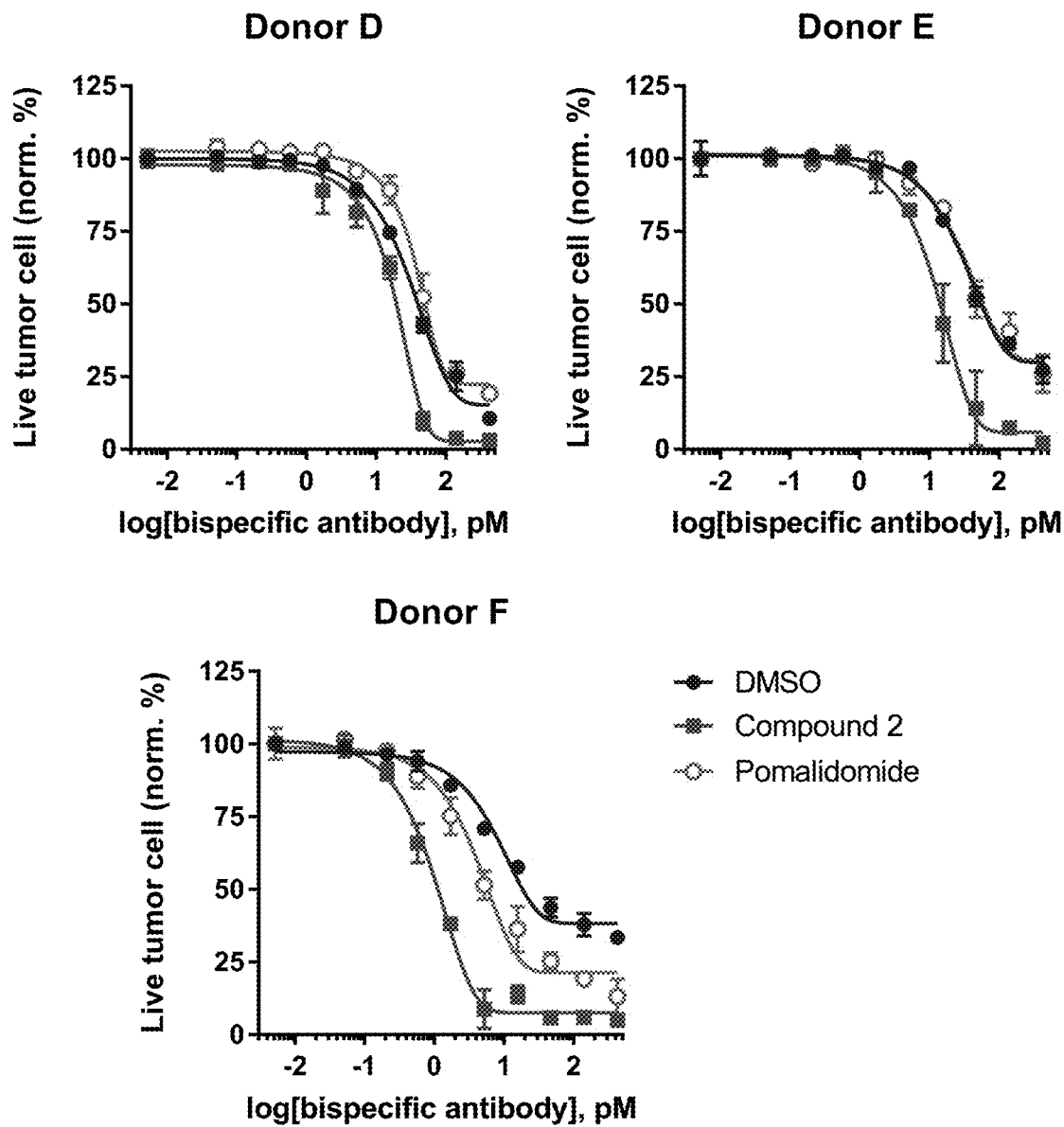

FIG. 6 illustrates that pretreatment of lenalidomide-resistant multiple myeloma cells with Compound 2, but not with pomalidomide, enhances the potency and maximal target cell killing achieved with bispecific antibody specifically binding to human B cell maturation antigen (BCMA) and to human CD3ε (CD3), provided herein. The H929-1051 target cell line was pretreated with DMSO (control), pomalidomide (100 nM) or Compound 2 (1 nM) for 72 hours, then washed and used for co-cultures at an effector T-cell (E) to target cell (T) ratio of 1:3. The y-axis represents the percentage of live tumors cells normalized to the number of live cells in the absence of bispecific antibody; the x-axis shows the log[concentration] of the bispecific antibody in pM.

C. Compounds

Provided for use in the methods herein is the compound 4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 1":

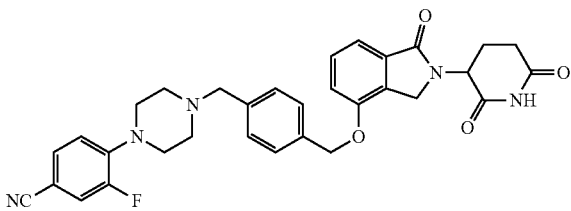

1 or an enantiomer or a mixture of enantiomers, tautomer, isotopolog or a pharmaceutically acceptable salt thereof.

Also provided for use in the methods herein is the compound (S)-4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 2":

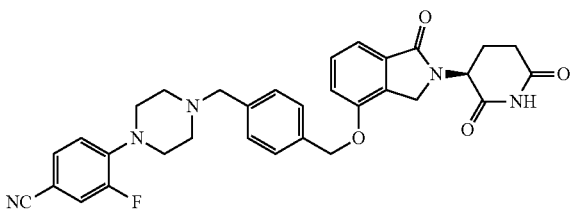

2 or a tautomer, isotopolog, or pharmaceutically acceptable salt thereof.

Also provided for use in the methods herein is the compound (R)-4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 3":

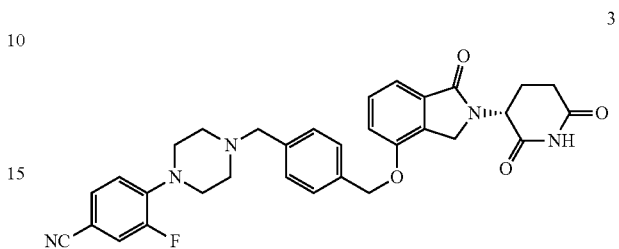

3 or a tautomer, isotopolog, or pharmaceutically acceptable salt thereof.

D. Preparation of Compound 1, Compound 2 and Compound 3

The compounds for use in the methods provided herein can be prepared by methods known to one of skill in the art and following procedures similar to those described in the Examples section herein and routine modifications thereof. An exemplary reaction scheme for the preparation of the compounds is illustrated below in Scheme 1 for Compound 1, Compound 2 and Compound 3, and Scheme 2 for Compound 2.

As shown in Scheme 1, protection of 3-hydroxy-2-methylbenzoic acid (by, for example, methyl ester and tert-butyl (dimethyl)silylether formation) was followed by bromination, for example using N-bromosuccinimide and azobisisobutyronitrile. Reaction with methyl-4,5-diamino-5-oxo-pentanoate, in the presence of a base (such as DIEA), resulted in derivatized isoindoline formation, which was followed by TBS deprotection using a base, such as potassium carbonate. Reaction of the derivatized isoindoline with 1,4-bis(bromomethyl)benzene in the presence of a base (such as potassium carbonate), was followed by glutarimide formation in the presence of potassium tert-butoxide. Finally, reaction with 3-fluoro-4-(piperazin-1-yl)benzonitrile afforded the target Compound 1. Chiral separation then affords Compound 2 and Compound 3.

Scheme 1

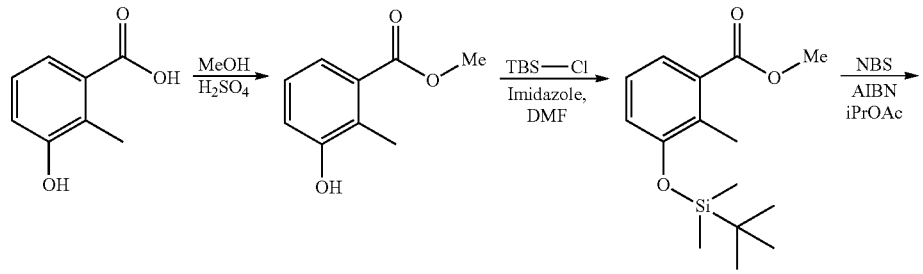

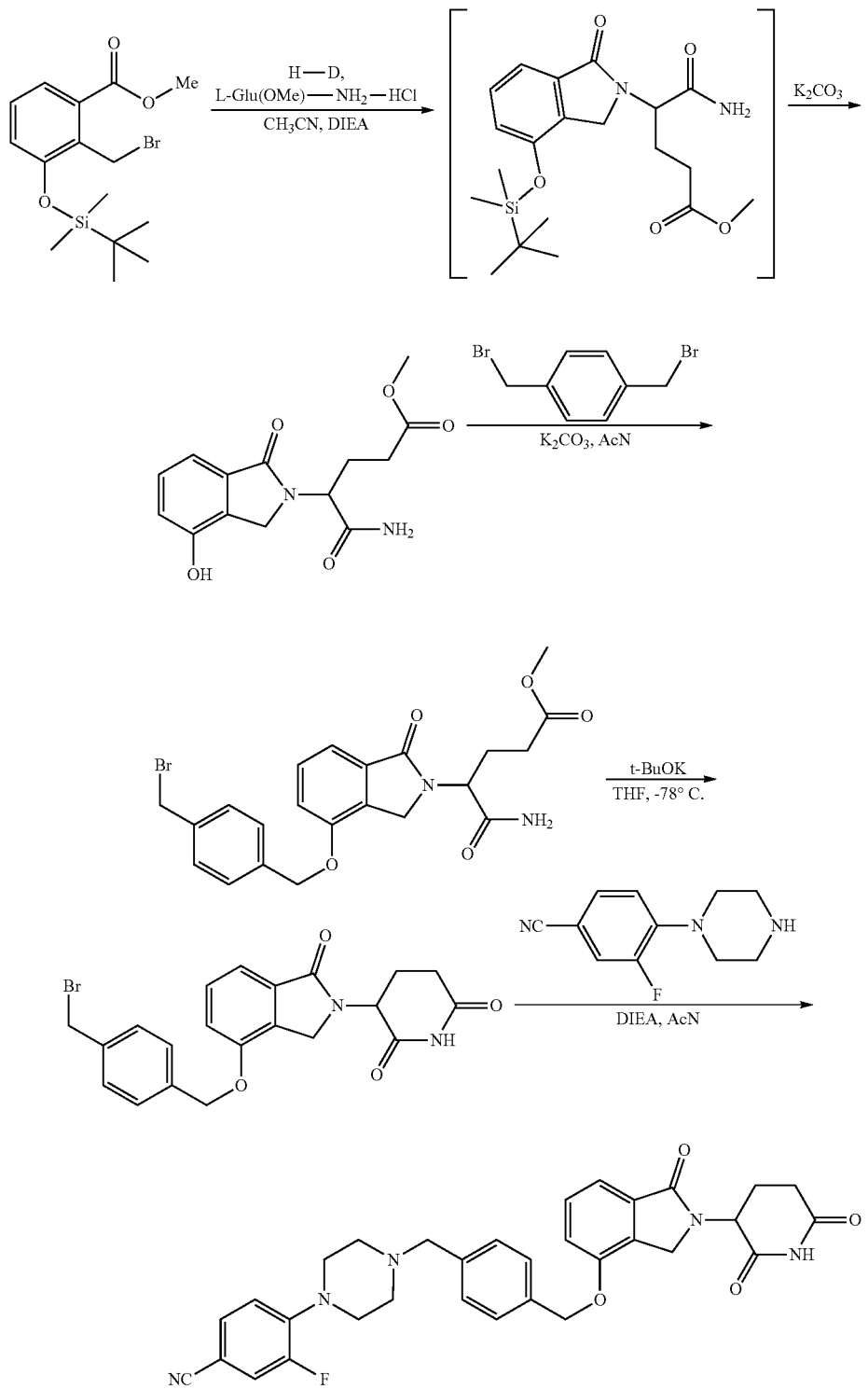

Alternatively as exemplified in Scheme 2, reaction of the methyl 2-(bromomethyl)-3-[tert-butyl(dimethyl)silyl]oxy-benzoate intermediate with the chiral tert-butyl (4S)-4,5-diamino-5-oxo-pentanoate, in the presence of a base (such as DIEA), resulted in derivatized isoindoline formation, which was followed by TBS deprotection using tetrabutylammonium fluoride. Reaction of the derivatized isoindoline with 4-(4-(4-(chloromethyl)benzyl)piperazin-1-yl)-3-fluorobenzonitrile in the presence of a base (such as potassium carbonate), followed by deprotection and glutarimide formation afforded the target Compound 2.

Scheme 2.
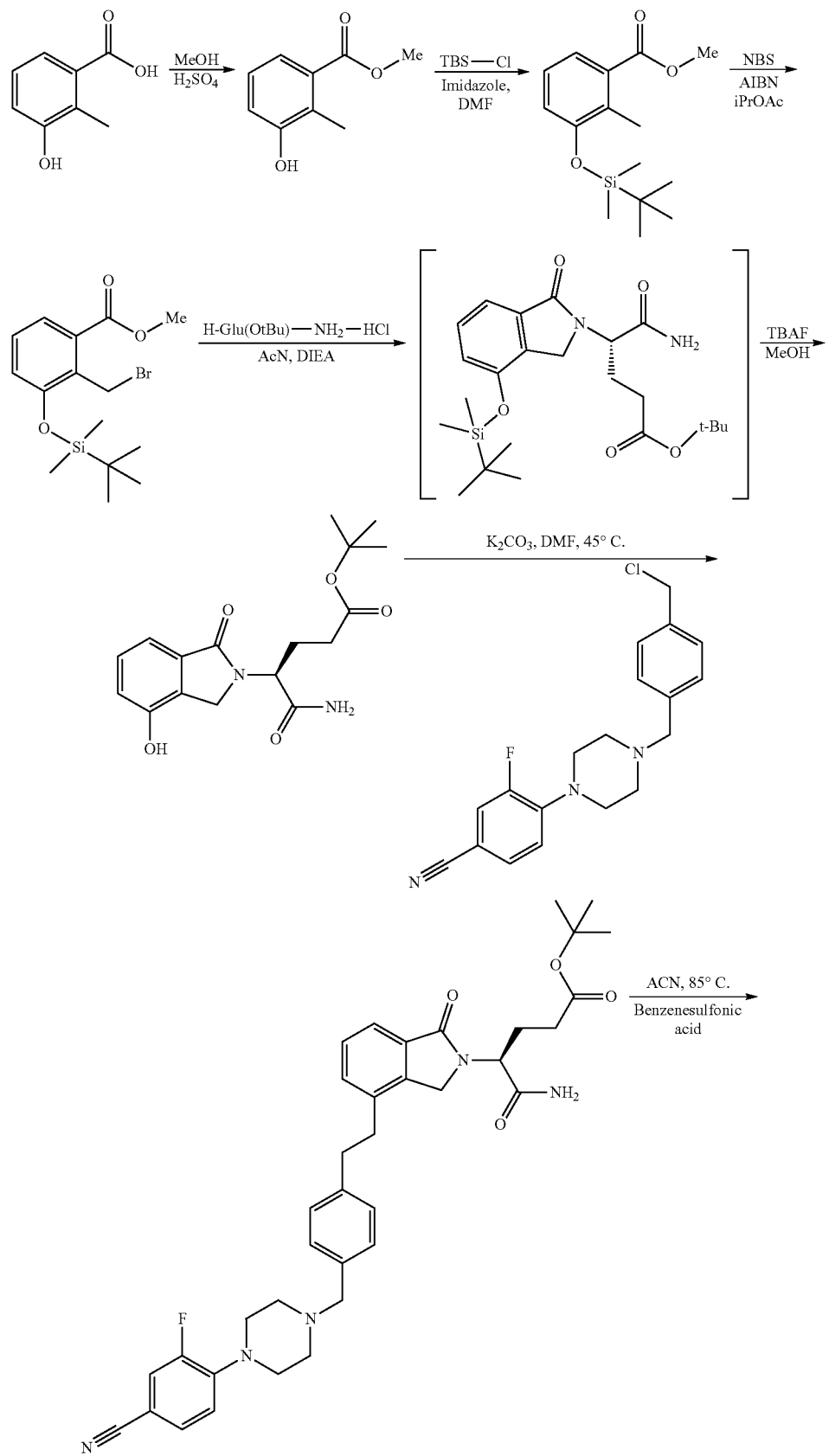

-continued

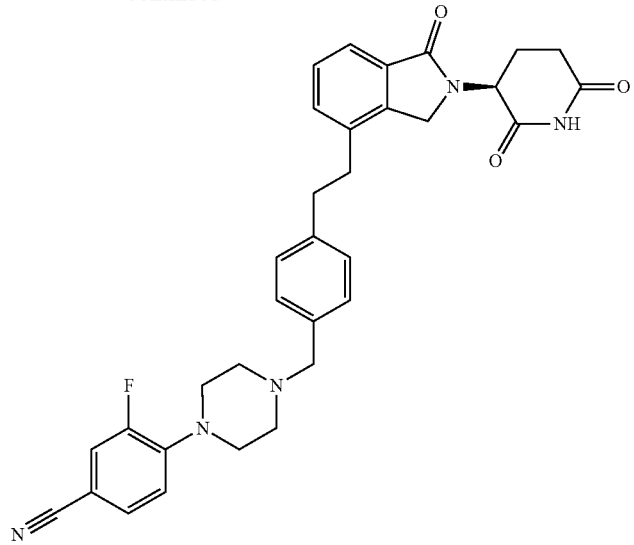 [SMILES: N#Cc1ccc(N2CCN(Cc3ccc(CCc4cccc5c4CN([C@H]4CCC(=O)NC4=O)C5=O)cc3)CC2)c(F)c1]

One skilled in the art would know how to modify the procedures set forth in the illustrative schemes and examples to arrive at the desired products.

E. Bispecific Antibody Specifically Binding to BCMA and to CD3

Provided for use in the methods herein is a bispecific antibody specifically binding to human B cell maturation antigen (BCMA) and to human CD3ε (CD3).

In one embodiment, the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  a) CDR1L region of SEQ ID NO:25 and CDR2L region of SEQ ID NO:26, or
  b) CDR1L region of SEQ ID NO:27 and CDR2L region of SEQ ID NO:28.

In one embodiment, the first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20, a CDR1L region of SEQ ID NO:23 and a CDR2L region of SEQ ID NO:24.

In one embodiment, the first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20, a CDR1L region of SEQ ID NO:25 and a CDR2L region of SEQ ID NO:26.

In one embodiment, the first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20, a CDR1L region of SEQ ID NO:27 and a CDR2L region of SEQ ID NO:28.

In one embodiment, the bispecific antibody comprises a first binding part specifically binding to human B cell maturation antigen (BCMA) and a second binding part specifically binding to human CD3ε (CD3), characterized in that the first binding part comprises a VH region of SEQ ID NO: 10 and a VL region of SEQ ID NO: 12, a VH region of SEQ ID NO: 10 and a VL region of SEQ ID NO: 13, or a VH region of SEQ ID NO: 10 and a VL region of SEQ ID NO: 14.

In on embodiment, the first binding part comprises a VH region of SEQ ID NO: 10 and a VL region of SEQ ID NO: 12.

In on embodiment, the first binding part comprises a VH region of SEQ ID NO: 10 and a VL region of SEQ ID NO: 13.

In on embodiment, the first binding part comprises a VH region of SEQ ID NO: 10 and a VL region of SEQ ID NO: 14.

In one embodiment, the first binding part is characterized in comprising a VL region selected from the group consisting of VL regions of SEQ ID NO:12, 13, and 14 wherein amino acid 49 is selected from the group of amino acids tyrosine (Y), glutamic acid (E), serine (S), and histidine (H). In one embodiment amino acid 49 is E within SEQ ID NO: 12, S within SEQ ID NO: 13 or H within SEQ ID NO: 14.

In one embodiment, the first binding part is characterized in comprising a VL region selected from the group consisting of VL regions of SEQ ID NO:12, 13, and 14 wherein amino acid 74 is threonine (T) or alanine (A). In one embodiment amino acid 74 is A within SEQ ID NO: 14.

In one embodiment, the first binding part is characterized in comprising as BCMA VH a VH region of SEQ ID NO: 10.

In one embodiment, the first binding part is characterized in comprising a VL region selected from the group consisting of VL regions of SEQ ID NO:12, 13, and 14 wherein amino acid 49 is selected from the group of amino acids tyrosine (Y), glutamic acid (E), serine (S), and histidine (H). In one embodiment amino acid 49 is E (SEQ ID NO:12), S (SEQ ID NO:13) or H (SEQ ID NO:14). In one embodiment of the invention the first binding part is characterized in comprising a VL region selected from the group consisting of VL regions of SEQ ID NO: 12, 13, and 14 wherein amino acid 74 is threonine (T) or alanine (A). In one embodiment amino acid 74 is A within SEQ ID NO:14.

In one embodiment, the first binding part is characterized in comprising a CDR3H region of SEQ ID NO: 17 and a CDR3L region of SEQ ID NO:20 and a CDR1H, CDR2H, CDR1L, and CDR2L region combination selected from the group of a) CDR1H region of SEQ ID NO:21 and CDR2H region of SEQ ID NO:22, CDR1L region of SEQ ID NO:23, and CDR2L region of SEQ ID NO:24, b) CDR1H region of SEQ ID NO:21 and CDR2H region of SEQ ID NO:22, CDR1L region of SEQ ID NO:25, and CDR2L region of SEQ ID NO:26,c) CDR1H region of SEQ ID NO:21 and CDR2H region of SEQ ID NO:22, CDR1L region of SEQ ID NO:27, and CDR2L region of SEQ ID NO:28,d) CDR1H region of SEQ ID NO:29 and CDR2H region of SEQ ID NO:30, CDR1L region of SEQ ID NO:31, and CDR2L region of SEQ ID NO:32,e) CDR1H region of SEQ ID NO:34 and CDR2H region of SEQ ID NO:35, CDR1L region of SEQ ID NO:31, and CDR2L region of SEQ ID NO:32, and f) CDR1H region of SEQ ID NO:36 and CDR2H region of SEQ ID NO:37, CDR1L region of SEQ ID NO:31, and CDR2L region of SEQ ID NO:32.

In one embodiment, the first binding part is characterized in comprising as VH region a VH region selected from the group consisting of SEQ ID NO:38, 39, and 40. In one embodiment of the invention the first binding part is characterized in that comprising as VH region a VH region of SEQ ID NO:38 and as VL region a VL region of SEQ ID NO: 12. In one embodiment of the invention the first binding part is characterized in that comprising as VH region a VH region of SEQ ID NO:39 and as VL region a VL region of SEQ ID NO: 12. In one embodiment of the invention the first binding part is characterized in that comprising as VH region a VH region of SEQ ID NO:40 and as VL region a VL region of SEQ ID NO: 12.

In one embodiment, the first binding part is characterized in comprising a CDR1H region of SEQ ID NO: 15, a CDR2H region of SEQ ID NO: 16, a CDR3H region of SEQ ID NO: 17, a CDR1L region of SEQ ID NO: 18, a CDR2L region of SEQ ID NO: 19 and a CDR3L region of SEQ ID NO: 20.

The first binding part according to the invention comprises as CDR3H and CDR3L regions the same CDR regions as antibody 83A10 (for antibody 83A10 see Table 1A and B later in the text).

In one embodiment, the first binding part is characterized in that comprising as VH region a VH region of SEQ ID NO:9 and as VL region a VL region of SEQ ID NO: 11.

In one embodiment, the bispecific antibody comprises not more than one Fab fragment of an anti-CD3 antibody portion, not more than two Fab fragments of an anti-BCMA antibody portion and not more than one Fc part, in one embodiment a human Fc part. In one embodiment not more than one Fab fragment of the anti-CD3 antibody portion and not more than one Fab fragment of the anti-BCMA antibody portion are linked to the Fc part and linking is performed via C-terminal binding of the Fab fragment(s) to the hinge region. In one embodiment a second Fab fragment of the anti-BCMA antibody portion is linked via its C-terminus either to the N-terminus of the Fab fragment of the anti-CD3 antibody portion or to the hinge region of the Fc part and therefore between the Fc part and the anti-CD3 antibody portion. The preferred bispecific antibodies are shown in FIGS. 1A, 1B, 2A to 2D, and 3A to 3D.

Especially preferred are bispecific antibodies comprising only the Fab fragments and the Fc part as specified, with or without "amino acid substitution": Fab BCMA-Fc-Fab CD3 (bispecific format FIG. 1A or FIG. 1B), Fab BCMA-Fc-Fab CD3-Fab BCMA (bispecific format FIG. 2A or FIG. 2B), Fab BCMA-Fc-Fab BCMA-Fab CD3 (bispecific format FIG. 2C or FIG. 2D), Fc-Fab CD3-Fab BCMA (bispecific format FIG. 3A or FIG. 3B), Fc-Fab BCMA-Fab CD3 (bispecific format FIG. 3C or FIG. 3D).

As shown in FIGS. 1A, 1B, 2A to 2D, and 3A to 3D "Fab BCMA-Fc, "Fab BCMA-Fc-Fab CD3" and "Fab BCMA-Fc-Fab CD3" means that the Fab fragment(s) is (are) bound via its (their) C-terminus to the N-terminus of the Fc fragment. "Fab CD3-Fab BCMA" means that the Fab CD3 fragment is bound with its N-terminus to the C-terminus of the Fab BCMA fragment. "Fab BCMA-Fab CD3" means that the Fab BCMA fragment is bound with its N-terminus to the C-terminus of the Fab CD3 fragment.

In one embodiment the bispecific antibody comprises a second Fab fragment of said anti-BCMA antibody linked with its C-terminus to the N-terminus of the CD3 antibody portion of said bispecific antibody. In one embodiment a VL domain of said first anti-CD3 antibody portion is linked to a CH1 or CL domain of said second anti-BCMA antibody.

In one embodiment the bispecific antibody comprises a second Fab fragment of said anti-BCMA antibody linked with its C-terminus to the Fc part (like the first Fab fragment of said anti-BCMA antibody) and linked with its N-terminus to the C-terminus of the CD3 antibody portion. In one embodiment a CH1 domain of said anti-CD3 antibody portion is linked to the VH domain of said second anti-BCMA antibody portion.

In one embodiment the bispecific antibody comprises an Fc part linked with its N-terminus to the C-terminus of said CD3 antibody Fab fragment. In one embodiment the bispecific antibody comprises an Fc part linked with its first N-terminus to the C-terminus of said CD3 antibody Fab fragment and a second Fab fragment of said anti-BCMA antibody linked with its C-terminus to the second N-terminus of the Fc part. In one embodiment the CL domain of the CD3 antibody Fab fragment is linked to the hinge region of the Fc part. In one embodiment the CH1 domain of the BCMA antibody Fab fragment is linked to the hinge region of the Fc part.

The Fab fragments are linked together by the use of an appropriate linker according to the state of the art. In one embodiment a (Gly4-Ser1)3 linker is used (Desplancq D K et al., Protein Eng. 1994 August; 7(8): 1027-33 and Mack M. et al., *PNAS* Jul. 18, 1995 vol. 92 no. 15 7021-7025). As the linker is a peptidic linker, such covalent binding is usually performed by biochemical recombinant means, using a nucleic acid encoding the VL and/or VH domains of the respective Fab fragments, the linker and if appropriate the Fc part chain.

In one embodiment the anti CD3ε antibody comprises a variable domain VH comprising the heavy chain CDRs of SEQ ID NO: 1, 2 and 3 as respectively heavy chain CDR1H, CDR2H and CDR3H and a variable domain VL comprising the light chain CDRs of SEQ ID NO: 4, 5 and 6 as respectively light chain CDR1L, CDR2L and CDR3L. In one embodiment the antibody comprises the variable domains of SEQ ID NO:7 (VH) and SEQ ID NO:8 (VL).

In one embodiment the bispecific antibody is characterized in that the variable domains of the anti CD3 antibody portion are of SEQ ID NO:7 and 8.

In one embodiment of the invention the bispecific antibody is characterized in that the anti-CD3 antibody portion (the second binding part of the bispecific antibody) is linked at its N-terminus to the C-terminus of a of the anti-BCMA antibody portion (the first binding part of the bispecific antibody) and the variable domains VL and VH of the anti-CD3 antibody portion or the constant domains CL and CH1 are replaced by each other.

In one embodiment the VH domain of said anti-CD3 antibody portion is linked to a CH1 or CL domain of said anti-BCMA antibody portion. In one embodiment a VL domain of said anti-CD3 antibody portion is linked to a CH1 or CL domain of said anti-BCMA antibody portion.

Such antibody portion is in one embodiment a Fab fragment of the respective antibody.

The bispecific antibody against BCMA and CD3 is characterized in one embodiment in comprising
a) a light chain and heavy chain of an antibody specifically binding to one of said targets CD3 and BCMA; and
b) a light chain and heavy chain of an antibody specifically binding to the other one of said targets, wherein the variable domains VL and VH or the constant domains CL and CH1 are replaced by each other.

In one embodiment a VH domain of said anti-CD3 antibody portion is linked to a CH1 or CL domain of said anti-BCMA antibody portion. In one embodiment a VL domain of said anti-CD3 antibody portion is linked to a CH1 or CL domain of said anti-BCMA antibody portion.

In a further embodiment, the bispecific antibody wherein the variable domains VL and VH in the light chain and the respective heavy chain of the anti-CD3 antibody portion or the anti-BCMA antibody portion are replaced by each other, is characterized in comprising a constant domain CL of the anti-CD3 antibody portion or the anti-BCMA antibody portion wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D). In one embodiment the antibody is monovalent for CD3 binding. In one embodiment, in addition to the amino acid replacement at position 124 in the constant domain CL the amino acid at position 123 is substituted independently by lysine (K), arginine (R) or histidine (H) (further called as "charge variant exchange"). In one embodiment the antibody is monovalent for CD3 binding and amino acid 124 is K, amino acid 147 is E, amino acid 213 is E, and amino acid 123 is R. In one embodiment the bispecific antibody comprises in addition the same anti-BCMA binding portion once more (in one embodiment a Fab fragment). That means also, that if the first anti-BCMA binding portion comprises the charge variant exchange, then the second anti-BCMA binding portion comprise the same charge variant exchange. (All amino acid numbering is according to Kabat).

In one embodiment, the bispecific antibody is characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and
c) wherein in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to Kabat) (see e.g. FIGS. 1A, 2A, 2C, 3A, 3C).

Figures 2C, 2D:
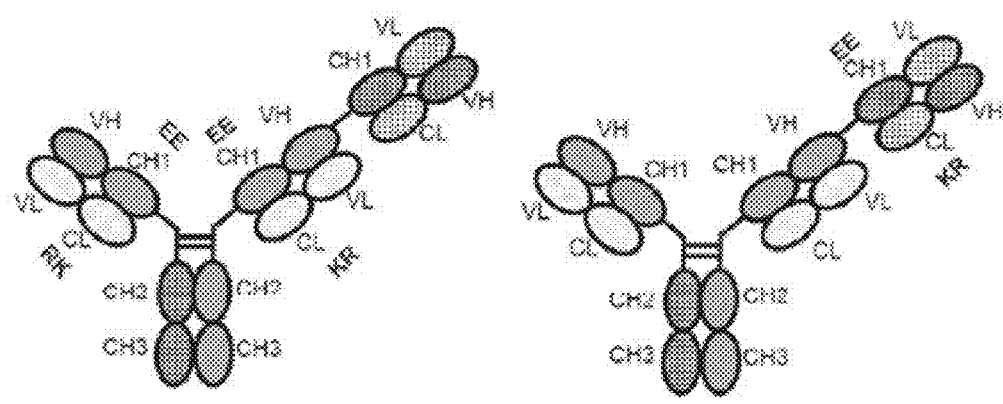
Figure 3A:
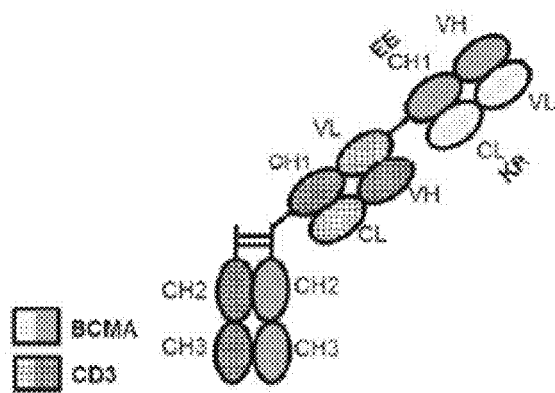
Figure 3B:
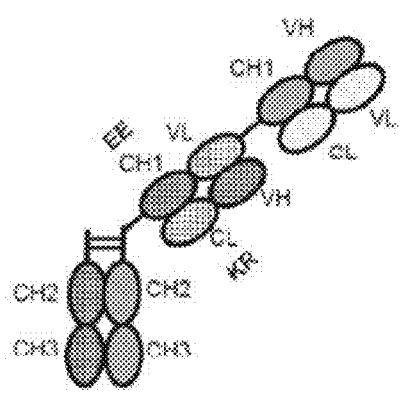
Figure 3C:
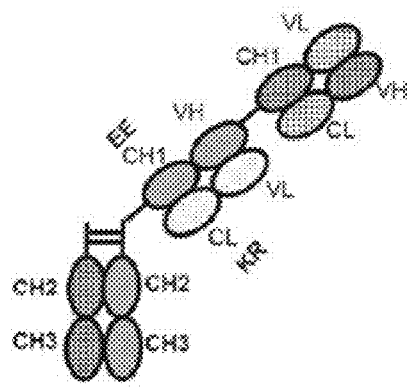
Figure 3D:
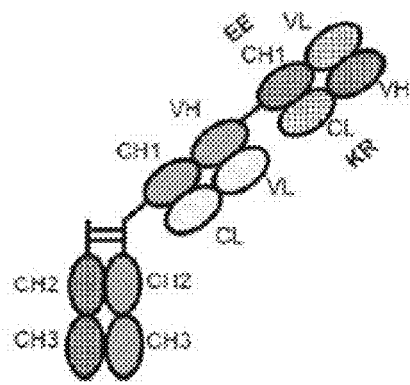

In one embodiment, said bispecific antibody described in the last preceding paragraph is further characterized in that said bispecific antibody comprises in addition a Fab fragment of said first antibody (further named also as "BCMA-Fab") and in the constant domain CL said BCMA-Fab the amino acid at position 124 is substituted independently by lysine (K), arginine (R) or histidine (H) (numbering according to Kabat), and wherein in the constant domain CH1 of said BCMA-Fab the amino acid at positions 147 and the amino acid at position 213 is substituted independently by glutamic acid (E), or aspartic acid (D) (numbering according to Kabat) (see e.g. FIGS. 2A, 2C).

In one embodiment of the invention the bispecific antibody consists of one CD3-Fab, and one BCMA-Fab and a Fc part, wherein the CD3-Fab and the BCMA-Fab are linked via their C-termini to the hinge region of said Fc part and a second BCMA-Fab, which is linked with its C-terminus to the N-terminus of the CD3-Fab. The CD3-Fab comprises crossover and either the CD3-Fab or both BCMA-Fabs comprise amino acid substitution (FIGS. 2A and 2B). Especially preferred is a bispecific antibody comprising BCMA-Fab-Fc-CD3-Fab-BCMA-Fab, wherein both BCMA-Fabs comprise amino acid substitution and the CD3-Fab comprises VL/VH crossover (FIG. 2A). Especially preferred is a bispecific antibody consisting of BCMA-Fab-Fc-CD3-Fab-BCMA-Fab, wherein both BCMA-Fabs comprise amino acid substitution Q124K, E123R, K147E and K213E and the CD3-Fab comprises VL/VH crossover. Especially preferred is that both BCMA-Fabs comprise as CDRs the CDRs of antibody 21, 22, or 42, or as VH/VL the VH/VL of antibody 21, 22, or 42 (for antibodies 21, 22 and 42 see Table 1A and B later in the text).

The first and a second Fab fragment of an antibody specifically binding to BCMA are in one embodiment derived from the same antibody and in one embodiment identical in the CDR sequences, variable domain sequences VH and VL and/or the constant domain sequences CH1 and CL. In one embodiment the amino acid sequences of the first and a second Fab fragment of an antibody specifically binding to BCMA are identical. In one embodiment the BCMA antibody is an antibody comprising the CDR sequences of antibody 21, 22, or 42, an antibody comprising the VH and VL sequences of antibody 21, 22, or 42, or an antibody comprising the VH, VL, CH1, and CL sequences of antibody 21, 22, or 42.

In one embodiment, the bispecific antibody is characterized in comprising a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to Kabat).

In one embodiment, in addition to the amino acid replacement at position 124 in the constant domain CL of the first or second light chain the amino acid at position 123 is substituted independently by lysine (K), arginine (R) or histidine (H).

In one embodiment in the constant domain CL the amino acid at position 124 is substituted by lysine (K), in the constant domain CH1 the amino acid at position 147 and the amino acid at position 213 are substituted by glutamic acid (E). In one embodiment in addition in the constant domain CL in the amino acid at position 123 is substituted by arginine (R).

In one embodiment, the bispecific antibody consists of two BCMA-Fabs and an Fc part, wherein one BCMA-Fab and the CD3 Fab are linked via their C-termini to the hinge region of said Fc part and the second BCMA-Fab is linked with its C-terminus to the N-terminus of the CD3-Fab. The CD3-Fab comprises crossover and either the CD3-Fab or both BCMA-Fabs comprise amino acid substitution (FIGS. 2A and 2B).

In one embodiment, the bispecific antibody is characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:
a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

In one embodiment, the bispecific antibody is characterized in that said amino acid residue having a larger side chain volume is selected from the group consisting of arginine (R), phenylalanine (F), tyrosine (Y), tryptophan (W).

In one embodiment, the bispecific antibody is characterized in that said amino acid residue having a smaller side chain volume is selected from the group consisting of alanine (A), serine (S), threonine (T), valine (V).

In one embodiment such a bispecific antibody is characterized in that both CH3 domains are further altered by the introduction of cysteine (C) as amino acid in the corresponding positions of each CH3 domain.

In one embodiment such a bispecific antibody is characterized in that one of the constant heavy chain domains CH3 of both heavy chains is replaced by a constant heavy chain domain CH1; and the other constant heavy chain domain CH3 is replaced by a constant light chain domain CL.

In one embodiment the bispecific antibody comprises a modified Fc part inducing cell death of 20% or more cells of a preparation of BCMA expressing cells after 24 hours at a concentration of said antibody of 100 nM by ADCC relative to a control under identical conditions using the same antibody with the parent Fc part as control. Such an antibody is in one embodiment a naked antibody.

In one embodiment the bispecific antibody is an antibody with an amount of fucose of 60% or less of the total amount of oligosaccharides (sugars) at Asn297 (see e.g. US20120315268)

In one embodiment the Fc part comprises the amino acid substitutions which are introduced in a human Fc part and disclosed in SEQ ID NO:55 and 56.

In one embodiment the anti-BCMA antibody is Mab21, Mab22, Mab42, Mab27, Mab33, and Mab39 (for antibodies Mab 21, 22, 42, 27, 33, 39 see Tables 1A and B later in the text) as described herein by their CDR sequences, and/or VH/VL sequences together with the described CL and CH1 sequences. In one embodiment the bispecific antibody comprises an Fc part or not, especially the 2+1 format, and the heavy and light chains of the bispecific antibody is especially as described in Table 1A.

The anti-BCMA antibody depletes, in the bispecific format, especially in the 2+1 format, human malignant plasma cells in MM bone marrow aspirates to at least 80% after a 48 hour treatment in a concentration of between 10 nM and 1 fM inclusively. The anti-BCMA antibodies have been characterized in panning a variable heavy chain (VH) and a variable light chain (VL) phage-display library of antibody 83A10 (VH library, VL library) with 1-50 nM cyno BCMA in 1-3 rounds and selecting a variable light chain and a variable heavy chain which have such properties as such bispecific T cell binder. Preferably panning is performed in 3 rounds, using 50 nM cynoBCMA for round 1, 25 nM cyBCMA for round 2, and 10 nM cyBCMA for round 3. Preferably the libraries are randomized in either the light chain CDR1 and CDR2 or the heavy chain CDR1 and CDR2. Preferably a light and heavy chain are identified which each bind as Fab fragment, comprising in addition the corresponding VH or VL of antibody 83A10, to huBCMA with a Kd of 50 pM to 5 nM and to cyno BCMA with a Kd of 0.1 nM to 20 nM. Preferably the bispecific format is the format of FIG. 2A, comprising the respective constant domains VL and VH of the CD3 Fab replacement by each other and within both BCMA Fabs amino acid exchanges K213E and K147E in the CH1 domain and amino acid exchanges E123R and Q124K in the CL domain.

The bispecific antibody as mentioned herein can be prepared by the steps of transforming a host cell with vectors comprising nucleic acid molecules encoding the light chain and heavy chain of said antibody molecule, culturing the host cell under conditions that allow synthesis of said antibody molecule; and recovering said antibody molecule from said culture.

The bispecific antibody as mentioned herein can be prepared by the steps of transforming a host cell with vectors comprising nucleic acid molecules encoding the light chain and heavy chain of an antibody specifically binding to the first target vectors comprising nucleic acid molecules encoding the light chain and heavy chain of an antibody specifically binding to the second target, wherein the variable domains VL and VH or the constant domains CL and CH1 are replaced by each other; culturing the host cell under conditions that allow synthesis of said antibody molecule; and recovering said antibody molecule from said culture.

In one embodiment, the bispecific antibody is specifically binding to the extracellular domain of human BCMA and to human CD3e, characterized in comprising a heavy and light chain set selected from the group consisting of polypeptides
 i) SEQ ID NO:48, SEQ ID NO:49, SEQ ID NO:50, and SEQ ID NO:51(2×) (set 1 TCB of antibody 21),
 ii) SEQ ID NO:48, SEQ ID NO:52, SEQ ID NO:53, and SEQ ID NO:54 (2×) (set 2 TCB of antibody 22), and
 iii) SEQ ID NO:48, SEQ ID NO:55, SEQ ID NO:56, and SEQ ID NO:57(2×) (set 3 TCB of antibody 42).

In one embodiment, the bispecific antibody is specifically binding to the extracellular domain of human BCMA and to human CD3e, characterized in comprising a heavy and light chain set selected from the group consisting of polypeptides SEQ ID NO:48, SEQ ID NO:49, SEQ ID NO:50, and SEQ ID NO:51(2×) (set 1 TCB of antibody 21).

In one embodiment, the bispecific antibody is specifically binding to the extracellular domain of human BCMA and to human CD3e, characterized in comprising a heavy and light chain set selected from the group consisting of polypeptides SEQ ID NO:48, SEQ ID NO:52, SEQ ID NO:53, and SEQ ID NO:54 (2×) (set 2 TCB of antibody 22).

In one embodiment, the bispecific antibody is specifically binding to the extracellular domain of human BCMA and to human CD3e, characterized in comprising a heavy and light chain set selected from the group consisting of polypeptides SEQ ID NO:48, SEQ ID NO:55, SEQ ID NO:56, and SEQ ID NO:57(2×) (set 3 TCB of antibody 42).

TABLE 1A

Antibody sequences

| SEQ ID NO: | Name(s) | Amino acid sequences |
|---|---|---|
| 1 | CD3 CDR1H | TYAMN |
| 2 | CD3 CDR2H | RIRSKYNNYATYYADSVKG |
| 3 | CD3 CDR3H | HGNFGNSYVSWFAY |
| 4 | CD3 CDR1L | GSSTGAVTTSNYAN |
| 5 | CD3 CDR2L | GTNKRAP |
| 6 | CD3 CDR3L | ALWYSNLWV |
| 7 | CD3 VH | EVQLLESGGGLVQPGGSLRLSCAASGFTFSTYAMNWVR QAPGKGLEWVSRIRSKYNNYATYYADSVKGRFTISRDD SKNTLYLQMNSLRAEDTAVYYCVRHGNFGNSYVSWFA YWGQGTLVTVSS |
| 8 | CD3 VL | QAVVTQEPSLTVSPGGTVTLTCGSSTGAVTTSNYANWV QEKPGQAFRGLIGGTNKRAPGTPARFSGSLLGGKAALT LSGAQPEDEAEYYCALWYSNLWVFGGGTKLTVL |
| 9 | 83A10 VH | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCAKVLGWFDYWGQGTLV TVSS |
| 10 | Mab21 VH Mab22 Mab42 VH | EVQLLESGGGLVQPGGSLRLSCAASGFTFSDNAMGWV VHRQAPGKGLEWVSAISGPGSSTYYADSVKGRFTISRDNSK NTLYLQMNSLRAEDTAVYYCAKVLGWFDYWGQGTLV TVSS |
| 11 | 83A10 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGYPPDFTFGQGTKVEIK |
| 12 | Mab21 VL Mab27 VL Mab33 VL Mab39 VL | EIVLTQSPGTLSLSPGERATLSCRASQSVSEYYLAWYQQ KPGQAPRLLIEHASTRATGIPDRFSGSGSGTDFTLTISRLE PEDFAVYYCQQYGYPPDFTFGQGTKVEIK |
| 13 | Mab22 VL | EIVLTQSPGTLSLSPGERATLSCRASQSVSSYYLAWYQQ KPGQAPRLLISGAGSRATGIPDRFSGSGSGTDFTLTISRLE PEDFAVYYCQQYGYPPDFTFGQGTKVEIK |
| 14 | Mab42 VL | EIVLTQSPGTLSLSPGERATLSCRASQSVSDEYLSWYQQ KPGQAPRLLIHSASTRATGIPDRFSGSGSGTDFTLAISRLE PEDFAVYYCQQYGYPPDFTFGQGTKVEIK |

TABLE 1A-continued

Antibody sequences

| SEQ ID NO: | Name(s) | Amino acid sequences |
|---|---|---|
| 15 | 83A10 CDR1H | SYAMS |
| 16 | 83A10 CDR2H | AISGSGGSTYYADSVKG |
| 17 | 83A10 CDR3H<br>Mab21 CDR3H<br>Mab22 CDR3H<br>Mab42 CDR3H<br>Mab27 CDR3H<br>Mab33 CDR3H<br>Mab39 CDR3H | VLGWFDY |
| 18 | 83A10 CDR1L | RASQSVSSSYLAW |
| 19 | 83A10 CDR2L | YGASSRAT |
| 20 | 83A10 CDR3L<br>Mab21 CDR3L<br>Mab22 CDR3L<br>Mab42 CDR3L | QQYGYPPDFT |
| 21 | Mab21 CDR1H<br>Mab22 CDR1H<br>Mab42 CDR1H | DNAMG |
| 22 | Mab21 CDR2H<br>Mab22 CDR2H<br>Mab42 CDR2H | AISGPGSSTYYADSVKG |
| 23 | Mab21 CDR1L | RASQSVSEYYLAW |
| 24 | Mab21 CDR2L | EHASTRAT |
| 25 | Mab22 CDR1L | RASQSVSSYYLAW |
| 26 | Mab22 CDR2L | SGAGSRAT |
| 27 | Mab42 CDR1L | RASQSVSDEYLSW |
| 28 | Mab42 CDR2L | HSASTRAT |
| 29 | Mab27 CDR1H | SAPMG |
| 30 | Mab27 CDR2H | AISYIGHTYYADSVKG |
| 31 | Mab27 CDR1L<br>Mab33 CDR1L<br>Mab39 CDR1L | RASQSVSEYYLA |
| 32 | Mab27 CDR2L<br>Mab33 CDR2L<br>Mab39 CDR2L | HASTRAT |
| 33 | Mab27 CDR3L<br>Mab33 CDR3L<br>Mab39 CDR3L | QQYGYPPDFT |
| 34 | Mab33 CDR1H | TNAMG |
| 35 | Mab33 CDR2H | AINRFGGSTYYADSVKG |
| 36 | Mab39 CDR1H | QNAMG |
| 37 | Mab39 CDR2H | AISPTGFSTYYADSVKG |
| 38 | Mab27 VH | EVQLLESGGGLVQPGGSLRLSCAASGFTFSSAPMGWVR<br>QAPGKGLEWVSAISYIGHTYYADSVKGRFTISRDNSKNT<br>LYLQMNSLRAEDTAVYYCAKVLGWFDYWGQGTLVTV<br>SS |
| 39 | Mab33 VH | EVQLLESGGGLVQPGGSLRLSCAASGFTFYTNAMGWV<br>RQAPGKGLEWVSAINRFGGSTYYADSVKGRFTISRDNS<br>KNTLYLQMNSLRAEDTAVYYCAKVLGWFDYWGQGTL<br>VTVSS |

TABLE 1A-continued

Antibody sequences

| SEQ ID NO: | Name(s) | Amino acid sequences |
|---|---|---|
| 40 | Mab39 VH | EVQLLESGGGLVQPGGSLRLSCAASGFTFTQNAMGWV RQAPGKGLEWVSAISPTGFSTYYADSVKGRFTISRDNSK NTLYLQMNSLRAEDTAVYYCAKVLGWFDYWGQGTLV TVSS |
| 41 | 83A10 BCMA CH1<br>Mab21 BCMA CH1<br>Mab22 BCMA CH1<br>Mab42 BCMA CH1 | ASTKGPSVFPLAPSSKSTSGGTAALGCLVEDYFPEPVTV SWNSGALTSGVHTFPAVLQSSGLYSLSSVVTVPSSSLGT QTYICNVNHKPSNTKVDEKVEPKSC |
| 42 | 83A10 BCMA CL<br>Mab21 BCMA CL<br>Mab22 BCMA CL<br>Mab42 BCMA CL | RTVAAPSVFIFPPSDRKLKSGTASVVCLLNNFYPREAKV QWKVDNALQSGNSQESVTEQDSKDSTYSLSSTLTLSKA DYEKHKVYACEVTHQGLSSPVTKSFNRGEC |
| 43 | CD3 CH1 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| 44 | CD3 CL | ASVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC |
| 45 | 83A10 knob HC | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDGGGSGGG GSQAVVTQEPSLTVSPGGTVTLTCGSSTGAVTTSNYAN WVQEKPGQAFRGLIGGTNKRAPGTPARFSGSLLGGKAA LTLSGAQPEDEAEYYCALWYSNLWVFGGGTKLTVLSS ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALGAPIEKTISKAKGQPREPQ VYTLPPCRDELTKNQVSLWCLVKGFYPSDIAVEWESNG QPENNYKTTPPVLDSDGSFFLYSKLTVDKSRWQQGNVF SCSVMHEALHNHYTQKSLSLSPGK |
| 46 | 83A10 hole HC | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDKTHTCPPCP APEAAGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALGAPIEKTISKAKGQPR EPQVCTLPPSRDELTKNQVSLSCAVKGFYPSDIAVEWES NGQPENNYKTTPPVLDSDGSFFLVSKLTVDKSRWQQGN VFSCSVMHEALHNHYTQKSLSLSPGK |
| 47 | 83A10 LC | EIVLTQSPGTLSLSPGERATLSCRASQSVSSSYLAWYQQ KPGQAPRLLIYGASSRATGIPDRFSGSGSGTDFTLTISRLE PEDFAVYYCQQYGYPPDFTFGQGTKVEIKRTVAAPSVFI FPPSDRKLKSGTASVVCLLNNFYPREAKVQWKVDNAL QSGNSQESVTEQDSKDSTYSLSSTLTLSKADYEKHKVY ACEVTHQGLSSPVTKSFNRGEC |
| 48 | CD3 LC | EVQLLESGGGLVQPGGSLRLSCAASGFTFSTYAMNWVR QAPGKGLEWVSRIRSKYNNYATYYADSVKGRFTISRDD SKNTLYLQMNSLRAEDTAVYYCVRHGNFGNSYVSWFA YWGQGTLVTVSSASVAAPSVFIFPPSDEQLKSGTASVVC LLNNFYPREAKVQWKVDNALQSGNSQESVTEQDSKDS TYSLSSTLTLSKADYEKHKVYACEVTHQGLSSPVTKSFN RGEC |
| 49 | Mab21 knob HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS |

TABLE 1A-continued

Antibody sequences

| SEQ ID NO: | Name(s) | Amino acid sequences |
|---|---|---|
| | | LGTQTYICNVNHKPSNTKVDEKVEPKSCDGGGGSGGG<br>GSQAVVTQEPSLTVSPGGTVTLTCGSSTGAVTTSNYAN<br>WVQEKPGQAFRGLIGGTNKRAPGTPARFSGSLLGGKAA<br>LTLSGAQPEDEAEYYCALWYSNLWVFGGGTKLTVLSS<br>ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSCDKTHTCPPCPAPE<br>AAGGPSVFLFPPKPKDTLMISRTPEVTCVVVDVSHEDPE<br>VKFNWYVDGVEVHNAKTKPREEQYNSTYRVVSVLTVL<br>HQDWLNGKEYKCKVSNKALGAPIEKTISKAKGQPREPQ<br>VYTLPPCRDELTKNQVSLWCLVKGFYPSDIAVEWESNG<br>QPENNYKTTPPVLDSDGSFFLYSKLTVDKSRWQQGNVF<br>SCSVMHEALHNHYTQKSLSLSPGK |
| 50 | Mab21 hole HC | EVQLLESGGGLVQPGGSLRLSCAASGFTFSDNAMGWV<br>RQAPGKGLEWVSAISGPGSSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDKTHTCPPCP<br>APEAAGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALGAPIEKTISKAKGQPR<br>EPQVCTLPPSRDELTKNQVSLSCAVKGFYPSDIAVEWES<br>NGQPENNYKTTPPVLDSDGSFFLVSKLTVDKSRWQQGN<br>VFSCSVMHEALHNHYTQKSLSLSPGK |
| 51 | Mab21 LC | EIVLTQSPGTLSLSPGERATLSCRASQSVSEYYLAWYQQ<br>KPGQAPRLLIEHASTRATGIPDRFSGSGSGTDFTLTISRLE<br>PEDFAVYYCQQYGYPPDFTFGQGTKVEIKRTVAAPSVFI<br>FPPSDRKLKSGTASVVCLLNNFYPREAKVQWKVDNAL<br>QSGNSQESVTEQDSKDSTYSLSSTLTLSKADYEKHKVY<br>ACEVTHQGLSSPVTKSFNRGEC |
| 52 | Mab22 knob HC | EVQLLESGGGLVQPGGSLRLSCAASGFTFSDNAMGWV<br>RQAPGKGLEWVSAISGPGSSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDGGGGSGGG<br>GSQAVVTQEPSLTVSPGGTVTLTCGSSTGAVTTSNYAN<br>WVQEKPGQAFRGLIGGTNKRAPGTPARFSGSLLGGKAA<br>LTLSGAQPEDEAEYYCALWYSNLWVFGGGTKLTVLSS<br>ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSCDKTHTCPPCPAPE<br>AAGGPSVFLFPPKPKDTLMISRTPEVTCVVVDVSHEDPE<br>VKFNWYVDGVEVHNAKTKPREEQYNSTYRVVSVLTVL<br>HQDWLNGKEYKCKVSNKALGAPIEKTISKAKGQPREPQ<br>VYTLPPCRDELTKNQVSLWCLVKGFYPSDIAVEWESNG<br>QPENNYKTTPPVLDSDGSFFLYSKLTVDKSRWQQGNVF<br>SCSVMHEALHNHYTQKSLSLSPGK |
| 53 | Mab22 hole HC | EVQLLESGGGLVQPGGSLRLSCAASGFTFSDNAMGWV<br>RQAPGKGLEWVSAISGPGSSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDKTHTCPPCP<br>APEAAGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALGAPIEKTISKAKGQPR<br>EPQVCTLPPSRDELTKNQVSLSCAVKGFYPSDIAVEWES<br>NGQPENNYKTTPPVLDSDGSFFLVSKLTVDKSRWQQGN<br>VFSCSVMHEALHNHYTQKSLSLSPGK |
| 54 | Mab22 LC | EIVLTQSPGTLSLSPGERATLSCRASQSVSSYYLAWYQQ<br>KPGQAPRLLISGAGSRATGIPDRFSGSGSGTDFTLTISRLE<br>PEDFAVYYCQQYGYPPDFTFGQGTKVEIKRTVAAPSVFI<br>FPPSDRKLKSGTASVVCLLNNFYPREAKVQWKVDNAL<br>QSGNSQESVTEQDSKDSTYSLSSTLTLSKADYEKHKVY<br>ACEVTHQGLSSPVTKSFNRGEC |

TABLE 1A-continued

Antibody sequences

| SEQ ID NO: | Name(s) | Amino acid sequences |
|---|---|---|
| 55 | Mab42 knob HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDGGGGSGGG GSQAVVTQEPSLTVSPGGTVTLTCGSSTGAVTTSNYAN WVQEKPGQAFRGLIGGTNKRAPGTPARFSGSLLGGKAA LTLSGAQPEDEAEYYCALWYSNLWVFGGGTKLTVLSS ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALGAPIEKTISKAKGQPREPQ VYTLPPCRDELTKNQVSLWCLVKGFYPSDIAVEWESNG QPENNYKTTPPVLDSDGSFFLYSKLTVDKSRWQQGNVF SCSVMHEALHNHYTQKSLSLSPGK |
| 56 | Mab42 hole HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDKTHTCPPCP APEAAGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALGAPIEKTISKAKGQPR EPQVCTLPPSRDELTKNQVSLSCAVKGFYPSDIAVEWES NGQPENNYKTTPPVLDSDGSFFLVSKLTVDKSRWQQGN VFSCSVMHEALHNHYTQKSLSLSPGK |
| 57 | Mab42 LC | EIVLTQSPGTLSLSPGERATLSCRASQSVSDEYLSWYQQ KPGQAPRLLIHSASTRATGIPDRFSGSGSGTDFTLAISRLE PEDFAVYYCQQYGYPPDFTFGQGTKVEIKRTVAAPSVFI FPPSDRKLKSGTASVVCLLNNFYPREAKVQWKVDNAL QSGNSQESVTEQDSKDSTYSLSSTLTLSKADYEKHKVY ACEVTHQGLSSPVTKSFNRGEC |

Remark: SEQ ID NO: 20 and SEQ ID NO: 33 are identical

TABLE 1B

Antibody sequences (short list)

| | SEQ ID NO: | | | | | | |
|---|---|---|---|---|---|---|---|
| CD3 antibody | | | | | | | |
| VH | VL | CDR1H | CDR2H | CDR3H | CDR1L | CDR2L | CDR3L |
| 7 | 8 | 1 | 2 | 3 | 4 | 5 | 6 |

BCMA antibody

| | VH | VL | CDR1H | CDR2H | CDR3H | CDR1L | CDR2L | CDR3L |
|---|---|---|---|---|---|---|---|---|
| 83A10 | 9 | 11 | 15 | 16 | 17 | 18 | 19 | 20 |
| Mab21 | 10 | 12 | 21 | 22 | 17 | 23 | 24 | 20 |
| Mab22 | 10 | 13 | 21 | 22 | 17 | 25 | 26 | 20 |
| Mab42 | 10 | 14 | 21 | 22 | 17 | 27 | 28 | 20 |
| Mab27 | 38 | 12 | 29 | 30 | 17 | 31 | 32 | 33 |
| Mab33 | 39 | 12 | 34 | 35 | 17 | 31 | 32 | 33 |
| Mab39 | 40 | 12 | 36 | 37 | 17 | 31 | 32 | 33 |

TABLE 2A

Additional constructs

| | SEQ ID NO: | | | |
|---|---|---|---|---|
| Fragment/Construct | 83A10 | Mab21 | Mab22 | Mab42 |
| BCMA CH1 | 41 | 41 | 41 | 41 |
| BCMA CL | 42 | 42 | 42 | 42 |
| CD3 CH1 | 43 | 43 | 43 | 43 |
| CD3 CL | 44 | 44 | 44 | 44 |

TABLE 2B

Additional constructs

| | SEQ ID NO: | | | |
|---|---|---|---|---|
| Construct | 83A10 | Mab21 | Mab22 | Mab42 |
| BCMA VH_CH1cv × CD3 VL_CH1 Fc knob LALA PG (knob HC) | 45 | 49 | 52 | 55 |
| BCMAcv HC hole LALA PG (hole HC) | 46 | 50 | 53 | 56 |

TABLE 2B-continued

Additional constructs

| Construct | SEQ ID NO: | | | |
|---|---|---|---|---|
| | 83A10 | Mab21 | Mab22 | Mab42 |
| BCMAcv hum IgG1 LC (BCMA LC) | 47 | 51 | 54 | 57 |
| CD3 VH_CL (CD3 LC) | 48 | 48 | 48 | 48 |

To make the following (2+1) Fc-containing anti-BCMA/anti-CD3 TCBs, the respective constructs/sequence IDs as mentioned in the Table 2B above were used:
83A10-TCBcv: 45, 46, 47 (×2), 48 (FIG. 2A)
21-TCBcv: 48, 49, 50, 51 (×2) (FIG. 2A)
22-TCBcv: 48, 52, 53, 54 (×2) (FIG. 2A)
42-TCBcv: 48, 55, 56, 57 (×2) (FIG. 2A)

F. Methods of Treatment and Prevention and Compounds for Use in Such Methods Compounds 1, 2 and 3 and their enantiomers, mixtures of enantiomers, tautomers, isotopologs, or pharmaceutically acceptable salts as provided herein, in combination with the bispecific antibody specifically binding to human B cell maturation antigen (BCMA) and to human CD3ε (CD3) provided herein, can be used in all methods of treatment as provided herein.

In one embodiment, provided herein is a method of treating multiple myeloma, which comprises administering to a patient Compound 1, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, provided herein is a compound for use in a method of treating multiple myeloma, wherein the compound is Compound 1, or an enantiomer, mixture of enantiomers, tautomer, isotopolog, or pharmaceutically acceptable salt thereof, wherein the method comprises administering to a patient Compound 1, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, provided herein is a method of treating multiple myeloma, which comprises administering to a patient Compound 2, or a tautomer, isotopolog, or pharmaceutically acceptable salt thereof, and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, provided herein is a compound for use in a method of treating multiple myeloma, wherein the compound is Compound 2, or tautomer, isotopolog, or pharmaceutically acceptable salt thereof, wherein the method comprises administering to a patient Compound 2, or a tautomer, isotopolog, or pharmaceutically acceptable salt thereof, and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, provided herein is a method of treating multiple myeloma, which comprises administering to a patient Compound 3, or a tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
i) CDR1L region of SEQ ID NO:23 and CDR2L region of SEQ ID NO:24,
ii) CDR1L region of SEQ ID NO:25 and CDR2L region of SEQ ID NO:26, or
iii) CDR1L region of SEQ ID NO:27 and CDR2L region of SEQ ID NO:28.

In one embodiment, provided herein is a compound for use in a method of treating multiple myeloma, wherein the compound is Compound 3, or tautomer, isotopolog, or pharmaceutically acceptable salt thereof, wherein the method comprises administering to a patient Compound 3, or a tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
i) CDR1L region of SEQ ID NO:23 and CDR2L region of SEQ ID NO:24,
ii) CDR1L region of SEQ ID NO:25 and CDR2L region of SEQ ID NO:26, or
iii) CDR1L region of SEQ ID NO:27 and CDR2L region of SEQ ID NO:28.

In one embodiment, provided herein is a method of preventing multiple myeloma, which comprises administering to a patient a compound provided herein, e.g., Compound 1, Compound 2 or Compound 3, or an enantiomer, mixture of enantiomers, tautomer, isotopolog, or pharmaceutically acceptable salt thereof and a bispecific antibody comprises a first binding part specifically binding to human B cell maturation antigen (BCMA) and a second binding part specifically binding to human CD3ε (CD3) provided herein, optionally wherein the bispecific antibody is characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
i) CDR1L region of SEQ ID NO:23 and CDR2L region of SEQ ID NO:24,
ii) CDR1L region of SEQ ID NO:25 and CDR2L region of SEQ ID NO:26, or
iii) CDR1L region of SEQ ID NO:27 and CDR2L region of SEQ ID NO:28.

In one embodiment, provided herein is a compound for use in a method of preventing multiple myeloma, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the method comprises administering to a patient a compound provided herein, e.g., Compound 1, Compound 2 or Compound 3, or an enantiomer, mixture of enantiomers, tautomer, isotopolog, or pharmaceutically acceptable salt thereof and a bispecific antibody comprises a first binding part specifically binding to human B cell maturation antigen (BCMA) and a second binding part specifically binding to human CD3ε (CD3) provided herein, optionally wherein the bispecific antibody is characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
i) CDR1L region of SEQ ID NO:23 and CDR2L region of SEQ ID NO:24,
ii) CDR1L region of SEQ ID NO:25 and CDR2L region of SEQ ID NO:26, or
iii) CDR1L region of SEQ ID NO:27 and CDR2L region of SEQ ID NO:28.

In another embodiment, provided herein is method of managing multiple myeloma, which comprises administering to a patient a compound provided herein, e.g., Compound 1, Compound 2 or Compound 3, or an enantiomer, mixture of enantiomers, tautomer, isotopolog, or pharmaceutically acceptable salt thereof and a bispecific antibody comprises a first binding part specifically binding to human B cell maturation antigen (BCMA) and a second binding part specifically binding to human CD3ε (CD3) provided herein, optionally wherein the bispecific antibody is characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
i) CDR1L region of SEQ ID NO:23 and CDR2L region of SEQ ID NO:24,
ii) CDR1L region of SEQ ID NO:25 and CDR2L region of SEQ ID NO:26, or
iii) CDR1L region of SEQ ID NO:27 and CDR2L region of SEQ ID NO:28.

In another embodiment, provided herein is a compound for use in a method of managing multiple myeloma, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the method comprises administering to a patient a compound provided herein, e.g., Compound 1, Compound 2 or Compound 3, or an enantiomer, mixture of enantiomers, tautomer, isotopolog, or pharmaceutically acceptable salt thereof and a bispecific antibody comprises a first binding part specifically binding to human B cell maturation antigen (BCMA) and a second binding part specifically binding to human CD3ε (CD3) provided herein, optionally wherein the bispecific antibody is characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
i) CDR1L region of SEQ ID NO:23 and CDR2L region of SEQ ID NO:24,
ii) CDR1L region of SEQ ID NO:25 and CDR2L region of SEQ ID NO:26, or
iii) CDR1L region of SEQ ID NO:27 and CDR2L region of SEQ ID NO:28.

In one embodiment, also provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. *Leukemia,* 2006; (10) 10: 1-7) of a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
 i) CDR1L region of SEQ ID NO:23 and CDR2L region of SEQ ID NO:24,
 ii) CDR1L region of SEQ ID NO:25 and CDR2L region of SEQ ID NO:26, or
 iii) CDR1L region of SEQ ID NO:27 and CDR2L region of SEQ ID NO:28.

In one embodiment, also provided herein are methods for inducing a therapeutic response assessed with the International Myeloma Working Group (IMWG) consensus criteria for response and minimal residual disease assessment (Rajkumar et al., *Blood,* 2011, 117(18):4691-5; Kumar et al., *Lancet Oncol.,* 2016,17(8):e328-e346) of a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
 i) CDR1L region of SEQ ID NO:23 and CDR2L region of SEQ ID NO:24,
 ii) CDR1L region of SEQ ID NO:25 and CDR2L region of SEQ ID NO:26, or
 iii) CDR1L region of SEQ ID NO:27 and CDR2L region of SEQ ID NO:28.

In one embodiment, provided herein is a compound for use in methods for inducing a therapeutic response assessed with the International Uniform Response Criteria for Multiple Myeloma (IURC) (see Durie B G M, Harousseau J-L, Miguel J S, et al. International uniform response criteria for multiple myeloma. *Leukemia,* 2006; (10) 10: 1-7) of a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
 i) CDR1L region of SEQ ID NO:23 and CDR2L region of SEQ ID NO:24,
 ii) CDR1L region of SEQ ID NO:25 and CDR2L region of SEQ ID NO:26, or
 iii) CDR1L region of SEQ ID NO:27 and CDR2L region of SEQ ID NO:28.

In one embodiment, provided herein is a compound for use in methods for inducing a therapeutic response assessed with the International Myeloma Working Group (IMWG) consensus criteria for response and minimal residual disease assessment (Rajkumar et al., *Blood,* 2011, 117(18):4691-5; Kumar et al., *Lancet Oncol.,* 2016,17(8):e328-e346) of a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
 i) CDR1L region of SEQ ID NO:23 and CDR2L region of SEQ ID NO:24,
 ii) CDR1L region of SEQ ID NO:25 and CDR2L region of SEQ ID NO:26, or
 iii) CDR1L region of SEQ ID NO:27 and CDR2L region of SEQ ID NO:28.

In another embodiment, provided herein are methods for achieving a stringent complete response, complete response, or very good partial response, as determined by the International Uniform Response Criteria for Multiple Myeloma (IURC) in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein are methods for achieving a sustained MRD-negativity, flow MRD-negativity, sequencing MRD-negativity, imaging plus MRD-negativity, stringent complete response, complete response, or very good partial response, as determined by the International Myeloma Working Group (IMWG) consensus criteria for response and minimal residual disease assessment in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein is a compound for use in methods for achieving a stringent complete response, complete response, or very good partial response, as determined by the International Uniform Response Criteria for Multiple Myeloma (IURC) in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein is a compound for use in methods for achieving a sustained MRD-negativity, flow MRD-negativity, sequencing MRD-negativity, imaging plus MRD-negativity, stringent complete response, complete response, or very good partial response, as determined by the International Myeloma Working Group (IMWG) consensus criteria for response and minimal residual disease assessment in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein are methods for achieving an increase in overall survival, progression-free survival, event-free survival, time to progression, or disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
- i) CDR1L region of SEQ ID NO:23 and CDR2L region of SEQ ID NO:24,
- ii) CDR1L region of SEQ ID NO:25 and CDR2L region of SEQ ID NO:26, or
- iii) CDR1L region of SEQ ID NO:27 and CDR2L region of SEQ ID NO:28.

In another embodiment, provided herein is a compound for use in methods for achieving an increase in overall survival, progression-free survival, event-free survival, time to progression, or disease-free survival in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
- i) CDR1L region of SEQ ID NO:23 and CDR2L region of SEQ ID NO:24,
- ii) CDR1L region of SEQ ID NO:25 and CDR2L region of SEQ ID NO:26, or
- iii) CDR1L region of SEQ ID NO:27 and CDR2L region of SEQ ID NO:28.

In another embodiment, provided herein are methods for achieving an increase in overall survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
- i) CDR1L region of SEQ ID NO:23 and CDR2L region of SEQ ID NO:24,
- ii) CDR1L region of SEQ ID NO:25 and CDR2L region of SEQ ID NO:26, or
- iii) CDR1L region of SEQ ID NO:27 and CDR2L region of SEQ ID NO:28.

In another embodiment, provided herein is a compound for use in methods for achieving an increase in overall survival in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
- i) CDR1L region of SEQ ID NO:23 and CDR2L region of SEQ ID NO:24,
- ii) CDR1L region of SEQ ID NO:25 and CDR2L region of SEQ ID NO:26, or
- iii) CDR1L region of SEQ ID NO:27 and CDR2L region of SEQ ID NO:28.

In another embodiment, provided herein are methods for achieving an increase in progression-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
- i) CDR1L region of SEQ ID NO:23 and CDR2L region of SEQ ID NO:24,
- ii) CDR1L region of SEQ ID NO:25 and CDR2L region of SEQ ID NO:26, or
- iii) CDR1L region of SEQ ID NO:27 and CDR2L region of SEQ ID NO:28.

In another embodiment, provided herein is a compound for use in methods for achieving an increase in progression-free survival in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein are methods for achieving an increase in event-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein is a compound for use in methods for achieving an increase in event-free survival in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein are methods for achieving an increase in time to progression in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein is a compound for use in methods for achieving an increase in time to progression in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, provided herein are methods for achieving an increase in disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
    i) CDR1L region of SEQ ID NO:23 and CDR2L region of SEQ ID NO:24,
    ii) CDR1L region of SEQ ID NO:25 and CDR2L region of SEQ ID NO:26, or
    iii) CDR1L region of SEQ ID NO:27 and CDR2L region of SEQ ID NO:28.

In another embodiment, provided herein is a compound for use in methods for achieving an increase in disease-free survival in a patient, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering an effective amount of a compound described herein, e.g., Compound 1, Compound 2 or Compound 3, or an enantiomer, mixture of enantiomers, tautomer, isotopolog, or pharmaceutically acceptable salt thereof, and a bispecific antibody specifically binding to human B cell maturation antigen (BCMA) and to human CD3ε (CD3) provided herein to a patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
    i) CDR1L region of SEQ ID NO:23 and CDR2L region of SEQ ID NO:24,
    ii) CDR1L region of SEQ ID NO:25 and CDR2L region of SEQ ID NO:26, or
    iii) CDR1L region of SEQ ID NO:27 and CDR2L region of SEQ ID NO:28.

Also provided herein are methods of treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not. Also provided herein is a compound for use in methods of treating patients who have been previously treated for multiple myeloma but are non-responsive to standard therapies, as well as those who have not previously been treated. Further encompassed is a compound for use in methods of treating patients who have undergone surgery in an attempt to treat multiple myeloma, as well as those who have not. Also provided herein is a compound for us in methods of treating patients who have been previously undergone transplant therapy, as well as those who have not.

The methods provided herein include treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma. The methods provided herein include treatment of multiple myeloma that is newly diagnosed multiple myeloma (including low risk, intermediate risk, and high risk newly diagnosed multiple myeloma). The methods provided herein include prevention of multiple myeloma that is newly diagnosed multiple myeloma (including low risk, intermediate risk, and high risk newly diagnosed multiple myeloma). The methods provided herein include management of multiple myeloma that is newly diagnosed (including low risk, intermediate risk, and high risk newly diagnosed multiple myeloma) multiple myeloma. In one embodiment, the methods provided herein reduce, maintain or eliminate minimal residual disease (MRD). In one embodiment, methods provided herein encompass treating, preventing or managing various types of multiple myeloma, such as monoclonal gammopathy of undetermined significance (MGUS), low risk, intermediate risk, and high risk multiple myeloma, transplant eligible and transplant ineligible multiple myeloma, smoldering (indolent) multiple myeloma (including low risk, intermediate risk, and high risk smouldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a compound described herein. In one embodiment, the multiple myeloma is plasma cell leukemia. In another embodiment, methods provided herein encompass treating, preventing or managing multiple myeloma characterized by genetic abnormalities, such as Cyclin D translocations (for example, t(11;14)(q13;q32); t(6;14)(p21;32); t(12; 14)(p13;q32); or t(6;20); MMSET translocations (for example, t(4;14)(p16;q32)); MAF translocations (for example, t(14;16)(q32;q32); t(20; 22); t(16; 22)(q11;q13); or t(14;20)(q32;q11)); or other chromosome factors (for example, deletion of 17p13, or chromosome 13; del(17/17p), nonhyperdiploidy, and gain (lq)), by administering a therapeutically effective amount of a compound described herein. In one embodiment, the methods comprise administering a therapeutically effective amount of Compound 1, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
    i) CDR1L region of SEQ ID NO:23 and CDR2L region of SEQ ID NO:24,
    ii) CDR1L region of SEQ ID NO:25 and CDR2L region of SEQ ID NO:26, or iii) CDR1L region of SEQ ID NO:27 and CDR2L region of SEQ ID NO:28.

In another embodiment, the methods comprise administering a therapeutically effective amount of Compound 2, or a tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In another embodiment, the methods comprise administering a therapeutically effective amount of Compound 3, or a tautomer, isotopolog, or pharmaceutically acceptable salt thereof and a bispecific antibody specifically binding to human B cell maturation antigen (BCMA) and to human CD3ε (CD3) provided herein, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p and t(14;16)(q32;q32).

In some such embodiments, the multiple myeloma is transplant eligible newly diagnosed multiple myeloma. In another embodiment, the multiple myeloma is transplant ineligible newly diagnosed multiple myeloma. In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory or resistant to lenalidomide. In another embodiment, the multiple myeloma is refractory to lenalidomide. In another embodiment, the multiple myeloma is resistant to lenalidomide. In another embodiment, the multiple myeloma is refractory or resistant to pomalidomide. In another embodiment, the multiple myeloma is refractory to pomalidomide. In another embodiment, the multiple myeloma is resistant to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, CC 122 or CC220), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, CC 122 or CC220) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, CC 122 or CC220), and one other active agent, as described herein.

In certain embodiments, provided herein are methods of treating, preventing, and/or managing multiple myeloma, including relapsed/refractory multiple myeloma in patients with impaired renal function or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, to a patient having relapsed/refractory multiple myeloma with impaired renal function, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In certain embodiments, provided herein is a compound for use in methods of treating, preventing, and/or managing multiple myeloma, including relapsed/refractory multiple myeloma in patients with impaired renal function or a symptom thereof, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering a therapeutically effective amount of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, to a patient having relapsed/refractory multiple myeloma with impaired renal function, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In certain embodiments, provided herein are methods of treating, preventing, and/or managing multiple myeloma, including relapsed or refractory multiple myeloma in frail patients or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein to a frail patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In certain embodiments, provided herein is a compound for use in methods of treating, preventing, and/or managing multiple myeloma, including relapsed or refractory multiple myeloma in frail patients or a symptom thereof, wherein the compound is a compound provided herein, e.g., Compound 1, Compound 2 or Compound 3, or an enantiomer, mixture of enantiomers, tautomer, isotopolog, or pharmaceutically acceptable salt thereof, wherein the methods comprise administering a therapeutically effective amount of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein to a frail patient having multiple myeloma, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28.

In some such embodiments, the frail patient is characterized by ineligibility for induction therapy, or intolerance to dexamethasone treatment. In some such embodiment the frail patient is elderly, for example, older than 65 years old.

In certain embodiments, the patient to be treated with one of the methods provided herein has not been treated with multiple myeloma therapy prior to the administration of Compound 1, Compound 2 or Compound 3 provided herein, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein. In certain embodiments, the patient to be treated with one of the methods provided herein has been treated with multiple myeloma therapy prior to the administration of Compound 1, Compound 2 or Compound 3 provided herein or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein.

In certain embodiments, the patient to be treated with one of the methods provided herein has developed drug resistance to the anti-multiple myeloma therapy. In some such embodiments, the patient has developed resistance to one, two, three, four, five, or more anti-multiple myeloma therapies. In one embodiment, the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, CC122 or CC220). In one embodiment, the therapies comprise one or more of a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, CC122 or CC220). In one embodiment, the therapies comprise one or more of alkylating agents (e.g., melphalan, cyclophosphamide, bendamustine), histone deacetylase inhibitors (e.g., panobinostat), other monoclonal antibodies (e.g., anti-SLAMF7 antibody, for example, elotuzumab), glucocorticoids (e.g., dexamethasone, prednisone), other anti-multiple myeloma therapies (e.g., cisplatin, eotoposide, doxorubicin), and cellular therapies (e.g., CAR-T).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

G. Dosing of Compound 1, Compound 2 or Compound 3

In certain embodiments, a therapeutically or prophylactically effective amount of the compound is from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of the compound is from about 0.01 to about 25 mg per day. In one embodiment, a therapeutically or prophylactically effective amount of the compound is from about 0.01 to about 10 mg per day. In one embodiment, a therapeutically or prophylactically effective amount of the compound is from about 0.01 to about 5 mg per day. In one embodiment, a therapeutically or prophylactically effective amount of the compound is from about 0.01 to about 2 mg per day. In one embodiment, a therapeutically or prophylactically effective amount of the compound is from about 0.01 to about 1 mg per day. In one embodiment, a therapeutically or prophylactically effective amount of the compound is from about 0.01 to about 0.5 mg per day. In one embodiment, a therapeutically or prophylactically effective amount of the compound is from about 0.01 to about 0.25 mg per day. In one embodiment, a therapeutically or prophylactically effective amount of the compound is from about 0.1 to about 25 mg per day. In one embodiment, a therapeutically or prophylactically effective amount of the compound is from about 0.1 to about 10 mg per day. In one embodiment, a therapeutically or prophylactically effective amount of the compound is from about 0.1 to about 5 mg per day. In one embodiment, a therapeutically or prophylactically effective amount of the compound is from about 0.1 to about 2 mg per day. In one embodiment, a therapeutically or prophylactically effective amount of the compound is from about 0.1 to about 1 mg per day. In one embodiment, a therapeutically or prophylactically effective amount of the compound is from about 0.1 to about 0.5 mg per day. In one embodiment, a therapeutically or prophylactically effective amount of the compound is from about 0.1 to about 0.25 mg per day. In one embodiment, a therapeutically or prophylactically effective amount of the compound is from about 0.5 to about 25 mg per day. In one embodiment, a therapeutically or prophylactically effective amount of the compound is from about 0.5 to about 10 mg per day. In one embodiment, a therapeutically or prophylactically effective amount of the compound is from about 0.5 to about 5 mg per day. In one embodiment, a therapeutically or prophylactically effective amount of the compound is from about 0.5 to about 2 mg per day. In one embodiment, a therapeutically or prophylactically effective amount of the compound is from about 0.5 to about 1 mg per day. In one embodiment, a therapeutically or prophylactically effective amount of the compound is from about 1 to about 25 mg per day. In one embodiment, a therapeutically or prophylactically effective amount of the compound is from about 1 to about 10 mg per day. In one embodiment, a therapeutically or prophylactically effective amount of the compound is from about 1 to about 5 mg per day. In one embodiment, a therapeutically or prophylactically effective amount of the compound is from about 1 to about 2.5 mg per day. In one embodiment, a therapeutically or prophylactically effective amount of the compound is from about 1 to about 2 mg per day. In one embodiment, a therapeutically or prophylactically effective amount of Compound 1, Compound 2 or Compound 3 is from about 0.1 mg per day to about 0.4 mg per day.

In certain embodiments, the therapeutically or prophylactically effective amount is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day. In certain embodiments, the therapeutically or prophylactically effective amount is about 0.1 mg per day. In certain embodiments, the therapeutically or prophylactically effective amount is about 0.2 mg per day. In certain embodiments, the therapeutically or prophylactically effective amount is about 0.3 mg per day. In certain embodiments, the therapeutically or prophylactically effective amount is about 0.4 mg per day. In certain embodiments, the therapeutically or prophylactically effective amount is about 0.5 mg per day. In certain embodiments, the therapeutically or prophylactically effective amount is about 0.6 mg per day. In certain embodiments, the therapeutically or prophylactically effective amount is about 0.7 mg per day. In certain embodiments, the therapeutically or prophylactically effective amount is about 0.8 mg per day. In certain embodiments, the therapeutically or prophylactically effective amount is about 0.9 mg per day. In certain embodiments, the therapeutically or prophylactically effective amount is about 1 mg per day. In certain embodiments, the therapeutically or prophylactically effective amount is about 2 mg per day. In certain embodiments, the therapeutically or prophylactically effective amount is about 3 mg per day. In certain embodiments, the therapeutically or prophylactically effective amount is about 4 mg per day. In certain embodiments, the therapeutically or prophylactically effective amount is about 5 mg per day. In certain embodiments, the therapeutically or prophylactically effective amount is about 6 mg per day. In certain embodiments, the therapeutically or prophylactically effective amount is about 7 mg per day. In certain embodiments, the therapeutically or prophylactically effective amount is about 8 mg per day. In certain embodiments, the therapeutically or prophylactically effective amount is about 9 mg per day. In certain embodiments, the therapeutically or prophylactically effective amount is about 10 mg per day. In certain embodiments, the therapeutically or prophylactically effective amount is about 15 mg per day. In certain embodiments, the therapeutically or prophylactically effective amount is about 20 mg per day. In certain embodiments, the therapeutically or prophylactically effective amount is about 25 mg per day.

In one embodiment, the recommended daily dose range of Compound 1, Compound 2 or Compound 3, or an enantiomer, mixture of enantiomers, tautomer, isotopolog, or pharmaceutically acceptable salt thereof, for the conditions described herein lie within the range of from about 0.1 mg to about 25 mg per day, in one embodiment given as a single once-a-day dose, or in divided doses throughout a day. In other embodiments, the dosage ranges from about 0.1 to about 10 mg per day. Specific doses per day include to 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day. In one embodiment, the specific dose per day is 0.1 mg per day. In one embodiment, the specific dose per day is 0.2 mg per day. In one embodiment, the specific dose per day is 0.3 mg per day. In one embodiment, the specific dose per day is 0.4 mg per day. In one embodiment, the specific dose per day is 0.5 mg per day. In one embodiment, the specific dose per day is 1 mg per day. In one embodiment, the specific dose per day is 2 mg per day. In one embodiment, the specific dose per day is 3 mg per day. In one embodiment, the specific dose per day is 4 mg per day. In one embodiment, the specific dose per day is 5 mg per day. In one embodiment, the specific dose per day is 6 mg per day. In one embodiment, the specific dose per day is 7 mg per day. In one embodiment, the specific dose per day is 8 mg per day. In one embodiment, the specific dose per day is 9 mg per day. In one embodiment, the specific dose per day is 10 mg per day. In one embodiment, the specific dose per day is 11 mg per day. In one embodiment, the specific dose per day is 12 mg per day. In one embodiment, the specific dose per day is 13 mg per day. In one embodiment, the specific dose per day is 14 mg per day. In one embodiment, the specific dose per day is 15 mg per day. In one embodiment, the specific dose per day is 16 mg per day. In one embodiment, the specific dose per day is 17 mg per day. In one embodiment, the specific dose per day is 18 mg per day. In one embodiment, the specific dose per day is 19 mg per day. In one embodiment, the specific dose per day is 20 mg per day. In one embodiment, the specific dose per day is 21 mg per day. In one embodiment, the specific dose per day is 22 mg per day. In one embodiment, the specific dose per day is 23 mg per day. In one embodiment, the specific dose per day is 24 mg per day. In one embodiment, the specific dose per day is 25 mg per day.

In a specific embodiment, the recommended starting dosage may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day given either the height or weight of a subject or both (see, www.fda.gov/cder/cancer/animalframe.htm). For example, a dose of 1 mg/kg/day for a 65 kg human is approximately equal to 38 mg/m$^2$/day.

Depending on the state of the disease to be treated and the subject's condition, Compound 1, Compound 2 or Compound 3 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, laboratory evaluations, visualization of the tumor that has been imaged using X-ray, CAT, PET, or MRI scan and other commonly accepted evaluation modalities.

In one embodiment of the methods provided herein, a compound provided herein, e.g., Compound 1, Compound 2 or Compound 3, or an enantiomer, mixture of enantiomers, tautomer, isotopolog, or pharmaceutically acceptable salt thereof, is administered prior to a bispecific antibody specifically binding to human B cell maturation antigen (BCMA) and to human CD3ε (CD3) provided herein. In one embodiment of the methods provided herein, a compound provided herein, e.g., Compound 1, Compound 2 or Compound 3, or an enantiomer, mixture of enantiomers, tautomer, isotopolog, or pharmaceutically acceptable salt thereof, is administered concurrently with a bispecific antibody specifically binding to human B cell maturation antigen (BCMA) and to human CD3ε (CD3) provided herein. In one embodiment of the methods provided herein, a compound provided herein, e.g., Compound 1, Compound 2 or Compound 3, or an enantiomer, mixture of enantiomers, tautomer, isotopolog, or pharmaceutically acceptable salt thereof, is administered subsequent to a bispecific antibody specifically binding to human B cell maturation antigen (BCMA) and to human CD3ε (CD3) provided herein.

Compound 1, Compound 2 or Compound 3 provided herein, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In one embodiment, a therapeutically effective amount of Compound 1, Compound 2 or Compound 3 is administered in a treatment cycle which includes an administration period of up to 20 days followed by a rest period. In one embodiment, a therapeutically effective amount of Compound 1, Compound 2 or Compound 3 is administered in a treatment cycle which includes an administration period of up to 15 days followed by a rest period. In one embodiment, a therapeutically effective amount of Compound 1, Compound 2 or Compound 3 is administered in a treatment cycle which includes an administration period of up to 10 days followed by a rest period. In one embodiment, a therapeutically effective amount of Compound 1, Compound 2 or Compound 3 is administered in a treatment cycle which includes an administration period of up to 7 days followed by a rest period. In one embodiment, a therapeutically effective amount of Compound 1, Compound 2 or Compound 3 is administered in a treatment cycle which includes an administration period of up to 5 days followed by a rest period. In one embodiment, a therapeutically effective amount of Compound 1, Compound 2 or Compound 3 is administered in a treatment cycle which includes an administration period of up to 4 days followed by a rest period. In one embodiment, a therapeutically effective amount of Compound 1, Compound 2 or Compound 3 is administered in a treatment cycle which includes an administration period of up to 3 days followed by a rest period.

In one embodiment, the treatment cycle includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days. In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle includes an administration of a therapeutically effective amount of Compound 1, Compound 2 or Compound 3 on days 1 to 5 of a 28 day cycle. In another embodiment, the treatment cycle includes an administration of Compound 1, Compound 2 or Compound 3 on days 1 to 10 of a 28 day cycle. In one embodiment, the treatment cycle includes an administration of a therapeutically effective amount of Compound 1, Compound 2 or Compound 3 on days 1 to 21 of a 28 day cycle. In another embodiment, the treatment cycle includes an administration of a therapeutically effective amount of Compound 1, Compound 2 or Compound 3 on days 1 to 5 of a 7 day cycle. In another embodiment, the treatment cycle includes an administration of a therapeutically effective amount of Compound 1, Compound 2 or Compound 3 on days 1 to 7 of a 7 day cycle. In one embodiment, the treatment cycle includes an administration of a therapeutically effective amount of Compound 1, Compound 2 or Compound 3 on days 1 to 10 and days 15 to 24 of a 28 day cycle. In one embodiment, the treatment cycle includes an administration of a therapeutically effective amount of Compound 1, Compound 2 or Compound 3 on days 1 to 3 and days 15 to 18 of a 28 day cycle. In one embodiment, the treatment cycle includes an administration of a therapeutically effective amount of Compound 1, Compound 2 or Compound 3 on days 1 to 7 and days 15 to 21 of a 28 day cycle. In one embodiment, the treatment cycle includes an administration of a therapeutically effective amount of Compound 1, Compound 2 or Compound 3 on days 1 to 5 and days 15 to 19 of a 28 day cycle. In one embodiment, the treatment cycle includes an administration of a therapeutically effective amount of Compound 1, Compound 2 or Compound 3 on days 1 to 3 and days 15 to 17 of a 28 day cycle.

In one embodiment, the treatment cycle includes an administration of a therapeutically effective amount of Compound 1, Compound 2 or Compound 3 on days 1 to 14 of a 21 day cycle. In another embodiment, the treatment cycle includes an administration of Compound 1, Compound 2 or Compound 3 on days 1 to 4 and 8 to 11 of a 21 day cycle. In one embodiment, the treatment cycle includes an administration of a therapeutically effective amount of Compound 1, Compound 2 or Compound 3 on days 1 to 5 and 8 to 12 of a 21 day cycle. In another embodiment, the treatment cycle includes an administration of a therapeutically effective amount of Compound 1, Compound 2 or Compound 3 on days 1 to 5 and 11 to 15 of a 21 day cycle. In another embodiment, the treatment cycle includes an administration of a therapeutically effective amount of Compound 1, Compound 2 or Compound 3 on days 1 to 5, 8 to 12 and 15 to 19 of a 21 day cycle. In another embodiment, the treatment cycle includes an administration of a therapeutically effective amount of Compound 1, Compound 2 or Compound 3 on days 1 to 4, 8 to 11 and 15 to 18 of a 21 day cycle. In another embodiment, the treatment cycle includes an administration of a therapeutically effective amount of Compound 1, Compound 2 or Compound 3 on days 1 to 4, 8 to 10 and 15 to 17 of a 21 day cycle. In another embodiment, the treatment cycle includes an administration of a therapeutically effective amount of Compound 1, Compound 2 or Compound 3 on days 1 to 3, and 8 to 11 of a 21 day cycle. In another embodiment, the treatment cycle includes an administration of a therapeutically effective amount of Compound 1, Compound 2 or Compound 3 on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of Compound 1, Compound 2 or Compound 3 is administered for 1 to 13 cycles of 28 days (e.g. about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day, administered once per day. In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering Compound 1, Compound 2 or Compound 3 once a day at a dosage amount of about 0.1 mg on days 1 to 10 and 15 to 24 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering Compound 1, Compound 2 or Compound 3 twice a day at a dosage amount of about 0.2 mg on days 1 to 3 and 15 to 17 of a 28 day cycle. In one such embodiment, the compound is administered on days 1 to 3 (morning and evening), day 14 (evening only), days 15 and 16 (morning and evening), and day 17 (morning only) in Cycle 1.

H. Dosing of Bispecific Antibody Specifically Binding to BCMA and to CD3

In one embodiment the bispecific antibody is administered once or twice a week in one embodiment via subcutaneous administration (e.g. in one embodiment in the dose range of 0.1 to 2.5, in one embodiment to 25 mg/m$^2$/week, in one embodiment to 250 mg/m$^2$/week). Due to superior cytotoxicity activities of the bispecific antibody they can be administered at least at the same magnitude of clinical dose range (or even lower) as compared to conventional monospecific antibodies or conventional bispecific antibodies that are not T cell bispecifics (i.e. do not bind to CD3 on one arm). It is envisaged that for a bispecific antibody subcutaneous administration is preferred in the clinical settings (e.g. in the dose range of 0.1-250 mg/m$^2$/week). In addition, in patients with high levels of serum APRIL and BAFF (e.g. multiple myeloma patients) it may not be required to increase the dose for the bispecific antibody as it may not be affected by ligand competition. In contrast, the doses for other ligand-blocking/competing anti-BCMA antibodies may need to be increased in those patients. Another advantage of the bispecific antibody is an elimination half-life of about 4 to 12 days which allows at least once or twice/week administration.

In one embodiment the bispecific antibody is an antibody with properties allowing for once/twice a week treatment by intravenous route but in one embodiment via subcutaneous administration (e.g. a dosage in the range of 200-2000 mg/m$^2$/week for 4 weeks). It is envisaged that for the bispecific antibody subcutaneous administration is possible and preferred in the clinical settings (e.g. in the dose range of 200-2000 mg/m$^2$/week, depending on the disease indications). In addition, in patients with high levels of serum APRIL and BAFF (e.g. multiple myeloma patients) it may not be required to increase the dose for the bispecific antibody (e.g. non-ligand blocking/competing antibody) as it may not be affected by ligand competition. In contrast, the doses for other ligand-blocking/competing anti-BCMA antibodies may need to be increased in those patients, making subcutaneous administration technically more challenging (e.g. pharmaceutical). Another advantage of the bispecific antibody is based on the inclusion of an Fc portion, which is associated with an elimination half-life of 4 to 12 days and allows at least once or twice/week administration.

I. Combination Therapy with Additional Active Agent

Treatment with Compound 1, Compound 2 or Compound 3 provided herein, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, can also be combined or used in conjunction with (e.g. before, during, or after) conventional therapy including, but not limited to, surgery, biological therapy (including immunotherapy, for example with checkpoint inhibitors), radiation therapy, chemotherapy, stem cell transplantation, cell therapy, or other non-drug based therapy presently used to treat, prevent or manage multiple myeloma. The combined use of the compound provided herein and conventional therapy may provide a unique treatment regimen that is unexpectedly effective in certain patients. Without being limited by theory, it is believed that treatment with Compound 1, Compound 2 or Compound 3 and a bispecific antibody specifically binding to human B cell maturation antigen (BCMA) and to human CD3ε (CD3) provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A compound provided herein, e.g., Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, and an additional active ingredient can be administered to a patient prior to, during, or after the occurrence of the adverse effect associated with conventional therapy.

Compound 1, Compound 2 or Compound 3 provided herein, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, can also be combined or used in combination with additional therapeutic agents useful in the treatment and/or prevention of multiple myeloma described herein.

In one embodiment, provided herein is a method of treating multiple myeloma, comprising administering to a patient Compound 1, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of preventing multiple myeloma, comprising administering to a patient Compound 1, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of managing multiple myeloma, comprising administering to a patient Compound 1, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of treating multiple myeloma, comprising administering to a patient Compound 2, or a tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of preventing multiple myeloma, comprising administering to a patient Compound 2, or a tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of managing multiple myeloma, comprising administering to a patient Compound 2, or a tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of treating multiple myeloma, comprising administering to a patient Compound 3, or a tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of preventing multiple myeloma, comprising administering to a patient Compound 3, or a tautomer, isotopolog, or pharmaceutically acceptable salt thereof and a bispecific antibody specifically binding to human B cell maturation antigen (BCMA) and to human CD3ε (CD3) provided herein, in combination with an additional active agent. In one embodiment, provided herein is a method of managing multiple myeloma, comprising administering to a patient Compound 3, or a tautomer, isotopolog, or pharmaceutically acceptable salt thereof and a bispecific antibody specifically binding to human B cell maturation antigen (BCMA) and to human CD3ε (CD3) provided herein, in combination with an additional active agent.

In one embodiment, provided herein is a method of treating, preventing, or managing multiple myeloma, comprising administering to a patient Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in combination with one or more additional active agents, and optionally in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, e.g., Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapy (e.g., a prophylactic or therapeutic agent) to the subject. Quadruple therapy is also contemplated herein, as is quintuple therapy. In one embodiment, the third therapy is dexamethasone.

Administration of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, and one or more additional active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, is independent of the route of administration of an additional therapy. In one embodiment, Compound 1, Compound 2 or Compound 3, or an enantiomer, mixture of enantiomers, tautomer, isotopolog, or pharmaceutically acceptable salt thereof, is administered orally and a bispecific antibody specifically binding to human B cell maturation antigen (BCMA) and to human CD3ε (CD3) provided herein is administered by intravenous route but in one embodiment via subcutaneous administration. In another embodiment, Compound 1, Compound 2 or Compound 3 is administered intravenously and a bispecific antibody specifically binding to human B cell maturation antigen (BCMA) and to human CD3ε (CD3) provided herein is administered by intravenous route but in one embodiment via subcutaneous administration. Thus, in accordance with these embodiments, Compound 1, Compound 2 or Compound 3, or an enantiomer, mixture of enantiomers, tautomer, isotopolog, or pharmaceutically acceptable salt thereof, is administered orally or intravenously, a bispecific antibody specifically binding to human B cell maturation antigen (BCMA) and to human CD3ε (CD3) provided herein is administered by intravenous route but in one embodiment via subcutaneous administration, and the additional therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1, Compound 2 or Compound 3, or an enantiomer, mixture of enantiomers, tautomer, isotopolog, or pharmaceutically acceptable salt thereof, and the additional therapy are administered by the same mode of administration, orally or by IV and a bispecific antibody specifically binding to human B cell maturation antigen (BCMA) and to human CD3ε (CD3) provided herein is administered by intravenous route but in one embodiment via subcutaneous administration. In another embodiment, Compound 1, Compound 2 or Compound 3, or an enantiomer, mixture of enantiomers, tautomer, isotopolog, or pharmaceutically acceptable salt thereof, is administered by one mode of administration, e.g., by IV, whereas the additional agent (an anti-multiple myeloma agent) is administered by another mode of administration, e.g., orally and a bispecific antibody specifically binding to human B cell maturation antigen (BCMA) and to human CD3ε (CD3) provided herein is administered by intravenous route but in one embodiment via subcutaneous administration.

In one embodiment, the additional active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the additional active agent will depend on the specific agent used, the type of multiple myeloma being treated or managed, the severity and stage of disease, and the amount of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, provided herein and any optional additional active agents concurrently administered to the patient.

One or more additional active ingredients or agents can be used together with Compound 1, Compound 2 or Compound 3 and a bispecific antibody specifically binding to human B cell maturation antigen (BCMA) and to human CD3ε (CD3) provided herein in the methods and compositions provided herein. Additional active agents can be large molecules (e.g., proteins), small molecules (e.g., synthetic inorganic, organometallic, or organic molecules), or cell therapies (e.g., CAR cells).

Examples of additional active agents that can be used in the methods and compositions described herein include one or more of melphalan, vincristine, cyclophosphamide, etoposide, doxorubicin, bendamustine, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, C90010, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, EP11313 and EP11336), a BCL2 inhibitor (for example, venetoclax or navitoclax), an MCL-1 inhibitor (for example, AZD5991, AMG176, MIK665, S64315, or S63845), a corticosteroid (for example, prednisone), dexamethasone; an antibody (for example, a CS1 antibody, such as elotuzumab; a CD38 antibody, such as daratumumab isatuximab; or a BCMA antibody or antibody-conjugate, such as GSK2857916 or BI 836909), a checkpoint inhibitor (as described herein), or CAR cells (as described herein).

In one embodiment, the additional active agent used together with Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1. In some other embodiments, the dexamethasone is administered at a 4 mg dose on days 1, 2, 4, 5, 8, 9, 11 and 12 of a 21 day cycle (in one embodiment, cycles 1 to 8). In some other embodiments, the dexamethasone is administered at a 4 mg dose on days 1, 2, 8 and 9 of a 21 day cycle (in one embodiment, cycles ≥9). In some other embodiments, the dexamethasone is administered at a 4 mg dose on days 1, 2, 8, 9, 15, 16, 22 and 23 of a 28 day cycle.

In some other embodiments, the dexamethasone is administered at a 8 mg dose on days 1 and 8 of a 21 day cycle. In some other embodiments, the dexamethasone is administered at a 8 mg dose on days 1, 4, 8 and 11 of a 21 day cycle. In some embodiments, the dexamethasone is administered at a 8 mg dose on days 1, 8, and 15 of a 28 day cycle. In some other embodiments, the dexamethasone is administered at a 8 mg dose on days 1, 4, 8, 11, 15 and 18 of a 28 day cycle. In some embodiments, the dexamethasone is administered at a 8 mg dose on days 1, 8, 15, and 22 of a 28 day cycle. In one such embodiment, the dexamethasone is administered at a 8 mg dose on days 1, 10, 15, and 22 of Cycle 1. In some embodiments, the dexamethasone is administered at a 8 mg dose on days 1, 3, 15, and 17 of a 28 day cycle. In one such embodiment, the dexamethasone is administered at a 8 mg dose on days 1, 3, 14, and 17 of Cycle 1. In some other embodiments, the dexamethasone is administered at a 8 mg dose on days 1, 2, 4, 5, 8, 9, 11 and 12 of a 21 day cycle (in one embodiment, cycles 1 to 8). In some other embodiments, the dexamethasone is administered at a 8 mg dose on days 1, 2, 8 and 9 of a 21 day cycle (in one embodiment, cycles ≥9). In some other embodiments, the dexamethasone is administered at a 8 mg dose on days 1, 2, 8, 9, 15, 16, 22 and 23 of a 28 day cycle.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15 and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1. In some other embodiments, the dexamethasone is administered at a 10 mg dose on days 1, 2, 4, 5, 8, 9, 11 and 12 of a 21 day cycle (in one embodiment, cycles 1 to 8). In some other embodiments, the dexamethasone is administered at a 10 mg dose on days 1, 2, 8 and 9 of a 21 day cycle (in one embodiment, cycles ≥9). In some other embodiments, the dexamethasone is administered at a 10 mg dose on days 1, 2, 8, 9, 15, 16, 22 and 23 of a 28 day cycle.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15 and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1. In some other embodiments, the dexamethasone is administered at a 20 mg dose on days 1, 2, 4, 5, 8, 9, 11 and 12 of a 21 day cycle (in one embodiment, cycles 1 to 8). In some other embodiments, the dexamethasone is administered at a 20 mg dose on days 1, 2, 8 and 9 of a 21 day cycle (in one embodiment, cycles ≥9). In some other embodiments, the dexamethasone is administered at a 20 mg dose on days 1, 2, 8, 9, 15, 16, 22 and 23 of a 28 day cycle.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1. In some other embodiments, the dexamethasone is administered at a 40 mg dose on days 1, 2, 4, 5, 8, 9, 11 and 12 of a 21 day cycle (in one embodiment, cycles 1 to 8). In some other embodiments, the dexamethasone is administered at a 40 mg dose on days 1, 2, 8 and 9 of a 21 day cycle (in one embodiment, cycles ≥9). In some other embodiments, the dexamethasone is administered at a 40 mg dose on days 1, 2, 8, 9, 15, 16, 22 and 23 of a 28 day cycle.

In another embodiment, the additional active agent used together with Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in the methods and compositions described herein is bortezomib. In yet another embodiment, the additional active agent used together with Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in the methods and compositions described herein is daratumumab. In some such embodiments, the methods additionally comprise administration of dexamethasone. In some embodiments, the methods comprise administration of Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, with a proteasome inhibitor as described herein, a CD38 antibody as described herein and a corticosteroid as described herein.

In certain embodiments, Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, is administered in combination with checkpoint inhibitors. In one embodiment, one checkpoint inhibitor is used in combination with Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in connection with the methods provided herein. In another embodiment, two checkpoint inhibitors are used in combination with Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in connection with the methods provided herein. In yet another embodiment, three or more checkpoint inhibitors are used in combination with Compound 1, Compound 2 or Compound 3, or an enantiomer, mixture of enantiomers, tautomer, isotopolog, or pharmaceutically acceptable salt thereof and a bispecific antibody specifically binding to human B cell maturation antigen (BCMA) and to human CD3ε (CD3) provided herein, in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MED14736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.,* 2012, 3834).

In one embodiment, the checkpoint inhibitors is a TIM3 (T-cell immunoglobulin domain and mucin domain 3) inhibitor (Fourcade et al., *J. Exp. Med.,* 2010, 207, 2175-86; Sakuishi et al., *J. Exp. Med.,* 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MED16469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, Compound 1, Compound 2 or Compound 3 and a bispecific antibody specifically binding to human B cell maturation antigen (BCMA) and to human CD3ε (CD3) provided herein can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-A11, hsp70-2, KIAA0205, Mart2, Mum-1, 2, and 3, neo-PAP, myosin class I, OS-9, pml-RARa fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68KP1, C0-029, FGF-5, G250, Ga733 (EpCAM), HTgp-175, M344, MA-50, MG7-Ag, MOV18, NB\70K, NY-C0-1, RCAS1, SDCCAGi6, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3t signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 1 05(11):4247-4254 (2005).

J. Pharmaceutical Compositions

The pharmaceutical compositions provided herein contain therapeutically effective amounts of one or more of compounds provided herein and optionally a pharmaceutically acceptable carrier, diluent or excipient.

In a further embodiment, provided herein is a pharmaceutical composition comprising a compound provided herein and a bispecific antibody specifically binding to human B cell maturation antigen (BCMA) and to human CD3ε (CD3) provided herein, and a pharmaceutically acceptable excipient, optionally wherein the bispecific antibody comprises a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28. In one embodiment, the composition is for combined use in treating multiple myeloma.

In a further embodiment, provided herein is a pharmaceutical composition comprising Compound 1, Compound 2 or Compound 3, or an enantiomer, mixture of enantiomers, tautomer, isotopolog, or pharmaceutically acceptable salt thereof) and a bispecific antibody comprising a first binding part specifically binding to human B cell maturation antigen (BCMA) and a second binding part specifically binding to human CD3ε (CD3) provided herein, optionally wherein the bispecific antibody is characterized in that said first binding part comprises a VH region comprising a CDR1H region of SEQ ID NO:21, a CDR2H region of SEQ ID NO:22 and a CDR3H region of SEQ ID NO: 17 and a VL region comprising a CDR3L region of SEQ ID NO:20 and a CDR1L and CDR2L region combination selected from the group of
  i) CDR1L region of SEQ ID NO:23 and CDR2L region of SEQ ID NO:24,
  ii) CDR1L region of SEQ ID NO:25 and CDR2L region of SEQ ID NO:26, or
  iii) CDR1L region of SEQ ID NO:27 and CDR2L region of SEQ ID NO:28, and a pharmaceutically acceptable excipient. In one embodiment, the composition is for combined use in treating multiple myeloma.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

K. Evaluation of the Activity and Properties of the Combination

Standard physiological, pharmacological and biochemical procedures are available for testing the compounds to identify those that possess the desired properties, including anti-multiple myeloma proliferative activity and adequate safety profile. Such assays include, for example, biochemical assays such as binding assays, radioactivity incorporation assays, as well as a variety of cell based assays.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

5. EXAMPLES

Certain embodiments of the invention are illustrated by the following non-limiting examples.

Abbreviations

AIBN: Azobisisobutyronitrile
Boc tert-Butyloxycarbonyl
Boc$_2$O di-tert-Butyl dicarbonate
tBuOK Potassium tert-butoxide
DIEA Diisopropylethylamine
DMF N,N'-Dimethylformamide EtOAc Ethyl acetate
MeOH Methanol
MM Multiple Myeloma
NB S: N-bromosuccinimide,
NMR Nuclear Magentic Resonance
i-PrOAc: Isopropyl acetate
TBSCl tert-Butyl dimethylsilylchloride
THF Tetrahydrofuran
TLC Thin layer chromatography
TMSCl Trimethylsilyl chloride Example 1: Synthesis of 4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1)

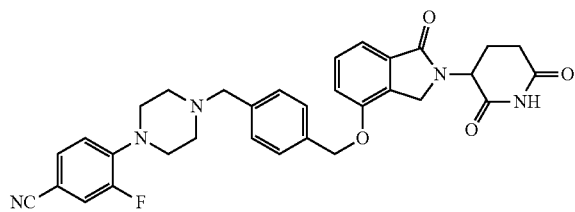 [SMILES: N#Cc1ccc(N2CCN(Cc3ccc(COc4cccc5c4CN(C4CCC(=O)NC4=O)C5=O)cc3)CC2)c(F)c1]

2-Amino-5-methoxy-5-oxopentanoic acid

To a suspension of 2-aminopentanedioic acid (250 g, 1.70 mol) in dry methanol (2.5 L) under nitrogen was added trimethylsilyl chloride (277 g, 2.55 mol) over 30 mins. The resulting clear solution was stirred at room temperature (20° C.) for 30 min. $^1$H NMR showed the starting material was consumed completely. The reaction mixture was used in the next step without further work-up. $^1$H NMR: 400 MHz CD$_3$OD δ: 4.17-4.15 (m, 1H), 3.71 (s, 3H), 2.70-2.60 (m, 2H), 2.33-2.25 (m, 2H).

2-((tert-Butoxycarbonyl)amino)-5-methoxy-5-oxopentanoic acid

To the above solution was added triethylamine (275 g, 2.72 mol) and di-tert-butyl dicarbonate (447.35 g, 2.05 mol). The reaction mixture was stirred at 25° C. for 2 h. The solution was concentrated to dryness, then water (2.5 L) was added to dissolve the residue. The resulting aqueous phase was washed with ethyl acetate (200 mL), then acidified to pH=3 by HCl (1 N) and extracted with ethyl acetate (1 L×3). The combined organic layers were washed with brine (800 mL), dried over sodium sulfate, filtered and concentrated to offer 2-(tert-butoxycarbonylamino)-5-methoxy-5-oxo-pentanoic acid (250 g 56% yield, two steps) as a white solid. $^1$H NMR: 400 MHz CD$_3$OD δ: 4.18-4.11 (m, 1H), 3.69 (s, 3H), 2.48-2.43 (m, 2H), 2.21-2.15 (m, 1H), 1.95-1.91 (m, 1H), 1.46 (s, 9H).

Methyl 5-amino-4-(tert-butoxycarbonyl amino)-5-oxo-pentanoate

To a solution of 2-(tert-butoxycarbonylamino)-5-methoxy-5-oxo-pentanoic acid (200 g, 765 mmol) in 1,4-dioxane (1.5 L) were added di-tert-butyl dicarbonate (267 g, 1.22 mol) and pyridine (121 g, 1.53 mol). After the reaction mixture was stirred at 25° C. for 30 min, ammonium carbonate (182 g, 2.30 mol) was added to the mixture and stirred for additional 16 h at 25° C. The organic solvent was removed by rotary evaporation, the residue was acidified by HCl (6 M) to pH=3 and then extracted with ethyl acetate (800 mL×3). The combined organic phase was washed with brine (800 mL), dried over sodium sulfate, and filtered. Volatile organics were removed under reduced pressure to offer methyl 5-amino-4-(tert-butoxycarbonyl amino)-5-oxo-pentanoate (180 g, 90% yield) as a white solid. $^1$H NMR: 400 MHz CDCl$_3$ δ: 6.51 (s, 1H), 5.94 (s, 1H), 5.43 (s, 1H), 4.21 (s, 1H), 3.63 (s, 3H), 2.59-2.40 (m, 2H), 2.15-2.11 (m, 1H), 1.94-1.90 (m, 1H), 1.42 (s, 9H).

Methyl 4,5-diamino-5-oxo-pentanoate hydrochloride

A mixture of methyl 5-amino-4-(tert-butoxycarbonylamino)-5-oxo-pentanoate (180 g, 692 mmol) and HCl/ethyl acetate (300 mL, 4 M) was stirred at 25° C. for 12 h. The precipitated solid was collected by vacuum filtration and washed with ethyl acetate (500 mL) to give methyl 4,5-diamino-5-oxo-pentanoate hydrochloride (130 g, 95% yield) as a white solid. $^1$H NMR: 400 MHz CD$_3$OD δ: 4.00-3.96 (m, 1H), 3.70 (s, 3H), 2.59-2.52 (m, 2H), 2.22-2.13 (m, 2H).

Methyl 3-hydroxy-2-methyl-benzoate

Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) until pH>3. The solid was dried under vacuum at 45° C. to give methyl 3-hydroxy-2-methyl-benzoate (700 g, 80.4% yield) as a gray solid. $^1$H NMR: 400 MHz DMSO-d$_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate

Two batches (240 g each) were run in parallel. To a solution of methyl 3-hydroxy-2-methyl-benzoate (240 g, 1.44 mol) in N,N-dimethylformamide (1.40 L) was added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred and the organic phase was separated. The combined organic phase (two batches combined) was washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl) silyl]oxy-benzoate

Two batches (~375 g each) were run in parallel. To the isopropyl acetate solution of methyl 3-[tert-butyl(dimethyl)

silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) was removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl (dimethyl)silyl]oxy-benzoate (920 g, 95.5% yield) as dark orange oil. $^1$H NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

Methyl 5-amino-4-[4-[tert-butyl(dimethyl)silyl]oxy-1-oxo-isoindolin-2-yl]-5-oxo-pentanoate To a stirred solution of methyl 4,5-diamino-5-oxo-pentanoate hydrochloride (74.5 g, 379 mmol) in acetonitrile (2.50 L) was added methyl 2-(bromomethyl)-3-[tert-butyl (dimethyl)silyl] oxy-benzoate (125 g, 348 mmol). To the suspension was added diisopropylethylamine (89.9 g, 696 mmol) through an addition funnel over 10 min and then the mixture was stirred at 60° C. for 16 h. The reaction mixture was diluted with ethyl acetate (1.0 L), washed with HCl (1N, 1.0 L), sodium bicarbonate (sat. 1.0 L) and brine (1.0 L) successively. The organic layer was concentrated to give crude methyl 5-amino-4-[4-[tert-butyl(dimethyl)silyl]oxy-1-oxo-isoindolin-2-yl]-5-oxo-pentanoate (108 g, crude) as a light yellow solid. LCMS: m/z 407.3 [M+1]$^+$.

Methyl 5-amino-4-(4-hydroxy-1-oxo-isoindolin-2-yl)-5-oxo-pentanoate

To a stirred cold solution of methyl 5-amino-4-[4-[tert-butyl(dimethyl)silyl]oxy-1-oxo-isoindolin-2-yl]-5-oxo-pentanoate (108 g, 266 mmol) in N,N-dimethylformamide (350 mL) was added potassium carbonate (14.7 g, 106 mmol) in water (40 mL) in portions over 5 min. The resulting reaction mixture was stirred at 15° C. for 15 h. The reaction mixture was cooled in an ice bath, and HCl (12 M, 15 mL) was added slowly at 0-5° C. Acetonitrile (200 mL) was added to the mixture and precipitate solid formed. The suspension was stirred at room temperature for 10 min and filtered. The filter cake was washed with ethyl acetate (200 mL×5) to give product (55 g). The filtrate was concentrated under high vacuum to give a crude product (100 g) which was dissolved in dichloromethane (1.0 L) and allowed to stand at 15° C. for 16 hrs. White solid was formed which was filtered to give 5 g of product. The solids were combined to give methyl 5-amino-4-(4-hydroxy-1-oxo-isoindolin-2-yl)-5-oxo-pentanoate (60 g, 77% yield) as a white solid. $^1$H NMR: 400 MHz DMSO-$d_6$ δ: 7.58 (s, 1H), 7.31 (t, J=8.0 Hz, 1H), 7.19-7.14 (m, 2H), 7.01 (d, J=7.6 Hz, 1H), 4.75-4.71 (m, 1H), 4.50 (d, J=17.6 Hz, 1H), 4.32 (d, J=17.6 Hz, 1H), 3.51 (s, 3H), 2.29-2.18 (m, 3H), 2.09-1.99 (m, 1H).

Methyl 5-amino-4-[4-[[4-(bromomethyl)phenyl] methoxy]-1-oxo-isoindolin-2-yl]-5-oxo-pentanoate Two reactions (25 g, 85.5 mmol) were run in parallel. A mixture of 1,4-bis(bromomethyl)benzene (67.7 g, 257 mmol), potassium carbonate (11.8 g, 85.5 mmol) and methyl 5-amino-4-(4-hydroxy-1-oxo-isoindolin-2-yl)-5-oxo-pentanoate (25 g, 85.5 mmol) in acetonitrile (1 L) was stirred at 60° C. for 16 h. The two batches were combined and the mixture was cooled to 15° C. and filtered. The filtrate was concentrated and purified by silica gel column chromatography (eluted by 50% petroleum ether in ethyl acetate to 100% ethyl acetate) to afford methyl 5-amino-4-[4-[[4-(bromomethyl)phenyl]methoxy]-1-oxo-isoindolin-2-yl]-5-oxo-pentanoate (52 g, 63% yield) as a white solid. $^1$H NMR: 400 MHz DMSO-$d_6$ δ: 7.59 (s, 1H), 7.50-7.44 (m, 5H), 7.32-7.28 (m, 2H), 7.19 (s, 1H), 5.26 (s, 2H), 4.79-4.71 (m, 3H), 4.55 (d, J=17.6 Hz, 1H), 4.43 (d, J=17.6 Hz, 1H), 3.52 (s, 3H), 2.30-2.19 (m, 3H), 2.10-2.08 (m, 1H).

3-[4-[[4-(bromomethyl)phenyl]methoxy]-1-oxo-isoindolin-2-yl]piperidine-2,6-dione Two reactions (28.5 g, 60.0 mmol) were run in parallel. Methyl 5-amino-4-[4-[[4-(bromomethyl)phenyl]methoxy]-1-oxo-isoindolin-2-yl]-5-oxo-pentanoate (28.5 g, 60.0 mmol) was dissolved in tetrahydrofuran (720 mL) and the solution was cooled in dry ice/acetone bath to −70 OC. While stirring, potassium tert-butoxide (7.4 g, 66.0 mmol) was added in one portion to the clear solution. The reaction mixture turned to pale yellow and stirring was continued for additional 2 h at −70° C. A cooled solution of HCl (1N, 260 mL) was rapidly transferred to the reaction mixture while maintaining temperature at −70 OC. The mixture immediately turned milky white and the dry ice/acetone bath was removed. The mixture was concentrated to remove most of the tetrahydrofuran. Upon concentration of the reaction mixture, a white solid precipitated. The white slurry was diluted with water (500 mL) and then filtered. The filter cake was washed with water (500 mL) and dried in vacuum oven at 40° C. for 12 h, then washed with ethyl acetate (500 mL). The batches were combined to give 3-[4-[[4-(bromomethyl) phenyl]methoxy]-1-oxo-isoindolin-2-yl]piperidine-2,6-dione (49.85 g, 93%) as a light yellow solid. $^1$H NMR: 400 MHz DMSO-$d_6$ δ: 10.95 (s, 1H), 7.51-7.41 (m, 5H), 7.35-7.28 (m, 2H), 5.23 (s, 2H), 5.12-5.07 (m, 1H), 4.70 (s, 2H), 4.41 (d, J=17.6 Hz, 1H), 4.25 (d, J=17.6 Hz, 1H), 2.90-2.84 (m, 1H), 2.58-2.53 (m, 1H), 2.44-2.41 (m, 1H), 1.98-1.95 (m, 1H).

4-(4-(4-(((2-(2,6-dioxopiperidin-3-yl)-1-oxoisoindolin-4-yl)oxy)methyl)benzyl)piperazin-1-yl)-3-fluorobenzonitrile 3-(4-((4-(bromomethyl)benzyl)oxy)-1-oxoisoindolin-2-yl)piperidine-2,6-dione (5.0 g, 11.28 mmol) was placed in a flask with 3-fluoro-4-(piperazin-1-yl)benzonitrile (2.315 g, 11.28 mmol), diisopropylethylamine (5.91 ml, 33.8 mmol), and acetonitrile (100 ml). The reaction mixture was stirred at 40° C. for 18 h. Volatile organics were removed under reduced pressure and purification by standard methods provided 4-(4-(4-(((2-(2,6-dioxopiperidin-3-yl)-1-oxoisoindolin-4-yl)oxy)methyl)benzyl)piperazin-1-yl)-3-fluorobenzonitrile. $^1$H NMR (400 MHz, DMSO-$d_6$) δ 10.97 (s, 1H), 7.68 (dd, J=1.96, 13.45 Hz, 1H), 7.56 (dd, J=1.77, 8.38 Hz, 1H), 7.43-7.52 (m, 3H), 7.30-7.38 (m, 4H), 7.11 (t, J=8.80 Hz, 1H), 5.24 (s, 2H), 5.11 (dd, J=5.14, 13.33 Hz, 1H), 4.37-4.46 (m, 1H), 4.22-4.30 (m, 1H), 3.54 (s, 2H), 3.12-3.23 (m, 4H), 2.84-2.98 (m, 1H), 2.52-2.62 (m, 5H), 2.36-2.48 (m, 1H), 1.92-2.04 (m, 1H). MS (ESI) m/z 568.2 [M+1]$^+$. Anal. Calcd for $C_{32}H_{30}FN_5O_4$: C, 67.71; H, 5.33; N, 12.34. Found: C, 67.50; H, 5.44; N, 12.34.

Example 2: Synthesis of (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2)

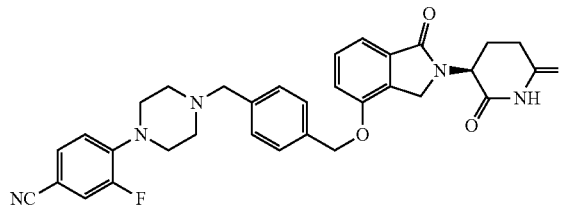

tert-Butyl (4S)-5-amino-4-(benzyloxycarbonylamino)-5-oxo-pentanoate

To a solution of (2S)-2-(benzyloxycarbonylamino)-5-tert-butoxy-5-oxo-pentanoic acid (150 g, 445 mmol) in 1,4-dioxane (1.50 L) was added di-tert-butyl dicarbonate (155 g, 711 mmol), pyridine (70.3 g, 889 mmol) and ammonium bicarbonate (105 g, 1.33 mol). The reaction mixture was stirred at 18° C. for 16 h and then concentrated. The residue was dissolved in ethyl acetate (5.0 L) and water (5.0 L), the organic layer was separated and washed with HCl (3.0 mL, 1 N), saturated sodium bicarbonate (3.0 L), brine (3.0 L), dried over anhydrous sodium sulfate, filtered and concentrated to give crude tert-butyl (4S)-5-amino-4-(benzyloxycarbonylamino)-5-oxo-pentanoate (450 g, crude) as a white solid, which was used in the next step without further purification. $^1$H NMR 400 MHz DMSO-$d_6$ δ: 7.35-7.30 (m, 5H), 7.02 (s, 1H), 5.01 (d, J=3.2 Hz, 1H), 3.93-3.90 (m, 1H), 2.20 (t, J=8.0 Hz, 2H), 1.88-1.84 (m, 1H), 1.72-1.69 (m, 1H), 1.35 (s, 9H).

tert-Butyl (4S)-4,5-diamino-5-oxo-pentanoate

To a solution of tert-butyl (4S)-5-amino-4-(benzyloxycarbonylamino)-5-oxo-pentanoate (112 g, 333 mmol) in methanol (1.0 L) was added 10% palladium on carbon (15 g) under nitrogen. The suspension was degassed under vacuum and purged with hydrogen several times. The mixture was stirred under hydrogen gas (40 psi) at 30° C. for 16 h. The reaction mixture was filtered and the filtrate was concentrated to give crude tert-butyl (4S)-4,5-diamino-5-oxo-pentanoate as a colorless oil. $^1$H NMR 400 MHz DMSO-$d_6$ δ: 7.30 (s, 1H), 6.95 (s, 1H), 3.10-3.07 (m, 1H), 2.27-2.23 (m, 2H), 1.69-1.78 (m, 1H), 1.59-1.55 (m, 1H), 1.38 (s, 9H).

Methyl 3-hydroxy-2-methyl-benzoate

Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) until pH>3. The solid was dried under vacuum at 45° C. to give methyl 3-hydroxy-2-methyl-benzoate (700 g, 80.4% yield) as a gray solid. $^1$H NMR: 400 MHz DMSO-$d_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate

Two batches (240 g each) were run in parallel. To a solution of methyl 3-hydroxy-2-methyl-benzoate (240 g, 1.44 mol) in N,N-dimethylformamide (1.40 L) were added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred followed by separation of the organic phase. The combined organics (two batches combined) were washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl)silyl]oxy-benzoate

Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) were removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. $^1$H NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

tert-Butyl (4S)-5-amino-4-[4-[tert-butyl(dimethyl)silyl]oxy-1-oxo-isoindolin-2-yl]-5-oxo-pentanoate To a solution of tert-butyl (4S)-4,5-diamino-5-oxo-pentanoate (130 g, 643 mmol) in acetonitrile (4.0 L) was added methyl 2-(bromomethyl)-3-[tert-butyl(dimethyl)silyl]oxy-benzoate (210 g, 584 mmol) and diisopropylethylamine (113 g, 877 mmol). The reaction mixture was stirred at 50° C. for 16 h. The reaction mixture was concentrated to remove most of the acetonitrile, the residue was dissolved in methyl tert-butyl ether (2.0 L) and water (1.5 L), the organic layer was washed with saturated monopotassium phosphate (1.0 L×2), brine (1.0 L), dried over anhydrous sodium sulfate, filtered and concentrated to give crude tert-butyl (4S)-5-amino-4-[4-[tert-butyl(dimethyl)silyl]oxy-1-oxo-isoindolin-2-yl]-5-oxo-pentanoate (524 g), which was used into next step without further purification.

tert-Butyl (4S)-5-amino-4-(4-hydroxy-1-oxo-isoindolin-2-yl)-5-oxo-pentanoate To a solution of tert-butyl (4S)-5-amino-4-[4-[tert-butyl(dimethyl)silyl]oxy-1-oxo-isoindolin-2-yl]-5-oxo-pentanoate (275 g, 613 mmol) in methanol (2.0 L) was added tetrabutylammonium fluoride trihydrate (38.7 g, 123 mmol). The mixture was stirred at 18° C. for 16 h. The reaction mixture was concentrated to remove most of the methanol, the residue was dissolved in dichloromethane/water (3 L/2 L), the organic layer was washed with brine (1.0 L), dried over anhydrous sodium sulfate, filtered, and concentrated to give crude product which was purified by silica gel column to give product (260 g). Product was added into acetonitrile (750 mL) and the mixture was stirred at 60° C. for 2 h, cooled to 18° C., and stirred for another 2 h. The solid was filtered and the cake was dried to give tert-butyl (4S)-5-amino-4-(4-hydroxy-1-oxo-isoindolin-2-yl)-5-oxo-pentanoate (248 g, 60.5% yield) as a gray solid. $^1$H NMR 400 MHz DMSO-d$_6$ δ: 10.00 (s, 1H), 7.54 (s, 1H), 7.29 (t, J=7.6 Hz, 1H), 7.14 (d, J=4.8 Hz, 2H), 4.72-4.68 (m, 1H), 4.49-4.28 (m, 2H), 2.17-1.97 (m, 4H), 1.31 (s, 9H).

4-(4-(4-(Chloromethyl)benzyl)piperazin-1-yl)-3-fluorobenzonitrile 1,4-Bis(chloromethyl)benzene (51.2 g, 292 mmol) was placed in a flask with acetonitrile (195 mL) and N,N-dimethylformamide (195 mL). The reaction mixture was stirred at ambient temperature until all the solids dissolved. Diisopropylamine (51.1 mL, 292 mmol) was then added along with 3-fluoro-4-(piperazin-1-yl)benzonitrile(20 g, 97 mmol). The reaction was heated to 60° C. for 1 h. The acetonitrile was removed under reduced pressure. The remaining mixture was partitioned between ethyl acetate (1.0 L), water (700 mL), and brine (300 mL). The organic layer was separated and the aqueous layer was extracted with ethyl acetate twice. Volatile organics were combined and removed under reduced pressure. The solid was dissolved in minimal dichloromethane and purified on silica gel column (0-100% ethyl acetate in hexanes over 3 L). Fractions containing desired product were combined and volatile organics were removed under reduced pressure. The residue was dissolved in minimal dichloromethane and purified a second time on silica gel column (10% isocratic ethyl acetate in hexanes over 800 mL followed by 20-80% ethyl acetate in hexanes over 4 L). Fractions containing desired product were combined and volatile organics were removed under reduced pressure to afford 4-(4-(4-(chloromethyl)benzyl)piperazin-1-yl)-3-fluorobenzonitrile (22.7 g, 66.0 mmol, 67.7% yield) as an off-white solid. $^1$H NMR (400 MHz, CDCl$_3$) δ ppm 7.33-7.39 (m, 5H) 7.29 (d, J=1.96 Hz, 1H) 7.25 (d, J=1.96 Hz, 1H) 6.91 (t, J=8.56 Hz, 1H) 4.60 (s, 2H) 3.58 (s, 2H) 3.19-3.27 (m, 4H) 2.58-2.66 (m, 4H). MS (ESI) m/z 344.2 [M+1]$^+$.

(S)-tert-Butyl 5-amino-4-(4-((4-((4-(4-cyano-2-fluorophenyl)piperazin-1-yl)methyl)benzyl)oxy)-1-oxoisoindolin-2-yl)-5-oxopentanoate (S)-tert-butyl 5-amino-4-(4-hydroxy-1-oxoisoindolin-2-yl)-5-oxopentanoate (22.05 g, 65.9 mmol) was placed in a flask with 4-(4-(4-(chloromethyl)benzyl)piperazin-1-yl)-3-fluorobenzonitrile (22.67 g, 65.9 mmol), potassium carbonate (18.23 g, 132 mmol), and N,N-dimethylformamide (330 mL). The reaction mixture was heated to 45° C. for 16 h. The reaction was diluted with ethyl acetate (50 mL) and filtered. The filtrate was partitioned with ethyl acetate (900 mL) and water (600 mL) and brine (200 mL). The organic layer was isolated and partitioned with water (600 mL). The organic layer was isolated and all organic layers were combined, dried over sodium sulfate, and volatiles were removed under reduced pressure. The residue was treated with 20% ethyl acetate in hexanes and volatiles were removed under reduced pressure to afford (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (44.02 g, 68.6 mmol, 104% yield) as an off-white solid. Yield was slightly over quantitative as some N, N-dimethylformamide remained. $^1$H NMR (400 MHz, CDCl$_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H). MS (ESI) m/z 642.4 [M+1]$^+$.

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (12.1 g, 18.86 mmol) was placed in a vial with acetonitrile (189 mL) and benzenesulfonic acid (3.96 g, 24.51 mmol). The reaction mixture was placed under vacuum and purged with nitrogen. This was repeated once more and the mixture was then heated to 85° C. overnight under a nitrogen atmosphere. The reaction mixture was poured warm directly into 2 separatory funnels containing dichloromethane (1000 mL) and ethyl acetate (300 mL). To this mixture a saturated solution of sodium bicarbonate (900 mL), water (100 mL), and brine (450 mL) was added. The organic layer was isolated and the aqueous layer was extracted with dichloromethane (800 mL) and ethyl acetate (200 mL). The combined organic layers were dried over anhydrous magnesium sulfate, and concentrated. Purification by standard methods provided the title compound. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

Example 3: Anti-CD3 Antibodies

Preferably the anti-CD3 antibody comprises a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3. Preferably the antibody comprises the variable domains of SEQ ID NO:7 (VH) and SEQ ID NO:8 (VL). Anti-CD3 antibody as described above was used to generate the T cell bispecific antibodies in accordance with the following example.

Example 4: Generation of Anti-BCMA/Anti-CD3 T Cell Bispecific Antibodies of Fc-Containing 2+1 Format cDNAs encoding the full heavy and light chains of the corresponding anti-BCMA IgG1 antibodies as well as the anti-CD3 VH and VL cDNAs were used as the starting materials. For each bispecific antibody, four protein chains were involved comprising the heavy and light chains of the corresponding anti-BCMA antibody and the heavy and light chains of the anti-CD3 antibody described above, respectively. In order to minimize the formation of side-products with mispaired heavy chains, for example with two heavy chains of the anti-CD3 antibody, a mutated heterodimeric Fc region is used carrying "knob-into-hole mutations" and an engineered disulphide bond, as described in WO2009080251 and in WO2009080252. In order to minimize the formation of side-products with mispaired light chains, for example with two light chains of the anti-BCMA antibody, a CH1×constant kappa crossover is applied to the heavy and light chains of the anti-CD3 antibody using the methodology described in WO2009080251 and in WO2009080252.

a) An anti-BCMA/anti-CD3 T cell bispecific antibody with a 2+1 format i.e. bispecific $(Fab)_2 \times (Fab)$ antibody that is bivalent for BCMA and monovalent for CD3 would have advantages on potency, predictability for efficacy and safety because it would preferentially bind to the tumor target BCMA and avoid CD3 antibody sink, thus higher probability for drug exposure focused to the tumor.

Anti-BCMA/anti-CD3 T cell bispecific of the 2+1 format (i.e. bispecific $(Fab)_2 \times (Fab)$ antibody bivalent for BCMA and monovalent for CD3 with Fc were produced for the human BCMA antibodies previously selected. cDNAs encoding the full Fabs (heavy chain VH and CH1 domains plus light chain VL and CL domains) of the corresponding anti-BCMA IgG1 antibodies as well as the anti-CD3 VH and VL cDNAs, were used as the starting materials. For each bispecific antibody, four protein chains were involved comprising the heavy and light chains of the corresponding anti-BCMA antibody and the heavy and light chains of the anti-CD3 antibody described above, respectively, with Fc regions.

Briefly, each bispecific antibody is produced by simultaneous cotransfection of four mammalian expression vectors encoding, respectively: a) the full light chain cDNA of the corresponding BCMA antibody, b) a fusion cDNA generated by standard molecular biology methods, such as splice-overlap-extension PCR, encoding a fusion protein made of (in N- to C-terminal order) secretory leader sequence, Fab (VH followed by CH1 domains) of the corresponding anti-BCMA antibody described above, a flexible glycine (Gly)-serine (Ser) linker with the sequence Gly-Gly-Gly-Gly-Ser-Gly-Gly-Gly-Gly-Ser, Fab (VH followed by CH1 domains) of the corresponding anti-BCMA antibody described above, a flexible glycine (Gly)-serine (Ser) linker with the sequence Gly-Gly-Gly-Gly-Ser-Gly-Gly-Gly-Gly-Ser, the VH of the anti-CD3 antibody described above and the constant kappa domain of a human light chain cDNA, c) a fusion cDNA generated by standard molecular biology methods, such as splice-overlap-extension PC, encoding a fusion protein made of (in N- to C-terminal order) secretory leader sequence, VL of the anti-CD3 antibody described above, constant CH1 domain of a human IgG1 cDNA. Co-transfection of mammalian cells and antibody production and purification using the methods described above for production of human or humanized IgG1 antibodies, with one modification: for purification of antibodies, the first capture step is not done using ProteinA, but instead is done using an affinity chromatography column packed with a resin binding to human kappa light chain constant region, such as KappaSelect (GE Healthcare Life Sciences). In addition, a disulfide can be included to increase the stability and yields as well as additional residues forming ionic bridges and increasing the heterodimerization yields (EP 1870459A1).

For the generation ofBCMAxCD3 bispecific antibody vectors, the IgG1 derived bispecific molecules consist at least of two antigen binding moieties capable of binding specifically to two distinct antigenic determinants CD3 and BCMA. The antigen binding moieties were Fab fragments composed of a heavy and a light chain, each comprising a variable and a constant region. At least one of the Fab fragments was a "Crossfab" fragment, wherein the constant domains of the Fab heavy and light chain were exchanged. The exchange of heavy and light chain constant domains within the Fab fragment assures that Fab fragments of different specificity do not have identical domain arrangements and consequently do not interchange light chains. The bispecific molecule design was monovalent for CD3 and bivalent for BCMA where one Fab fragment is fused to the N-terminus of the inner CrossFab (2+1). The bispecific molecule contained an Fc part in order to have a longer half-life. A schematic representation of the constructs is given in FIGS. 1A, 1B, 2A to 2D, and 3A to 3D; the sequences of the preferred constructs are shown in Table 2A. The molecules were produced by co-transfecting HEK293 EBNA cells growing in suspension with the mammalian expression vectors using polymer-based solution. For preparation of 2+1 CrossFab-IgG constructs, cells were transfected with the corresponding expression vectors in a 1:2:1:1 ratio ("vector Fc(knob)":"vector light chain":"vector light chain CrossFab":"vector heavy chain-CrossFab").

Example 5: Combined Use of Anti-BCMA/Anti-CD3 T Cell Bispecific Antibody with a Compound T Cell Activation and Cytokine Release.

Purified T cells are thawed in RPMI 1640 media containing 10% FBS and 1 ng/mL human IL-7. The cells are counted in a Vi-CELL cell counter and diluted with the cell media to $2 \times 10^6$ cells/mL. The T cells are allowed to recover in a 37° C., 5% $CO_2$ incubator overnight. The T cells are treated with a bispecific antibody specifically binding to human B cell maturation antigen (BCMA) and to human CD3ε (CD3) provided herein or Compound 1, Compound 2 or Compound 3 as single agent alone or in combination for 24, 48, and 72 hours. The cells are collected at each time point and profiled by FACS analysis for T cell activation markers (CD25, CD69, and HLA-DR) on CD3+CD4+ and CD3+CD8+ subsets. The culture media is also collected at each time point and analyzed for cytokines by MesoScale Discovery or Luminex platforms.

Co-Cultures of Effector T Cells (E) and Tumor Cells (T).

Pretreated T cells and/or tumor cells with a bispecific antibody specifically binding to human B cell maturation antigen (BCMA) and to human CD3ε (CD3) provided herein or Compound 1, Compound 2 or Compound 3 single agent or combination are cocultured together with different E:T ratios at 37° C., 5% $CO_2$ and are evaluated at 24, 48, or 72 hours for T-cell induced tumor killing by FACS assays. The tumor cells are labeled with CFSE (5(6)-carboxyfluorescein N-hydroxysuccinimidyl ester) according to the manufacturer's instructions just prior to the start of the coculture assay. In addition, T-cell activation markers (CD25, CD69, HLA-DR) are monitored by FACS on the CD3+CD4+ and CD3+CD8+ subsets.

In one embodiment, combination treatment will show an enhanced depth of response in lenalidomide- and/or pomalidomide-resistant cells compared to either single agent alone. In another embodiment, combination treatment will show synergistic and/or additive cell killing activity in myeloma cells with low to no BCMA expression. In addition, combination treatment will show an increase in T-cell activation and cytokine production (such as IL-2, IFN-gamma, and TNF-alpha) compared to either single agent alone.

Example 6: Combined Use of Anti-BCMA/Anti-CD3 T Cell Bispecific Antibody with a Compound Co-Cultures of Effector T Cells (E) and Target Cells (T) after Pretreatment with Compounds.

CD3+ T-cells were isolated from peripheral blood mononuclear cell fractions from healthy donors using magnetic-activated cell sorting. Cells were thawed in RPMI 1640 culture media supplemented with 10% (v/v) fetal bovine serum (FBS), non-essential amino acids and sodium pyruvate. All cell cultures and cell treatments were performed in a 37° C., 5% $CO_2$ incubator for time periods as indicated. T-cells were then labeled with CFSE (carboxyfluorescein succinimidyl ester) according to the manufacturer's instructions, and allowed to recover overnight in the presence of 1 ng/mL human IL-7. T-cells were treated with DMSO (control) or Compound 2 as single agent for 16 hours before co-culture. The multiple myeloma H929 and OPM-2 cell lines or the plasma cell leukemia (PCL) cell line L363 were labeled with CellTrace™ Violet, then pretreated with DMSO (control) or Compound 2 as a single agent for 72 hours. T-cells and target cells were then washed to remove compounds and co-cultured in the presence of increasing concentrations of a bispecific antibody specifically binding to human B cell maturation antigen (BCMA) and to human CD3ε (CD3) as provided herein, for 72 hours, at different effector T-cell (E) to target cell (T) ratios. The cells were collected at the end of co-culture for analysis of target cell apoptosis and necrosis by flow cytometry using APC Annexin V Apoptosis Detection Kit with 7-AAD, following the manufacturer's directions (BioLegend). The results demonstrated that pretreatment of target cells by Compound 2 significantly increased the potency of the bispecific antibody (for both H929 and L363 cells), as well as the maximal target cell killing (for H929 cells) induced by the bispecific antibody as tested (FIGS. 4A and 4B). In cytotoxicity assays with OPM-2 cells, the results showed that treatment of either the effector T-cells or target cells alone by Compound 2 increased the potency and efficacy of target cell killing by the bispecific antibody as tested (FIG. 4C). For OPM-2 cytotoxicity assays, the combination of effector T-cell pretreatment and target cell pretreatment with Compound 2 resulted in the greatest potentiation and increase in efficacy of the bispecific antibody as tested (FIG. 4C).

Co-Cultures of Effector T Cells (E) and Target Cells (T) with Concurrent Compound Treatments.

CD3+ T-cells were isolated from peripheral blood mononuclear cell fractions from three different healthy donors (donors A, B and C) using magnetic-activated cell sorting. Cells were thawed in RPMI 1640 culture media supplemented with 10% (v/v) FBS, non-essential amino acids, sodium pyruvate and penicillin/streptomycin. All cell cultures and treatments were performed in a 37° C., 5% $CO_2$ incubator for time periods as indicated. T-cells were then labeled with CFSE (carboxyfluorescein succinimidyl ester) according to the manufacturer's instructions, and allowed to recover overnight in the presence of 1 ng/mL human IL-7. The multiple myeloma H929 cell line was labeled with CellTrace™ Violet, and allowed to recover overnight. T-cells and target cells were then washed and co-cultured in the presence of increasing concentrations of bispecific antibody specifically binding to human B cell maturation antigen (BCMA) and to human CD3ε (CD3) provided herein, for 72 hours, at a fixed effector T-cell (E) to target cell (T) ratio of 1:3. Co-cultures in the presence of bispecific antibody were performed in the presence of DMSO (control) or Compound 2. Cells were collected at the end of co-culture for analysis of target cell apoptosis and necrosis by flow cytometry using APC Annexin V Apoptosis Detection Kit with 7-AAD. The results demonstrated that for all donors tested, concurrent exposure of cells to Compound 2 significantly increased the potency of the bispecific antibody as tested, and also improved the maximal efficacy of target cell killing mediated by the bispecific antibody (FIG. 5).

Example 7: Combined Use of Anti-BCMA/Anti-CD3 T Cell Bispecific Antibody with a Compound in Lenalidomide-Resistant Multiple Myeloma Co-cultures of effector T cells (E) and lenalidomide-resistant multiple myeloma target cells (T) after pretreatment with compounds. CD3+ T-cells were isolated from peripheral blood mononuclear cell fractions from three different healthy donors (donors D, E and F) using magnetic-activated cell sorting. Cells were thawed in RPMI 1640 culture media supplemented with 10% (v/v) fetal bovine serum (FBS), non-essential amino acids, sodium pyruvate and penicillin/streptomycin. All cell cultures and cell treatments were performed in a 37° C., 5% $CO_2$ incubator for time periods as indicated. T-cells were then labeled with CFSE (carboxyfluorescein succinimidyl ester) according to the manufacturer's instructions, and allowed to recover overnight in the presence of 1 ng/mL human IL-7. The lenalidomide-resistant multiple myeloma cell line H929-1051 was generated by long-term culture in the presence of increasing concentrations of lenalidomide, as previously described (Ghandi et al. Br. J. Haematol. 2014 January; 164(2):233-44) using methods described (Lopez-Girona et al. Leukemia. 2012 November; 26(11):2326-35). H929-1051 cells were labeled with CellTrace™ Violet, then pretreated with DMSO (control), pomalidomide, or Compound 2 as a single agent for 72 hours. T-cells and target cells were then washed to remove compounds and co-cultured in the presence of increasing concentrations of the bispecific antibody specifically binding to human B cell maturation antigen (BCMA) and to human CD3ε (CD3) as provided herein, for 72 hours, at a fixed effector T-cell (E) to target cell (T) ratio of 1:3. The cells were collected at the end of co-culture for analysis of target cell apoptosis and necrosis by flow cytometry using APC Annexin V Apoptosis Detection Kit with 7-AAD, following the manufacturer's directions (BioLegend). The results demonstrated that pretreatment of lenalidomide-resistant H929-1051 target cells by Compound 2, but not by pretreatment with pomalidomide, increased the potency and maximal target cell killing induced by the bispecific antibody as tested (FIG. 6). The data suggest the cell line is also pomalidomide-resistant.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating multiple myeloma comprising administering to a patient in need thereof a therapeutically effective amount of a compound of formula 1 or an enantiomer, mixture of enantiomers, tautomer, isotopolog, or pharmaceutically acceptable salt thereof;
in combination with a bispecific antibody comprising a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO:17 and a VL region comprising a CDR3L region of SEQ ID NO:20 and a CDR1L and CDR2L region combination selected from the group of
   i) CDR1L region of SEQ ID NO:23 and CDR2L region of SEQ ID NO:24,
   ii) CDR1L region of SEQ ID NO:25 and CDR2L region of SEQ ID NO:26, or
   iii) CDR1L region of SEQ ID NO:27 and CDR2L region of SEQ ID NO:28.

2. A method of treating multiple myeloma comprising administering to a patient in need thereof a therapeutically effective amount of a compound of formula 2 or a tautomer, isotopolog, or pharmaceutically acceptable salt thereof;
in combination with a bispecific antibody comprising a first binding part specifically binding to human B cell maturation antigen (BCMA) and a second binding part specifically binding to human CD3ε (CD3), characterized in that said first binding part comprises a VH region comprising a CDR1H region of SEQ ID NO:21, a CDR2H region of SEQ ID NO:22 and a CDR3H region of SEQ ID NO:17 and a VL region comprising a CDR3L region of SEQ ID NO:20 and a CDR1L and CDR2L region combination selected from the group of
   i) CDR1L region of SEQ ID NO:23 and CDR2L region of SEQ ID NO:24,
   ii) CDR1L region of SEQ ID NO:25 and CDR2L region of SEQ ID NO:26, or
   iii) CDR1L region of SEQ ID NO:27 and CDR2L region of SEQ ID NO:28.

3. The method of claim 1, wherein the multiple myeloma is relapsed, refractory or resistant.

4. The method of claim 3, wherein the multiple myeloma is refractory or resistant to lenalidomide.

5. The method of claim 3, wherein the multiple myeloma is refractory or resistant to pomalidomide.

6. The method of claim 1, wherein the multiple myeloma is newly diagnosed multiple myeloma.

7. The method of claim 1, wherein the multiple myeloma is plasma cell leukemia.

8. The method of claim 1, wherein the compound is administered prior to the bispecific antibody.

9. The method of claim 1, wherein the compound is administered concurrently with the bispecific antibody.

10. The method of claim 1, wherein the compound is administered subsequent to the bispecific antibody.

11. The method of claim 1, additionally comprising administering an additional active agent.

12. The method of claim 2, wherein the multiple myeloma is relapsed, refractory or resistant.

13. The method of claim 12, wherein the multiple myeloma is refractory or resistant to lenalidomide.

14. The method of claim 12, wherein the multiple myeloma is refractory or resistant to pomalidomide.

15. The method of claim 2, wherein the multiple myeloma is newly diagnosed multiple myeloma.

16. The method of claim 2, wherein the multiple myeloma is plasma cell leukemia.

17. The method of claim 2, wherein the compound is administered prior to the bispecific antibody.

18. The method of claim 2, wherein the compound is administered concurrently with the bispecific antibody.

19. The method of claim 2, wherein the compound is administered subsequent to the bispecific antibody.

20. The method of claim 2, additionally comprising administering an additional active agent.

* * * * *

UNITED STATES PATENT AND TRADEMARK OFFICE
CERTIFICATE OF CORRECTION

PATENT NO. : 11,439,637 B2
APPLICATION NO. : 16/419971
DATED : September 13, 2022
INVENTOR(S) : Pierce et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 546 days.

Signed and Sealed this
Fourth Day of February, 2025

Coke Morgan Stewart
*Acting Director of the United States Patent and Trademark Office*

SEQUENCE LISTING

<160> NUMBER OF SEQ ID NOS: 57

<210> SEQ ID NO 1
<211> LENGTH: 5
<212> TYPE: PRT
<213> ORGANISM: Mus musculus

<400> SEQUENCE: 1

Thr Tyr Ala Met Asn
1               5

<210> SEQ ID NO 2
<211> LENGTH: 19
<212> TYPE: PRT
<213> ORGANISM: Mus musculus

<400> SEQUENCE: 2

Arg Ile Arg Ser Lys Tyr Asn Asn Tyr Ala Thr Tyr Tyr Ala Asp Ser
1               5                   10                  15

Val Lys Gly

<210> SEQ ID NO 3
<211> LENGTH: 14
<212> TYPE: PRT
<213> ORGANISM: Mus musculus

<400> SEQUENCE: 3

His Gly Asn Phe Gly Asn Ser Tyr Val Ser Trp Phe Ala Tyr
1               5                   10

<210> SEQ ID NO 4
<211> LENGTH: 14
<212> TYPE: PRT
<213> ORGANISM: Mus musculus

<400> SEQUENCE: 4

Gly Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Mus musculus

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Mus musculus

<400> SEQUENCE: 6

Ala Leu Trp Tyr Ser Asn Leu Trp Val
1               5

<210> SEQ ID NO 7
<211> LENGTH: 125
<212> TYPE: PRT
<213> ORGANISM: Mus musculus

<400> SEQUENCE: 7

Glu Val Gln Leu Leu Glu Ser Gly Gly Gly Leu Val Gln Pro Gly Gly

```
1               5                   10                  15
Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
                115                 120                 125

<210> SEQ ID NO 8
<211> LENGTH: 109
<212> TYPE: PRT
<213> ORGANISM: Mus musculus

<400> SEQUENCE: 8

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 9
<211> LENGTH: 116
<212> TYPE: PRT
<213> ORGANISM: Artificial Sequence
<220> FEATURE:
<223> OTHER INFORMATION: 83A10 Heavy Chain Variable region (VH)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Val Leu Gly Trp Phe Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Mab21/Mab22/Mab42 Heavy Chain Variable region

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 11
<211> LENGTH: 109
<212> TYPE: PRT
<213> ORGANISM: Artificial Sequence
<220> FEATURE:
<223> OTHER INFORMATION: 83A10 Light Chain Variable region (VL)

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 12
<211> LENGTH: 109
<212> TYPE: PRT
<213> ORGANISM: Artificial Sequence
<220> FEATURE:
<223> OTHER INFORMATION: Mab21/Mab27/Mab33/Mab39 Light Chain Variable region

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Glu Tyr
            20                  25                  30

Tyr Leu Ala Trp Tyr Gln Gln Lys Pro Gly Gln Ala Pro Arg Leu Leu
        35                  40                  45

Ile Glu His Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 13
<211> LENGTH: 109
<212> TYPE: PRT
<213> ORGANISM: Artificial Sequence
<220> FEATURE:
<223> OTHER INFORMATION: Mab22 Light Chain Variable region (VL)

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Tyr Leu Ala Trp Tyr Gln Gln Lys Pro Gly Gln Ala Pro Arg Leu Leu
        35                  40                  45

Ile Ser Gly Ala Gly Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 14
<211> LENGTH: 109
<212> TYPE: PRT
<213> ORGANISM: Artificial Sequence
<220> FEATURE:
<223> OTHER INFORMATION: Mab42 Light Chain Variable region (VL)

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
        35                  40                  45

Ile His Ser Ala Ser Thr Arg Ala Thr Gly Ile Pro Asp Arg Phe Ser
    50                  55                  60

Gly Ser Gly Ser Gly Thr Asp Phe Thr Leu Ala Ile Ser Arg Leu Glu

```
                65                  70                  75                  80
Pro Glu Asp Phe Ala Val Tyr Tyr Cys Gln Gln Tyr Gly Tyr Pro Pro
                        85                  90                  95
Asp Phe Thr Phe Gly Gln Gly Thr Lys Val Glu Ile Lys
                100                 105
```

<210> SEQ ID NO 15
<211> LENGTH: 5
<212> TYPE: PRT
<213> ORGANISM: Homo sapiens
<220> FEATURE:
<223> OTHER INFORMATION: 83A10 CDR1H

<400> SEQUENCE: 15

```
Ser Tyr Ala Met Ser
1               5
```

<210> SEQ ID NO 16
<211> LENGTH: 17
<212> TYPE: PRT
<213> ORGANISM: Homo sapiens
<220> FEATURE:
<223> OTHER INFORMATION: 83A10 CDR2H

<400> SEQUENCE: 16

```
Ala Ile Ser Gly Ser Gly Gly Ser Thr Tyr Tyr Ala Asp Ser Val Lys
1               5                   10                  15
Gly
```

<210> SEQ ID NO 17
<211> LENGTH: 7
<212> TYPE: PRT
<213> ORGANISM: Homo sapiens
<220> FEATURE:
<223> OTHER INFORMATION: 83A10/Mab21/Mab22/Mab42/Mab27/Mab33/Mab39 CDR3H

<400> SEQUENCE: 17

```
Val Leu Gly Trp Phe Asp Tyr
1               5
```

<210> SEQ ID NO 18
<211> LENGTH: 13
<212> TYPE: PRT
<213> ORGANISM: Homo sapiens
<220> FEATURE:
<223> OTHER INFORMATION: 83A10 CDR1L

<400> SEQUENCE: 18

```
Arg Ala Ser Gln Ser Val Ser Ser Ser Tyr Leu Ala Trp
1               5                   10
```

<210> SEQ ID NO 19
<211> LENGTH: 8
<212> TYPE: PRT
<213> ORGANISM: Homo sapiens
<220> FEATURE:
<223> OTHER INFORMATION: 83A10 CDR2L

<400> SEQUENCE: 19

```
Tyr Gly Ala Ser Ser Arg Ala Thr
1               5
```

<210> SEQ ID NO 20
<211> LENGTH: 10
<212> TYPE: PRT

```
<213> ORGANISM: Homo sapiens
<220> FEATURE:
<223> OTHER INFORMATION: 83A10/Mab21/Mab22/Mab42 CDR3L

<400> SEQUENCE: 20

Gln Gln Tyr Gly Tyr Pro Pro Asp Phe Thr
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Mab21/Mab22/Mab42 CDR1H

<400> SEQUENCE: 21

Asp Asn Ala Met Gly
1               5

<210> SEQ ID NO 22
<211> LENGTH: 17
<212> TYPE: PRT
<213> ORGANISM: Artificial Sequence
<220> FEATURE:
<223> OTHER INFORMATION: Mab21/Mab22/Mab42 CDR2H

<400> SEQUENCE: 22

Ala Ile Ser Gly Pro Gly Ser Ser Thr Tyr Tyr Ala Asp Ser Val Lys
1               5                   10                  15

Gly

<210> SEQ ID NO 23
<211> LENGTH: 13
<212> TYPE: PRT
<213> ORGANISM: Artificial Sequence
<220> FEATURE:
<223> OTHER INFORMATION: Mab21 CDR1L

<400> SEQUENCE: 23

Arg Ala Ser Gln Ser Val Ser Glu Tyr Tyr Leu Ala Trp
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Mab21 CDR2L

<400> SEQUENCE: 24

Glu His Ala Ser Thr Arg Ala Thr
1               5

<210> SEQ ID NO 25
<211> LENGTH: 13
<212> TYPE: PRT
<213> ORGANISM: Artificial Sequence
<220> FEATURE:
<223> OTHER INFORMATION: Mab22 CDR1L

<400> SEQUENCE: 25

Arg Ala Ser Gln Ser Val Ser Ser Tyr Tyr Leu Ala Trp
1               5                   10

<210> SEQ ID NO 26
<211> LENGTH: 8
```

```
<212> TYPE: PRT
<213> ORGANISM: Artificial Sequence
<220> FEATURE:
<223> OTHER INFORMATION: Mab22 CDR2L

<400> SEQUENCE: 26

Ser Gly Ala Gly Ser Arg Ala Thr
1               5

<210> SEQ ID NO 27
<211> LENGTH: 13
<212> TYPE: PRT
<213> ORGANISM: Artificial Sequence
<220> FEATURE:
<223> OTHER INFORMATION: Mab42 CDR1L

<400> SEQUENCE: 27

Arg Ala Ser Gln Ser Val Ser Asp Glu Tyr Leu Ser Trp
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Mab42 CDR2L

<400> SEQUENCE: 28

His Ser Ala Ser Thr Arg Ala Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Mab27 CDR1H

<400> SEQUENCE: 29

Ser Ala Pro Met Gly
1               5

<210> SEQ ID NO 30
<211> LENGTH: 16
<212> TYPE: PRT
<213> ORGANISM: Artificial Sequence
<220> FEATURE:
<223> OTHER INFORMATION: Mab27 CDR2H

<400> SEQUENCE: 30

Ala Ile Ser Tyr Ile Gly His Thr Tyr Tyr Ala Asp Ser Val Lys Gly
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: Mab27/Mab33/Mab39 CDR1L

<400> SEQUENCE: 31

Arg Ala Ser Gln Ser Val Ser Glu Tyr Tyr Leu Ala
1               5                   10

<210> SEQ ID NO 32
<211> LENGTH: 7
<212> TYPE: PRT
```

```
<213> ORGANISM: Artificial Sequence
<220> FEATURE:
<223> OTHER INFORMATION: Mab27/Mab33/Mab39 CDR2L

<400> SEQUENCE: 32

His Ala Ser Thr Arg Ala Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Mab27/Mab33/Mab39 CDR3L

<400> SEQUENCE: 33

Gln Gln Tyr Gly Tyr Pro Pro Asp Phe Thr
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Mab33 CDR1H

<400> SEQUENCE: 34

Thr Asn Ala Met Gly
1               5

<210> SEQ ID NO 35
<211> LENGTH: 17
<212> TYPE: PRT
<213> ORGANISM: Artificial Sequence
<220> FEATURE:
<223> OTHER INFORMATION: Mab33 CDR2H

<400> SEQUENCE: 35

Ala Ile Asn Arg Phe Gly Gly Ser Thr Tyr Tyr Ala Asp Ser Val Lys
1               5                   10                  15

Gly

<210> SEQ ID NO 36
<211> LENGTH: 5
<212> TYPE: PRT
<213> ORGANISM: Artificial Sequence
<220> FEATURE:
<223> OTHER INFORMATION: Mab39 CDR1H

<400> SEQUENCE: 36

Gln Asn Ala Met Gly
1               5

<210> SEQ ID NO 37
<211> LENGTH: 17
<212> TYPE: PRT
<213> ORGANISM: Artificial Sequence
<220> FEATURE:
<223> OTHER INFORMATION: Mab39 CDR2H

<400> SEQUENCE: 37

Ala Ile Ser Pro Thr Gly Phe Ser Thr Tyr Tyr Ala Asp Ser Val Lys
1               5                   10                  15

Gly
```

```
<210> SEQ ID NO 38
<211> LENGTH: 115
<212> TYPE: PRT
<213> ORGANISM: Artificial Sequence
<220> FEATURE:
<223> OTHER INFORMATION: Mab27 VH

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Pro Met Gly Trp Val Arg Gln Ala Pro Gly Lys Gly Leu Glu Trp Val
        35                  40                  45

Ser Ala Ile Ser Tyr Ile Gly His Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Val Leu Gly Trp Phe Asp Tyr Trp Gly Gln Gly Thr Leu Val Thr
            100                 105                 110

Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Mab33 VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Thr Asn
            20                  25                  30

Ala Met Gly Trp Val Arg Gln Ala Pro Gly Lys Gly Leu Glu Trp Val
        35                  40                  45

Ser Ala Ile Asn Arg Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: Mab39 VH

<400> SEQUENCE: 40

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Gln Asn
            20                  25                  30

Ala Met Gly Trp Val Arg Gln Ala Pro Gly Lys Gly Leu Glu Trp Val
        35                  40                  45

Ser Ala Ile Ser Pro Thr Gly Phe Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
            115

<210> SEQ ID NO 41
<211> LENGTH: 103
<212> TYPE: PRT
<213> ORGANISM: Artificial Sequence
<220> FEATURE:
<223> OTHER INFORMATION: 83A10/Mab21/Mab22/Mab42 BCMA CH1

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys
            100

<210> SEQ ID NO 42
<211> LENGTH: 107
<212> TYPE: PRT
<213> ORGANISM: Artificial Sequence
<220> FEATURE:
<223> OTHER INFORMATION: 83A10/Mab21/Mab22/Mab42 BCMA CL

<400> SEQUENCE: 42

Arg Thr Val Ala Ala Pro Ser Val Phe Ile Phe Pro Pro Ser Asp Arg
1               5                   10                  15

Lys Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

```
                    85                  90                  95

Pro Val Thr Lys Ser Phe Asn Arg Gly Glu Cys
            100                 105

<210> SEQ ID NO 43
<211> LENGTH: 103
<212> TYPE: PRT
<213> ORGANISM: Artificial Sequence
<220> FEATURE:
<223> OTHER INFORMATION: CD3 CH1

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 44
<211> LENGTH: 107
<212> TYPE: PRT
<213> ORGANISM: Artificial Sequence
<220> FEATURE:
<223> OTHER INFORMATION: CD3 CL

<400> SEQUENCE: 44

Ala Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 45
<211> LENGTH: 671
<212> TYPE: PRT
<213> ORGANISM: Artificial Sequence
<220> FEATURE:
<223> OTHER INFORMATION: 83A10 knob HC

<400> SEQUENCE: 45

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430
```

```
Thr Lys Val Asp Lys Lys Val Glu Pro Lys Ser Cys Asp Lys Thr His
            435                 440                 445

Thr Cys Pro Pro Cys Pro Ala Pro Glu Ala Ala Gly Gly Pro Ser Val
450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
            515                 520                 525

Val Leu Thr Val Leu His Gln Asp Trp Leu Asn Gly Lys Glu Tyr Lys
        530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 46
<211> LENGTH: 446
<212> TYPE: PRT
<213> ORGANISM: Artificial Sequence
<220> FEATURE:
<223> OTHER INFORMATION: 83A10 hole HC

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 47
<211> LENGTH: 216
<212> TYPE: PRT
<213> ORGANISM: Artificial Sequence
<220> FEATURE:
<223> OTHER INFORMATION: 83A10 LC

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Tyr Pro Pro
                 85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 48
<211> LENGTH: 232
<212> TYPE: PRT
<213> ORGANISM: Artificial Sequence
<220> FEATURE:
<223> OTHER INFORMATION: CD3 LC

<400> SEQUENCE: 48

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 49
<211> LENGTH: 671
<212> TYPE: PRT
<213> ORGANISM: Artificial Sequence
<220> FEATURE:
<223> OTHER INFORMATION: Mab21 knob HC

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
            325                 330                 335

Thr Val Leu Ser Ser Ala Ser Thr Lys Gly Pro Ser Val Phe Pro Leu
        340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
            405                 410                 415

Leu Gly Thr Gln Thr Tyr Ile Cys Asn Val Asn His Lys Pro Ser Asn
        420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Ala Ala Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
            485                 490                 495

Val Lys Phe Asn Trp Tyr Val Asp Gly Val Glu Val His Asn Ala Lys
        500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
            565                 570                 575

Pro Cys Arg Asp Glu Leu Thr Lys Asn Gln Val Ser Leu Trp Cys Leu
        580                 585                 590

Val Lys Gly Phe Tyr Pro Ser Asp Ile Ala Val Glu Trp Glu Ser Asn
    595                 600                 605

Gly Gln Pro Glu Asn Asn Tyr Lys Thr Thr Pro Pro Val Leu Asp Ser
610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
            645                 650                 655

His Asn His Tyr Thr Gln Lys Ser Leu Ser Leu Ser Pro Gly Lys
        660                 665                 670

<210> SEQ ID NO 50
<211> LENGTH: 446
<212> TYPE: PRT
<213> ORGANISM: Artificial Sequence
<220> FEATURE:
<223> OTHER INFORMATION: Mab21 hole HC

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
             20                  25                  30

Ala Met Gly Trp Val Arg Gln Ala Pro Gly Lys Gly Leu Glu Trp Val
         35                  40                  45

Ser Ala Ile Ser Gly Pro Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys

<210> SEQ ID NO 51
<211> LENGTH: 216
<212> TYPE: PRT
<213> ORGANISM: Artificial Sequence
<220> FEATURE:
<223> OTHER INFORMATION: Mab21 LC

<400> SEQUENCE: 51

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Glu Tyr
            20                  25                  30

Tyr Leu Ala Trp Tyr Gln Gln Lys Pro Gly Gln Ala Pro Arg Leu Leu
        35                  40                  45

Ile Glu His Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 52
<211> LENGTH: 671
<212> TYPE: PRT
<213> ORGANISM: Artificial Sequence
<220> FEATURE:
<223> OTHER INFORMATION: Mab22 knob HC

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                 85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Gly Gly Gly Gly
        210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
        290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
        370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Ala Ala Gly Gly Pro Ser Val
        450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
```

```
                500                 505                 510
Thr Lys Pro Arg Glu Gln Tyr Asn Ser Thr Tyr Arg Val Val Ser
            515                 520                 525
Val Leu Thr Val Leu His Gln Asp Trp Leu Asn Gly Lys Glu Tyr Lys
        530                 535                 540
Cys Lys Val Ser Asn Lys Ala Leu Gly Ala Pro Ile Glu Lys Thr Ile
545                 550                 555                 560
Ser Lys Ala Lys Gly Gln Pro Arg Glu Pro Gln Val Tyr Thr Leu Pro
                565                 570                 575
Pro Cys Arg Asp Glu Leu Thr Lys Asn Gln Val Ser Leu Trp Cys Leu
            580                 585                 590
Val Lys Gly Phe Tyr Pro Ser Asp Ile Ala Val Glu Trp Glu Ser Asn
        595                 600                 605
Gly Gln Pro Glu Asn Asn Tyr Lys Thr Thr Pro Val Leu Asp Ser
            610                 615                 620
Asp Gly Ser Phe Phe Leu Tyr Ser Lys Leu Thr Val Asp Lys Ser Arg
625                 630                 635                 640
Trp Gln Gln Gly Asn Val Phe Ser Cys Ser Val Met His Glu Ala Leu
                645                 650                 655
His Asn His Tyr Thr Gln Lys Ser Leu Ser Leu Ser Pro Gly Lys
            660                 665                 670

<210> SEQ ID NO 53
<211> LENGTH: 446
<212> TYPE: PRT
<213> ORGANISM: Artificial Sequence
<220> FEATURE:
<223> OTHER INFORMATION: Mab22 hole HC

<400> SEQUENCE: 53

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asp Asn
            20                  25                  30
Ala Met Gly Trp Val Arg Gln Ala Pro Gly Lys Gly Leu Glu Trp Val
        35                  40                  45
Ser Ala Ile Ser Gly Pro Gly Ser Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Val Leu Gly Trp Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Glu Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
```

```
                195                 200                 205
Lys Val Asp Glu Lys Val Glu Pro Lys Ser Cys Asp Lys Thr His Thr
            210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Gly Ala Pro Ile Glu Lys Thr Ile Ser
                325                 330                 335
Lys Ala Lys Gly Gln Pro Arg Glu Pro Gln Val Cys Thr Leu Pro Pro
            340                 345                 350
Ser Arg Asp Glu Leu Thr Lys Asn Gln Val Ser Leu Ser Cys Ala Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Val Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 54
<211> LENGTH: 216
<212> TYPE: PRT
<213> ORGANISM: Artificial Sequence
<220> FEATURE:
<223> OTHER INFORMATION: Mab22 LC

<400> SEQUENCE: 54

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Tyr Leu Ala Trp Tyr Gln Gln Lys Pro Gly Gln Ala Pro Arg Leu Leu
        35                  40                  45
Ile Ser Gly Ala Gly Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Tyr Pro Pro
                85                  90                  95
Asp Phe Thr Phe Gly Gln Gly Thr Lys Val Glu Ile Lys Arg Thr Val
            100                 105                 110
Ala Ala Pro Ser Val Phe Ile Phe Pro Pro Ser Asp Arg Lys Leu Lys
```

```
            115                 120                 125
Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 55
<211> LENGTH: 671
<212> TYPE: PRT
<213> ORGANISM: Artificial Sequence
<220> FEATURE:
<223> OTHER INFORMATION: Mab42 knob HC

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
```

-continued

Gly Gln Ala Phe Arg Gly Leu Ile Gly Gly Thr Asn Lys Arg Ala Pro
260                 265                 270

Gly Thr Pro Ala Arg Phe Ser Gly Ser Leu Leu Gly Gly Lys Ala Ala
275                 280                 285

Leu Thr Leu Ser Gly Ala Gln Pro Glu Asp Glu Ala Glu Tyr Tyr Cys
290                 295                 300

Ala Leu Trp Tyr Ser Asn Leu Trp Val Phe Gly Gly Gly Thr Lys Leu
305                 310                 315                 320

Thr Val Leu Ser Ser Ala Ser Thr Lys Gly Pro Ser Val Phe Pro Leu
325                 330                 335

Ala Pro Ser Ser Lys Ser Thr Ser Gly Gly Thr Ala Ala Leu Gly Cys
340                 345                 350

Leu Val Lys Asp Tyr Phe Pro Glu Pro Val Thr Val Ser Trp Asn Ser
355                 360                 365

Gly Ala Leu Thr Ser Gly Val His Thr Phe Pro Ala Val Leu Gln Ser
370                 375                 380

Ser Gly Leu Tyr Ser Leu Ser Ser Val Val Thr Val Pro Ser Ser Ser
385                 390                 395                 400

Leu Gly Thr Gln Thr Tyr Ile Cys Asn Val Asn His Lys Pro Ser Asn
405                 410                 415

Thr Lys Val Asp Lys Lys Val Glu Pro Lys Ser Cys Asp Lys Thr His
420                 425                 430

Thr Cys Pro Pro Cys Pro Ala Pro Glu Ala Ala Gly Gly Pro Ser Val
435                 440                 445

Phe Leu Phe Pro Pro Lys Pro Lys Asp Thr Leu Met Ile Ser Arg Thr
450                 455                 460

Pro Glu Val Thr Cys Val Val Val Asp Val Ser His Glu Asp Pro Glu
465                 470                 475                 480

Val Lys Phe Asn Trp Tyr Val Asp Gly Val Glu Val His Asn Ala Lys
485                 490                 495

Thr Lys Pro Arg Glu Glu Gln Tyr Asn Ser Thr Tyr Arg Val Val Ser
500                 505                 510

Val Leu Thr Val Leu His Gln Asp Trp Leu Asn Gly Lys Glu Tyr Lys
515                 520                 525

Cys Lys Val Ser Asn Lys Ala Leu Gly Ala Pro Ile Glu Lys Thr Ile
530                 535                 540

Ser Lys Ala Lys Gly Gln Pro Arg Glu Pro Gln Val Tyr Thr Leu Pro
545                 550                 555                 560

Pro Cys Arg Asp Glu Leu Thr Lys Asn Gln Val Ser Leu Trp Cys Leu
565                 570                 575

Val Lys Gly Phe Tyr Pro Ser Asp Ile Ala Val Glu Trp Glu Ser Asn
580                 585                 590

Gly Gln Pro Glu Asn Asn Tyr Lys Thr Thr Pro Pro Val Leu Asp Ser
595                 600                 605

Asp Gly Ser Phe Phe Leu Tyr Ser Lys Leu Thr Val Asp Lys Ser Arg
610                 615                 620

Trp Gln Gln Gly Asn Val Phe Ser Cys Ser Val Met His Glu Ala Leu
625                 630                 635                 640

His Asn His Tyr Thr Gln Lys Ser Leu Ser Leu Ser Pro Gly Lys
645                 650                 655

660                 665                 670

<210> SEQ ID NO 56

```
<211> LENGTH: 446
<212> TYPE: PRT
<213> ORGANISM: Artificial Sequence
<220> FEATURE:
<223> OTHER INFORMATION: Mab42 hole HC

<400> SEQUENCE: 56
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Asn |
| | | | 20 | | | | | 25 | | | | | 30 | | |
| Ala | Met | Gly | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Ser | Gly | Pro | Gly | Ser | Ser | Thr | Tyr | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Val | Leu | Gly | Trp | Phe | Asp | Tyr | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | 115 | | | | | 120 | | | | | 125 | | | |
| Pro | Ser | Ser | Lys | Ser | Thr | Ser | Gly | Gly | Thr | Ala | Ala | Leu | Gly | Cys | Leu |
| 130 | | | | | 135 | | | | | 140 | | | | | |
| Val | Glu | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Glu | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Ala | Ala | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | 275 | | | | | 280 | | | | | 285 | | | |
| Lys | Pro | Arg | Glu | Glu | Gln | Tyr | Asn | Ser | Thr | Tyr | Arg | Val | Val | Ser | Val |
| 290 | | | | | 295 | | | | | 300 | | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Gly | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Cys | Thr | Leu | Pro | Pro |
| | | | 340 | | | | | 345 | | | | | 350 | | |
| Ser | Arg | Asp | Glu | Leu | Thr | Lys | Asn | Gln | Val | Ser | Leu | Ser | Cys | Ala | Val |
| | | 355 | | | | | 360 | | | | | 365 | | | |
| Lys | Gly | Phe | Tyr | Pro | Ser | Asp | Ile | Ala | Val | Glu | Trp | Glu | Ser | Asn | Gly |
| 370 | | | | | 375 | | | | | 380 | | | | | |

Gln Pro Glu Asn Asn Tyr Lys Thr Thr Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 57
<211> LENGTH: 216
<212> TYPE: PRT
<213> ORGANISM: Artificial Sequence
<220> FEATURE:
<223> OTHER INFORMATION: Mab42 LC

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
            35                  40                  45

Ile His Ser Ala Ser Thr Arg Ala Thr Gly Ile Pro Asp Arg Phe Ser
50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
210                 215